US009228001B2

(12) United States Patent
Tweten

(10) Patent No.: US 9,228,001 B2
(45) Date of Patent: Jan. 5, 2016

(54) MUTANTS OF CHOLESTEROL-DEPENDENT CYTOLYSINS AND USES THEREOF

(75) Inventor: Rodney K. Tweten, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 862 days.

(21) Appl. No.: 13/401,460

(22) Filed: Feb. 21, 2012

(65) Prior Publication Data

US 2012/0148624 A1 Jun. 14, 2012

Related U.S. Application Data

(63) Continuation of application No. 12/102,696, filed on Apr. 14, 2008, now Pat. No. 8,128,939.

(60) Provisional application No. 60/923,281, filed on Apr. 13, 2007.

(51) Int. Cl.

| | |
|---|---|
| *C12N 5/10* | (2006.01) |
| *A61K 39/02* | (2006.01) |
| *C12N 1/21* | (2006.01) |
| *C12N 1/15* | (2006.01) |
| *C12N 1/19* | (2006.01) |
| *C12N 15/63* | (2006.01) |
| *C07K 14/33* | (2006.01) |
| *C07K 14/32* | (2006.01) |
| *C07H 21/04* | (2006.01) |
| *A61K 39/08* | (2006.01) |
| *A61K 39/07* | (2006.01) |
| *C07K 14/315* | (2006.01) |
| *A61K 39/09* | (2006.01) |
| *C07K 14/195* | (2006.01) |
| *C12N 7/01* | (2006.01) |
| *C07K 14/31* | (2006.01) |
| *A61K 38/00* | (2006.01) |
| *A61K 39/00* | (2006.01) |

(52) U.S. Cl.

CPC ............... *C07K 14/32* (2013.01); *C07K 14/195* (2013.01); *C07K 14/31* (2013.01); *C07K 14/3156* (2013.01); *C07K 14/33* (2013.01); *A61K 38/00* (2013.01); *A61K 39/00* (2013.01)

(58) Field of Classification Search

None

See application file for complete search history.

(56) References Cited

U.S. PATENT DOCUMENTS

| | | | |
|---|---|---|---|
| 4,686,102 | A | 8/1987 | Ridchey et al. |
| 5,565,204 | A | 10/1996 | Kuo et al. |
| 6,224,880 | B1 | 5/2001 | Chan et al. |
| 6,632,441 | B2 | 10/2003 | Schlievert et al. |
| 6,716,432 | B1 | 4/2004 | Paton et al. |
| 6,764,686 | B2 | 7/2004 | Minetti et al. |
| 6,887,480 | B1 | 5/2005 | Adamou et al. |
| 6,903,184 | B1 | 6/2005 | Ades et al. |
| 7,045,132 | B2 | 5/2006 | Sampson et al. |
| 7,122,194 | B2 | 10/2006 | Johnson et al. |
| 7,125,548 | B2 | 10/2006 | Smith |
| 7,132,107 | B2 | 11/2006 | Adamou et al. |
| 7,217,791 | B2 | 5/2007 | Chen et al. |
| 7,262,024 | B2 | 8/2007 | Hamel et al. |
| 7,820,789 | B2 | 10/2010 | Kirkham et al. |

FOREIGN PATENT DOCUMENTS

| | | |
|---|---|---|
| EP | 08827230 | 12/2010 |
| EP | 11174235 | 9/2011 |
| WO | WO 90/06951 | 12/1989 |
| WO | WO 2005/076696 | 8/2005 |
| WO | PCT/US08/60250 | 4/2009 |

OTHER PUBLICATIONS

Anonymous: "Prevention of Pneumococcal Disease: Recommendations of the Advisory Committee on Immunization Practices (ACIP)" Morbidity and Mortality Weekly Report—Recommendations and Reports vol. 46, (Apr. 4, 1997) 20 pages.

Alexander et al., "Amino acid changes affecting the activity of pneumolysin alter the behavior of Pneumococci in pneumonia" Microbial Pathogenesis, Academic Press Limited, New York, NY, vol. 24, No. 3, Mar. 1, 1998, pp. 167-174.

Berry et al., "Effect of Defined Point Mutations in the Pneumolysin Gene on the Virulence of *Streptococcus pneumoniae*" Infection and Immunity, May 1995, vol. 63, No. 5, p. 1969-1974.

Boslego et al., "Vaccines and Immunotherapy" Pergaman Press, 1991, "Gonorrhea Vaccines" Chapter 17, pp. 211-223).

Bowie et al., "Deciphering the Message in Protein Sequences: Tolerance to Amino Acid Substitutions" Science, 1990, vol. 257, pp. 1306-1310.

Ellis, "Plotkin & Mortimer—Vaccines," W.B. Saunders Company, 1988, "New Technologies for Making Vaccines" Chapter 29, pp. 568-575.

Greenspan et al., "Defining epitopes: It's not as easy as it seems" Nature Biotechnology vol. 17, pp. 936-937, Oct. 1999.

Kirkham et al., Symposium on Pneumococcal and Pneumococcal Diseases, Helsinki, Finland (online) www.congrer.fi/isppd-4/immages/abstract/pdf.

Kirkham et al., Immunology 113(s1):2, Nov. 26, 2004, Abstract.

Kirkham et al., "Construction and Immunological Characterization of a Novel Nontoxic Protective Pneumolysin Mutant for Use in Future Pneumococcal Vaccines," (Jan. 2006) vol. 74, No. 1, pp. 586-593.

Ramachandran, et al., "Structural insights into the membrane-anchoring mechanism of a cholesterol-dependent cytolysin" Nat. Struct. Biol. vol. 9, pp. 823-827, Nov. 2002.

(Continued)

*Primary Examiner* — Robert A Zeman

(57) ABSTRACT

Mutants of cholesterol-dependent cytolysins comprising at least one amino acid substitution in at least one of Loop 1, Loop 2, or Loop 3 of Domain 4, nucleic acids, vectors, and host cells encoding such polypeptide mutants, and compositions and vaccines comprising such polypeptide mutants.

11 Claims, 9 Drawing Sheets

(56) References Cited

OTHER PUBLICATIONS

Soltani, et al., "Specific protein-membrane contacts are required for prepore and pore assembly by a cholesterol-dependent cytolysin" J. Biol. Chem . Paper is press 282 (21), pp. 15709-15716, Apr. 5, 2007.

Soltani, et al., "Structural elements of the cholesterol-dependent cytolysins that are responsible for their cholesterol-sensitive membrane interactions", PNAS, vol. 104, No. 51, pp. 20226-20231, Dec. 18, 2007.

Tweten, "MiniReview: Cholesterol-Dependent Cytolysins, a Family of Versatile Pore-Forming Toxins" Infection and Immunity, vol. 73, No. 10, pp. 6199-6209, Oct. 2005.

Figure 10

MUTANTS OF CHOLESTEROL-DEPENDENT CYTOLYSINS AND USES THEREOF

CROSS-REFERENCE TO RELATED APPLICATIONS

The present application is a continuation application of U.S. Ser. No. 12/102,696, filed Apr. 14, 2008, now U.S. Pat. No. 8,128,939, issued Mar. 6, 2012; which claims the benefit under 35 U.S.C. 119(e) of U.S. Provisional Application Ser. No. 60/923,281, filed Apr. 13, 2007, the entirety of which is hereby expressly incorporated herein by reference.

STATEMENT REGARDING FEDERALLY SPONSORED RESEARCH OR DEVELOPMENT

This invention was made with government support under Grant 5R01AI037657 awarded by the National Institutes of Health. The government has certain rights in the invention.

BACKGROUND OF THE INVENTION

The cholesterol-dependent cytolysins (CDCs) are a large family of pore-forming toxins that are produced by more than 20 species from the genera *Clostridium, Streptococcus, Listeria, Bacillus*, and *Arcanobacterium*. The pore-forming mechanism of these toxins exhibits two hallmark characteristics: an absolute dependence on the presence of membrane cholesterol and the formation of an extraordinarily large pore. Each CDC is produced as a soluble monomeric protein that, with the exception of one member, is secreted by a type II secretion system. Upon encountering a eukaryotic cell, the CDCs undergo a transformation from a soluble monomeric protein to a membrane-embedded supramolecular pore complex. The conversion of the monomers to an oligomeric, membrane-inserted pore complex requires some extraordinary changes in the structure of the monomer.

Although the CDCs are well known as beta-hemolytic proteins, it has become increasingly apparent that bacterial pathogens use these proteins in much more sophisticated ways than as simple hemolysins or general cell-lytic agents. The CDC structure also exhibits a plasticity that has allowed the evolution of unique features for some CDCs, without compromising the fundamental pore-forming mechanism. Some of these features are reflected in CDCs that activate complement, that utilize a nonsterol receptor, that exhibit a pH-sensitive, poreforming mechanism, or that can function as a protein translocation channel.

CDC's are β-sheet-rich, four-domain proteins. A highly conserved tryptophan-rich undecapeptide is present in domain 4, which participates in the binding of some CDCs to cholesterol-rich membranes. In addition, three other short hydrophobic loops (Loops L1, L2 and L3) juxtaposed to the undecapeptide at the tip of domain 4 have been shown to also insert into the membrane surface and anchor the CDC to the membrane in a perpendicular orientation. After membrane binding, the CDC monomers diffuse laterally to initiate formation of the membrane oligomer.

Once the prepore complex reaches a large size, presumably a complete ring structure, it then makes the transition to the pore complex. The transmembrane pore is formed when two α-helical bundles in domain 3 of each monomer within the prepore complex are converted to two extended amphipathic transmembrane β-hairpins (TMHs). Upon the conversion of the prepore to the pore, the height of the prepore structure undergoes a vertical collapse of about 40 Angstroms. The collapse of the prepore structure brings the domain 3 TMHs within striking distance of the membrane surface, at which point they undergo a concerted insertion into the membrane that results in the formation of the large transmembrane β-barrel pore. The CDC pore is large: it is comprised of 35 to 50 monomers and exhibits a diameter of 250 to 300 Angstroms.

During the process of the CDC monomer interaction with the membrane, the undecapeptide and the three other short loops (L1, L2, L3) at the tip of the domain 4 β-sandwich insert into the membrane upon the interaction of the CDC monomers with the membrane surface. These loops do not penetrate deeply into the membrane and apparently do not directly participate in the structure of the transmembrane pore. One function of the loops appears to be to anchor the monomers to the membrane in an upright position. Domain 4 exists in a perpendicular orientation to the membrane and is surrounded by the aqueous milieu, even in the oligomeric state.

Domain 4 of the CDCs mediates membrane recognition, whether it is via cholesterol or another receptor, as in the case of ILY.

The CDCs are also capable of the lysis of a wide variety of nucleated cell types in vitro, and this capacity has in turn has been used by many investigators to permeabilize various eukaryotic cell types with CDCs. Despite the ability of these toxins to perform as general cell-lytic agents in vitro, it has not yet been demonstrated that cell lysis is a primary function of the CDCs during an infection. The contribution of CDCs to infection has been studied for example in *Listeria monocytogenes, Streptococcus pyogenes, Streptococcus pneumoniae, Arcanobacterium pyogenes*, and *Clostridium perfringens*. The results of some of these studies suggest that the bacteria use the CDCs in more sophisticated ways than as general cytolytic agents. It also appears that the CDC structure has undergone some unique evolutionary transformations that facilitate the pathogenic mechanism of these bacterial species.

*Streptococcus pneumoniae* is an important agent of disease in humans, especially among infants, the elderly, persons with chronic illness, and immunocompromised persons. It is a bacterium frequently isolated from patients with invasive diseases such as bacteremia/septicemia, pneumonia, and meningitis with high morbidity and mortality throughout the world. Even with appropriate antibiotic therapy, pneumococcal infections still result in many deaths. Although the advent of antimicrobial drugs has reduced the overall mortality from pneumococcal disease, the presence of resistant pneumococcal strains has become a major problem in the world today and underscores the need for treating and preventing pneumococcal infection by methods in addition to antimicrobials. Effective pneumococcal vaccines could have a major impact on the morbidity and mortality associated with *S. pneumoniae* disease. Such vaccines would also potentially be useful to prevent otitis media in infants and young children. New immunogenic pneumococcal vaccines that provide long-term immunity are clearly needed, especially for children aged less than 2 years, because incidence of disease is high and antibody responses to the polysaccharide vaccine antigens are poor in this age group.

Each year in the United States, pneumococcal disease accounts for an estimated 3,000 cases of meningitis, 50,000 cases of bacteremia, 500,000 cases of pneumonia, and 7 million cases of otitis media.

Severe pneumococcal infections result from dissemination of bacteria to the bloodstream and the central nervous system. In 1997, data from community-based studies indicated that overall annual incidence of pneumococcal bacteremia in the United States was an estimated 15-30 cases per 100,000 population; the rate was higher for persons aged greater than or equal to 65 years (50-83 cases per 100,000 population) and for children aged less than or equal to 2 years (160 cases per 100,000 population). In adults, 60%-87% of pneumococcal bacteremia was associated with pneumonia; in young children, the primary sites of infection were frequently not identified.

In the United States, the risk for acquiring bacteremia is lower among white persons than among persons in other racial/ethnic groups (i.e., blacks, Alaskan Natives, and American Indians). Black adults have a threefold to fivefold higher overall incidence of bacteremia (49-58 cases per 100,000 population) than whites. Rates of invasive pneumococcal disease are exceptionally high among Alaskan Natives and American Indians. The age-adjusted annual incidence of invasive pneumococcal infection among Alaskan Natives and Alaskan Native children aged less than 2 years was determined by a prospective surveillance study to be 74 cases and 624 cases per 100,000 population, respectively. Rates for meningitis and bacteremic pneumonia are eightfold to tenfold higher for Alaskan Natives of all ages than for other U.S. population groups. The highest incidence rates for any U.S. population have been reported among specific American Indian groups (e.g., Apache). The overall annual incidence for such groups is 156 cases per 100,000 population; the incidence for children aged 1-2 years in these groups is 2,396 cases per 100,000 population.

In the United States, the estimated overall annual incidence of pneumococcal meningitis is one to two cases per 100,000 population. The incidence of pneumococcal meningitis is highest among children aged 6-24 months and persons aged greater than or equal to 65 years. Rates for blacks are twice as high as those for whites and Hispanics. Because the incidence of Haemophilus influenzae type b (Hib) meningitis in children rapidly decreased following the introduction of Hib conjugate vaccines, S. pneumoniae has become the most common cause of bacterial meningitis in the United States (26).

Strains of drug-resistant S. pneumoniae (DRSP) have become increasingly common in the United States and in other parts of the world. In some areas, as many as 35% of pneumococcal isolates have been reported to have intermediate—(minimum inhibitory concentration {MIC}=0.1-1.0 ug/mL) or high-level (MIC greater than or equal to 2 ug/mL) resistance to penicillin. Many penicillin-resistant pneumococci are also resistant to other antimicrobial drugs (e.g., erythromycin, trimethoprim-sulfamethoxazole, and extended-spectrum cephalosporins). High-level penicillin resistance and multidrug resistance often complicate the management of pneumococcal infection and make choosing empiric antimicrobial therapy for suspected cases of meningitis, pneumonia, and otitis media increasingly difficult. Treating patients infected with nonsusceptible organisms may require the use of expensive alternative antimicrobial agents and may result in prolonged hospitalization and increased medical costs. The impact of antimicrobial resistance on mortality is not clearly defined. Emerging antimicrobial resistance further emphasizes the need for preventing pneumococcal infections by vaccination.

The currently available pneumococcal vaccines, manufactured by both Merck and Company, Inc. (Pneumovax 23™) and Lederle Laboratories (Pnu-Immune 23™), include 23 purified capsular polysaccharide antigens of S. pneumoniae (serotypes 1, 2, 3, 4, 5, 6B, 7F, 8, 9N, 9V, 10A, 11A, 12F, 14, 15B, 17F, 18C, 19A, 19F, 20, 22F, 23F, and 33F). These vaccines were licensed in the United States in 1983 and replaced an earlier 14-valent formulation that was licensed in 1977. One dose (0.5 mL) of the 23-valent vaccine contains 25 ug of each capsular polysaccharide antigen dissolved in isotonic saline solution with phenol (0.25%) or thimerosal (0.01%) added as preservative and no adjuvant. As of 1997, the 23 capsular types in the vaccine represented at least 85%-90% of the serotypes that cause invasive pneumococcal infections among children and adults in the United States. The six serotypes (6B, 9V, 14, 19A, 19F, and 23F) that most frequently caused invasive drug-resistant pneumococcal infection in the United States as of 1997 are represented in the 23-valent vaccine. As noted below, the desirability of a vaccine solely comprised of capsular polysaccharides is limited.

Pneumolysin in particular is a key component in the pathogenesis of streptococcal pneumonia, which kills over a million humans per year worldwide. The use of pneumolysin as a part of a vaccine for Streptococcus pneumoniae lung infections and otitis media is becoming increasingly important since vaccines based on the capsular polysaccharide are losing effectiveness due to genetic variation and are difficult to generate since there are more than 90 different capsular serotypes of Streptococcus pneumoniae. The immunity to one capsular type does not protect against another capsular type. The currently available pneumococcal vaccine discussed above, which comprises 23 capsular polysaccharides from the strains that most frequently cause disease, has significant shortcomings related primarily to the poor immunogenicity of some capsular polysaccharides, the diversity of the serotypes and the differences in the distribution of serotypes over time, geographic areas and age groups. Hence, the focus for vaccine development has shifted away from the bacterial capsule to various pneumococcal proteins, pneumolysin being considered as a necessary component for all subunit vaccines. Currently, a single mutant of pneumolysin has been used for vaccine development. This pneumolysin mutant (referred to as "Pd-B") contains a single mutation at position 433 (wherein the native tryptophan residue has been changed to a phenylalanine). This mutation in pneumolysin is in the conserved undecapeptide of Domain 4, the structure within the cholesterol-dependent cytolysins (CDCs), which has long been thought to mediate binding to mammalian membranes. Other mutants of pneumolysin are described in U.S. Pat. No. 6,716,432, for example.

While the pneumolysin Pd-B mutant is conventionally used for vaccine development, this protein is still able to undergo a variety of structural transitions that occur after binding to the membrane of mammalian cells. These changes dramatically alter its structure and may decrease its ability to stimulate an effective neutralizing immune response in a patient, primarily because the structure of pneumolysin that the patient's immune system may "see" will be that of the terminal cell-bound oligomeric complex instead of the initial structure of the soluble monomeric pneumolysin. More importantly, the current genetically toxoided pneumolysin is still hampered by an unacceptable level of toxicity. The basis for this toxicity is not yet clear, but likely results from the fact that this toxoid can still bind to and oligomerize on mammalian cells.

Therefore, mutants of cholesterol-dependent cytolysins, such as pneumolysin, which are both non-toxic and which do not bind to cell membranes and which are non-hemolytic yet which stimulate an immune response against corresponding disease organisms would be of great benefit.

BRIEF DESCRIPTION OF THE DRAWINGS

Figure 1A:
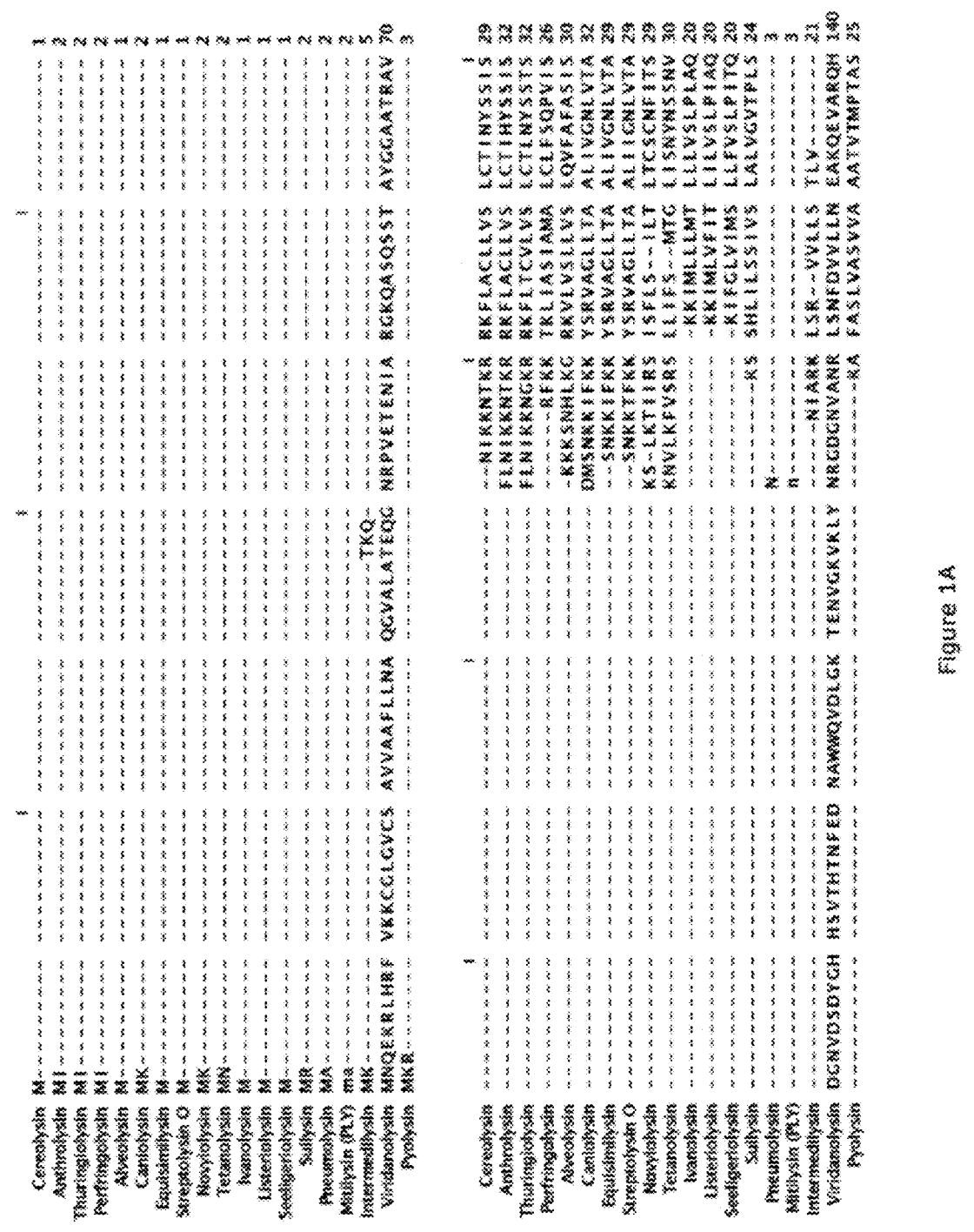
Figure 1B:
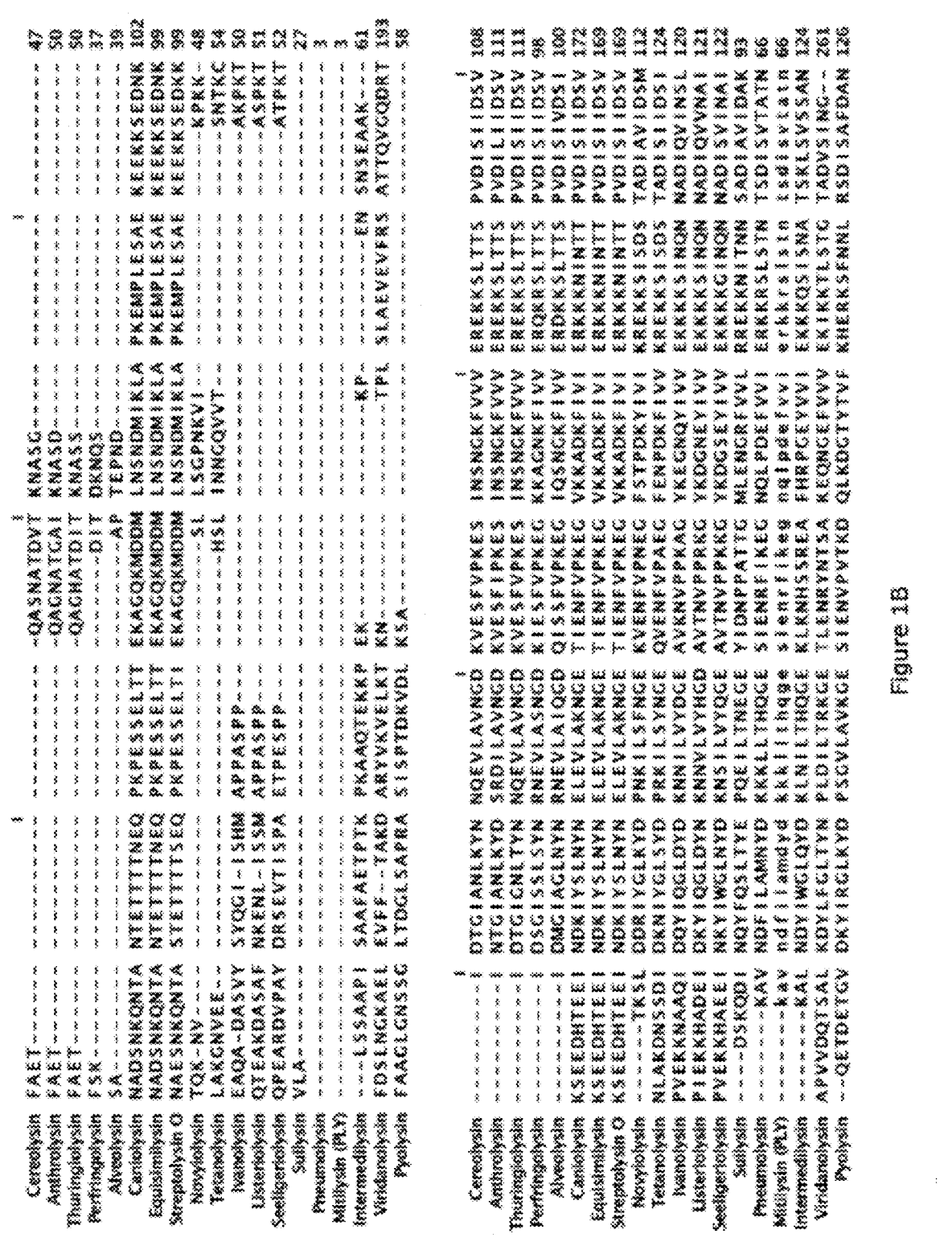
Figure 1C:
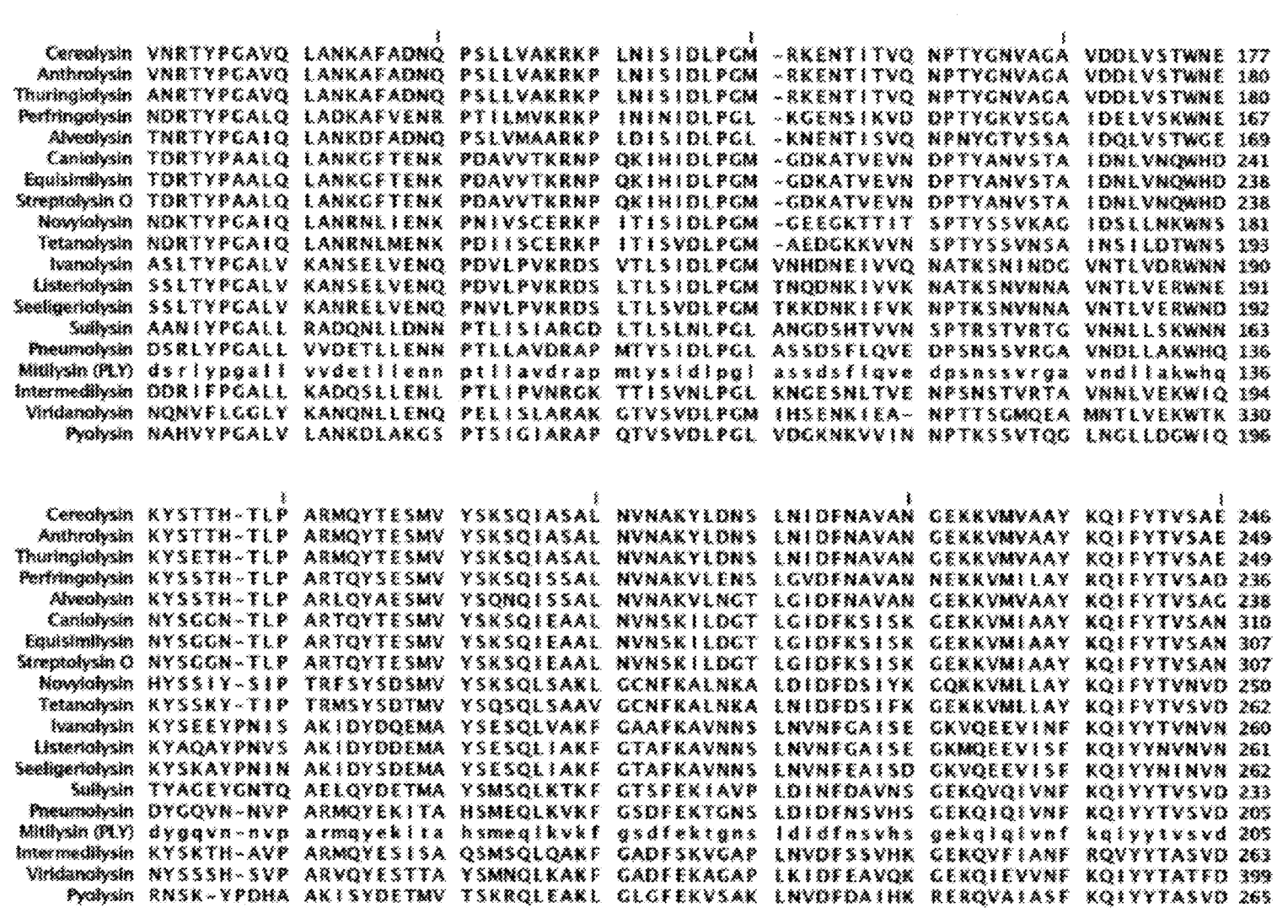

FIG. 1A-E is an amino acid alignment comparison of native amino acid sequences of various cholesterol-dependent cytolysins. The amino acid sequences of each protein identified herein correspond to the SEQ ID NO's in Table 1 herein, for example Cereolysin in FIG. 1A-E corresponds in SEQ ID NO:2 in Table 1. SEQ ID No:18 (PAF) in Table 1 corresponds to Viridanolysin in FIG. 1A-E.

FIG. 2 shows the crystal structure of ILY (Intermedilysin) and a comparison of the D4 crystal structures of ILY and PFO (Perfringolysin). Shown in (a) is a ribbon representation of the crystal structure of ILY[25] denoting the positions of various structures and residues referred to in these studies. Shown in (b) is an overlay of a ribbon representation of the D4 structures of ILY and PFO based on the crystal structures of both proteins[23, 24]. Shown are the relative locations of the undecapeptide for both proteins and the L1-L3 loops residues of ILY and PFO (the latter in parentheses). The structural images were generated using VMD[25].

FIG. 3. The ILY undecapeptide inserts into cholesterol-depleted membranes. ILY residue Ala-486 was mutated to a cysteine (ILY$^{A486C}$) and derivatized with NBD. The fluorescence emission of the NBD was determined when ILY$^{A486C\text{-}NBD}$ was incubated alone (solid line), with human red blood cells (hRBCs-dashed line), or with hRBCs depleted of cholesterol (dotted line).

FIG. 4. L1, L2, and L3 of ILY do not insert into cholesterol-depleted membranes. Each D4 loop residue known to insert into the membrane was substituted for a cysteine and modified with NBD. ILY$^{A428C\text{-}NBD}$ (b), or ILY$^{L518C\text{-}NBD}$ (c) was incubated alone (solid line), with hRBCs (dashed line), or with hRBCs depleted of cholesterol (dotted line). Membrane cholesterol was then restored and the insertion of L1, L2, and L3 determined. ILY$^{A428C\text{-}NBD}$ (d), ILY$^{A464C\text{-}NBD}$ (e), or ILY$^{L518C\text{-}NBD}$ (f) was incubated alone (solid line) or with cholesterol replete membranes (dashed line).

FIG. 5. The L1-L3 loops mediate PFO binding to cholesterol-rich liposomes, (a) SPR analysis of the binding of native (solid line) and NEM modified PFO (dashed line), (b) SPR analysis of the binding of native PFO (solid line), PFO$^{A401D}$ (long dashed line), PFO$^{A437D}$ (short dashed line) and PFO$^{L491D}$ (dotted line).

FIG. 6. Chemical modification of the PFO undecapeptide cysteine sulfhydryl blocks the membrane insertion of the undecapeptide tryptophans and conversion of the prepore to pore. The increase in the intrinsic fluorescence emission of the PFO undecapeptide tryptophans has been used to measure their insertion into the membrane[20, 21]. (a) The increase in the intrinsic fluorescence emission of the tryptophans in native PFO is shown as it moves from its soluble form (solid line) to its membrane-bound state (dashed line). (b) The same experiment shown in (a) was repeated with native PFO that had been modified at Cys-459 with NEM.

FIG. 7 shows the immunogenic response in mice immunized with a mutant and a wild-type pneumolysin then inoculated with *S. pneumoniae*.

DETAILED DESCRIPTION OF THE INVENTION

Figure 1E:
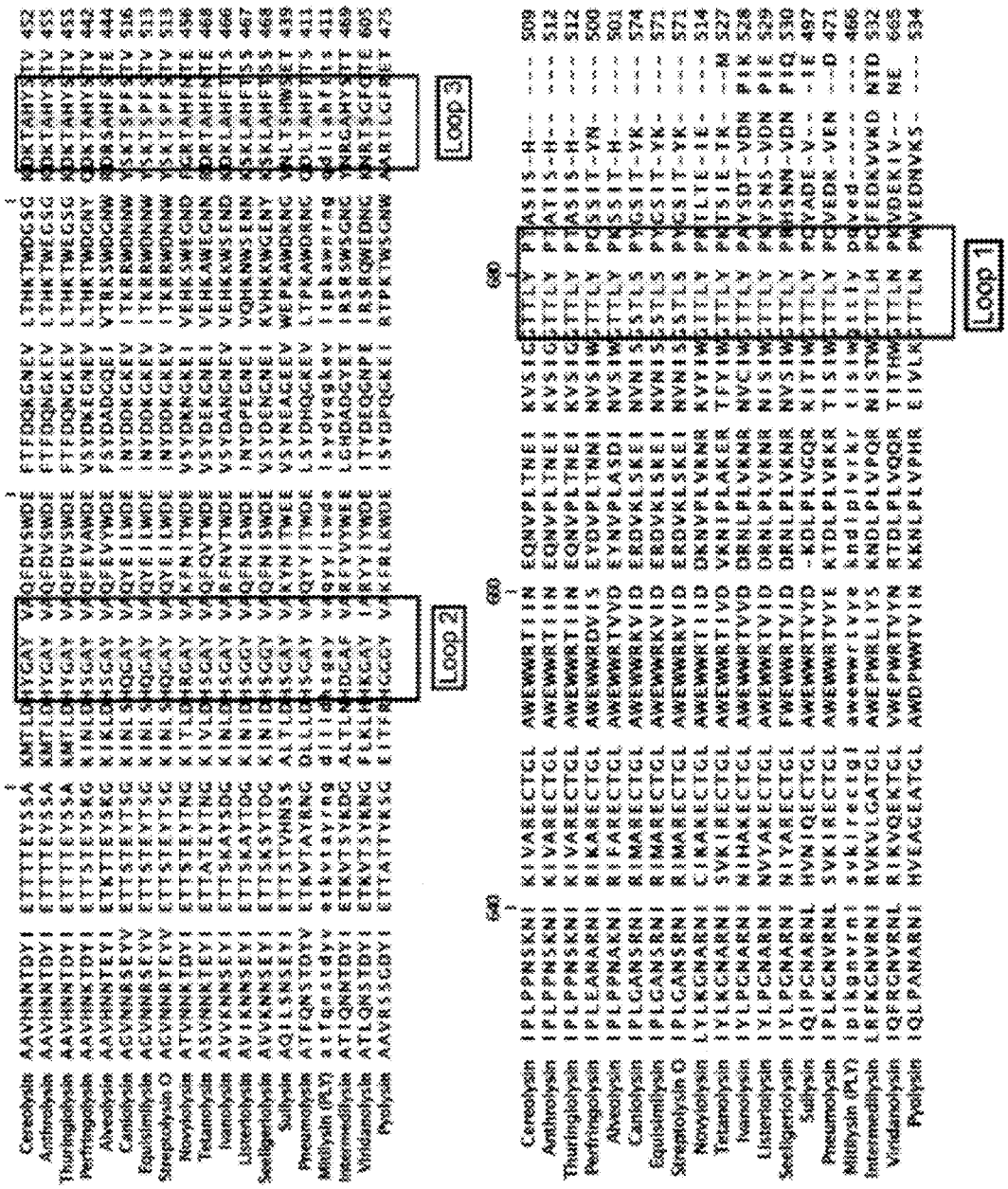

The present invention is directed in one embodiment to compositions comprising one or more non-toxic mutants of cholesterol-dependent cytolysins (CDCs). The compositions may be used in vaccines directed against corresponding disease pathogens, or may be used in diagnostic or screening methods or other analytical methods such as detection methods.

The organisms which produce the native forms of the CDCs have various pathological effects.

*Clostridium perfringens* is a causitive agent of various human and animal diseases, often characterized by enterotoxemia or soft tissue infections such as gas gangrene. Experimental evidence suggests a role for perfringolysin O in blunting the immune response by affecting neutrophil function.

*Bacillus cereus* (source of cereolysin O) is an infrequent cause of serious nongastrointestinal infection, particularly in drug addicts, the immunosuppressed, neonates, and postsurgical patients, especially when prosthetic implants such as ventricular shunts are inserted. Ocular infections are the commonest types of severe infection, including endophthalmitis, anophthalmitis, and keratitis, usually with the characteristic formation of corneal ring abscesses.

*Bacillus alvei* can cause endophthalmitis and may cause pneumonia and empyema.

*Streptococcus dysgalactiae* subsp. *Equisimilis* has been shown to be involved in many different types of human disease syndromes.

*Streptococcus canis* typically causes disease in animals, primarily dogs. It can cause disease in humans, most often soft tissue infections, bacteremia, urinary infections, bone infections or pneumonia.

*Streptococcus* causes a variety of diseases including strep throat, rheumatic fever, soft tissue infections (i.e., the fleshing eating bacteria), and many others. Streptolysin O has been shown to be a major pathogenic factor in many of these diseases.

Tetanolysin is produced by *Clostridium tetanus* that is the cause of tetanus.

*Listeria ivanovii* is an infection of animals and primarily causes abortion in sheep.

*Listeria monocytogenes* causes food borne illness in humans, the most severe is a meningitis. It is especially problematic for pregnant women where the infection may be subclinical in the mother but fatal for the fetus. Listeriolysin is a critical pathogenic factor for these diseases, without it the bacterium is avirulent.

*Streptococcus suis* is a cause of septicemia, meningitis, endocarditis, arthritis and, occasionally, other infections in pigs, and is increasingly a problem in humans, more and more outbreaks are being reported with symptoms that include high fever, malaise, nausea and vomiting, followed by nervous symptoms, subcutaneous hemorrhage, septic shock and coma.

In one embodiment, the invention comprises genetically toxoided mutants of native pneumolysin (SEQ ID NO:1) of *S. pneumoniae* (encoded by mutants of SEQ ID NO:20) that have been developed based on our extensive studies into the molecular mechanism of the cholesterol dependent cytolysins, which includes pneumolysin. These mutants exhibit several potential advantages over the current pneumolysin mutant being used for vaccine development. First, in one version, the leucine at position 460 has been mutated, for example, to an aspartate residue, and lacks the ability to bind to mammalian membranes. This mutant, therefore will not undergo any of the structural changes that normally result when these toxins bind to the membrane (as does the Pd-B mutant (Trp433Phe) described above).

In addition to mutants of pneumolysin, the present invention further comprises mutants of other CDCs which have substitutions in analogous positions in Loop 1, Loop 2 and/or Loop 3 of Domain 4, including mutants of Cereolysin (*Bacillus cereus*), Anthrolysin (*Bacillus anthracis*), Thuringiolysin (*Bacillus thuringiensis*), Perfringolysin (*Clostridium perfringens*), Alveolysin (*Bacillus alvei*), Caniolysin (*Streptococcus canis*), Equisimilysin (*Streptococcus equisimilis*), Streptolysin O (*Streptococcus pyogenes*), Tetanolysin (*Clostridium tetani*), Ivanolysin (*Listeria ivanovii*), Listeriolysin (*Listeria* monocytogenes), Seeligeriolysin (*Listeria seeligeri*), Suilysin (*Streptococcus suis*), Mitilysin (*Streptococcus mitis*), Platelet aggregation factor (a.k.a. PAF and viridanolysin) (*Streptococcus mitis*), Intermedilysin (*Streptococcus intermedius*), Pyolysin (*Arcanobacterium pyogenes*), and Novyiolysin, a.k.a., tetanolysin NT, (*Clostridium novyi*).

Wild-type amino acid sequences of Cereolysin, Anthrolysin, Thuringiolysin, (a.k.a., Thuringolysin or Cereolysin form BT), Perfringolysin, Alveolysin, Caniolysin, Equisimilysin, Streptolysin O, Novyiolysin, Tetanolysin, Ivanolysin, Listeriolysin, Seeligeriolysin, Suilysin, Mitilysin, Intermedilysin, Platelet aggregation factor (a.k.a. Viridanolysin or PAF), and Pyolysin are shown in SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19, respectively.

A variant of SEQ ID NO:18 (Platelet Aggregation Factor) which can also be mutated in accordance with the present invention is Lectinolysin, which is also obtained from *Streptococcus mitis*. The amino acid sequences of L1, L2 and L3 are the same as PAF. Lectinolysin differs from PAF at 12 positions, including 67, 158, 211, 303, 305-307, 311, 319, 327, 447 and 556 wherein in Lecinolysin the amino acids at these positions are T, D, T, H, E, N, K, N, E, K, T and I, respectively. The present invention thus contemplates mutants of Lectinolysin which are similar to those of the other mutants contemplated herein, and nucleic acids encoding these mutants, and compositions comprising these mutants.

The pneumolysin mutants contemplated herein also eliminate any toxic activity of the toxin since they cannot bind to mammalian cells. Although the currently used pneumolysin mutant (Pd-B) is about 21,000 times less toxic than native pneumolysin, it still exhibits sufficient toxicity to be problematic in the development of any vaccines that include it. It appears that modern vaccine development against *S. pneumoniae* is centered on using pneumolysin with other *S. pneumoniae* derived proteins; thus it appears that regardless of the other proteins used in the vaccine, a pneumolysin will be included in all effective vaccines against *S. pneumoniae* because of its importance to disease establishment and progression.

As described below, we have shown in perfringolysin, a toxin related to pneumolysin, that the undecapeptide of the protein does not mediate binding of these toxins to the mammalian cell, contrary to the conventional wisdom. The structures that do mediate binding are three short hydrophobic loops that are juxtaposed to the undecapeptide. We now know that if a negatively charged aspartate or glutamate residue (for example) is placed within any single hydrophobic loop (in a position not already comprising an aspartate or glutamate) binding of the CDC to the membrane is blocked. Hence, this single point mutation eliminates binding of the CDCs, including pneumolysin, to mammalian membranes. For example, a single asparate or glutamate residue substituted for leucine 460 of pneumolysin completely abrogates its hemolytic activity. Since we know in other systems (described below) that this mutation blocks binding to the membrane of cells it substantially eliminates any toxic activity (making it at least 200 times less toxic than the Pd-B mutant for example), but also eliminates any possible side effects that might be caused by its binding to the surface of mammalian membranes.

The polypeptide component preferably lacks the hemolytic activity and the pore-forming ability present in a naturally occurring *S. pneumoniae* pneumolysin protein. Generally, the polypeptide component exhibits less than 30%, 20%, 10%, 5%, or 1%, or less of the hemolytic activity of a naturally occurring *S. pneumoniae* pneumolysin protein.

The present invention also contemplates pneumolysin mutants having substitutions in several positions other than position 460 which have the same effect and include for example positions 370 and 406 of pneumolysin, as well as substitutions in one or more of three residues that flank either side of positions 370, 406 or 460, including positions 367, 368, 369, 371, 372, 373, 403, 404, 405, 407, 408, 409, 457, 458, 459, 461, 462, and 463.

For example, these residues may be substituted with a negatively-charged amino acid, glutamate, or aspartate (except in position 403, which already comprises aspartate), or a positively charged amino acid lysine, arginine, or histidine (except in positions 367 and 407, which already comprise histidine residues). Alternatively, these residues may be substituted with any other natural amino acid (including gly, ala, leu, ile, val, pro, trp, asn, gln, phe, tyr, met, cys, thr, or ser) which abrogates the binding activity, pore-forming, and hemolytic activity of the mutant.

The amino acid sequence for pneumolysin is SEQ ID NO:1 and the reverse complement of the cDNA which encodes the pneumolysin of SEQ ID NO:1 is shown as SEQ ID NO:20. The invention further comprises cDNAs of pneumolysin (and reverse complements thereof) and other mutant CDCs contemplated herein which are substituted as necessary to encode the substituted proteins (mutants) contemplated herein, and may in turn comprise any conservative base (nucleotide) substitution to make cDNAs which encode such mutants.

It will be appreciated that the polynucleotide sequences which encode the polypeptides contemplated herein may be altered with degenerate codons yet still encode the polypeptides of the invention. Accordingly the present invention further provides polynucleotides which hybridize to the polynucleotide sequences described herein (or the complement sequences thereof) having 90% identity between sequences, more preferably 95% identity, and more preferably 99% identity.

FIGS. 1A through 1E show aligned amino acid sequences of the native versions of the CDCs identified herein. The sequences are aligned along the three hydrophobic loops corresponding to positions 367-373 (second loop, L2), 403-409 (third loop, L3) and 457-463 (first loop, L1) of pneumolysin, represented in FIG. 1A-E as positions 586-592 (second loop, L2), 622-628 (third loop, L3), and 676-682 (first loop, L1). As noted above, mutants of these CDCs preferably comprise substitutions at one or more of these positions by the negatively-charged amino acids, glutamic acid, or aspartic acid (except wherein the position already has an aspartic acid), or by the positively-charged amino acids histidine, lysine or arginine (except by a histidine where the position already has a histidine, by a lysine where the position already has a lysine, or by an arginine where the position already has an arginine) or by any of the other 15 natural amino acids noted above wherein the resulting mutant functions in accordance with the present invention.

The mutants may further comprise more than one of the substitutions contemplated herein such that the mutant has 1, 2, 3, 4, 5, 6, or 7 substituted residues in a single loop (L1, L2, L3), or the mutant may have one or more (1 to 7) substituted residues in two of the loops (e.g., L1 and L2, L1 and L3, L2 and L3), or one or more substututed residues (1 to 7) in each of the three loops (L1, L2, and L3), wherein the substitutions are selected from those listed herein, for example the mutant may have 1 to 7 substitutions in the first loop (L1), and/or 1 to 7 substitutions in the second loop (L2), and/or 1 to 7 substitutions in the third loop (L3). Where the native residue is positively-charged, the substituted residue is preferably negatively-charged and where the native residue is negatively-charged, the substitute is preferably positively charged. Alternatively, aspartate may be substituted with glutamate, or histidine, arginine, or lysine or glutamate may be substituted with aspartate, lysine, histidine, or asparagine, or arginine may be substituted with a different positively-charged amino acid.

The amino acid positions of Loop 1, Loop 2 and Loop 3 of each CDC described herein is listed in Table 1.

TABLE 1

Amino Acid Positions Corresponding to Domain 4 Loops

|  | SEQ ID NO. | Loop 1 | Loop 2 | Loop 3 |
|---|---|---|---|---|
| Pneumolysin | 1 | 457-463 | 367-373 | 403-409 |
| Cereolysin | 2 | 498-504 | 408-414 | 444-450 |
| Anthrolysin | 3 | 501-507 | 411-417 | 447-453 |
| Thuringiolysin | 4 | 501-507 | 411-417 | 447-453 |
| Perfringolysin | 5 | 488-494 | 398-404 | 434-440 |
| Alveolysin | 6 | 490-496 | 400-406 | 436-442 |
| Caniolysin | 7 | 562-568 | 472-478 | 508-514 |
| Equisimilysin | 8 | 559-565 | 469-475 | 505-511 |
| Streptolysin O | 9 | 559-565 | 469-475 | 505-511 |
| Novyiolysin | 10 | 502-508 | 412-418 | 448-454 |
| Tetanolysin | 11 | 514-520 | 424-430 | 460-466 |
| Ivanolysin | 12 | 512-518 | 422-428 | 458-464 |
| Listeriolysin O | 13 | 513-519 | 423-429 | 459-465 |
| Seeligeriolysin | 14 | 514-520 | 424-430 | 460-466 |
| Suilysin | 15 | 484-490 | 395-401 | 431-437 |
| Mitilysin | 16 | 457-463 | 367-373 | 403-409 |
| Intermedilysin | 17 | 515-521 | 425-431 | 461-467 |
| PAF | 18 | 651-657 | 561-567 | 597-603 |
| Pyolysin | 19 | 521-527 | 431-437 | 467-473 |

The present invention thus comprises purified or isolated forms of the protein mutants as described herein, and antigenic fragments thereof, compositions of these mutants comprising pharmaceutically-acceptable carriers, and vaccines and sera comprising one or more of the mutants contemplated herein as well as adjuvants and immunostimulants. The mutants, or fragments thereof, can be used in analytical methods for detecting the presence of alternative forms of the proteins in biological samples using techniques known in the art, for example ELISA. The invention further comprises host cells and vectors comprising cDNAs encoding any of the mutants contemplated herein and methods of their use to produce the mutants contemplated herein.

"Purified protein" or "isolated protein" as used herein means that the protein or fragment is sufficiently free of contaminants or cell components with which the protein normally occurs as to distinguish the protein from the contaminants or cell components. It is not contemplated that "purified" necessitates having a preparation that is technically totally pure (homogeneous), but purified as used herein means the protein or polypeptide fragment is sufficiently separated from contaminants or cell components with which it normally occurs to provide the protein in a state where it can be used in an assay, such as immunoprecipitation or ELISA. For example, the purified protein can be in an electrophoretic gel.

As noted above, the invention contemplated herein is also directed to nucleic acid sequences which encode the mutant CDCs contemplated herein. The invention further contemplates nucleic acids which encode allelic variants of the protein mutants contemplated herein, wherein the allelic variants of the protein mutants differ from the protein mutants by less than 15% of their amino acid identity, for example, at least 85% of the amino acids of the allelic variant are identical to the protein mutant, and 100% of the amino acids in the first, second, and third loops (L1, L2 and L3) are identical to those in the protein mutant. More preferably the allelic variants differ from the protein mutants by less than 12% of their amino acid identity. More preferably the allelic variants differ in less than 10% of their amino acid identity. In another embodiment the allelic variants differ in less than 8% of their amino acid identity. More preferably the allelic variants differ in less than 6% of their amino acid identity, or more preferably in less than 4% of their identity, and even more preferably in less than 2% of their identity, and most preferably the allelic variants differ in less than 1% of their amino acid identity from the protein mutants described herein. Further, the present invention is directed to nucleic acids which hybridize under stringent conditions with the nucleic acids which encode the mutant CDCs described herein.

In one aspect, the CDC mutant polypeptides or proteins of the present invention comprise a sequence having at least 90%, or 95%, or 96%, or 97%, or 98%, or 99% or more % identity to the sequence presented as SEQ ID NO:1, (as determined by a sequence alignment program), and which have at least one of the mutations in Loop 1, Loop 2, or Loop 3 contemplated herein.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In another embodiment, the term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

The mutant CDCs contemplated herein may be combined with pharmaceutically-acceptable carriers or diluents. Pharmaceutically-acceptable carriers or diluents include physiological saline solutions, and buffered saline solutions at neutral pH such as phosphate buffered saline (PBS). Other types of carriers include liposomes or polymers and the like.

The pharmaceutically acceptable carrier or adjuvant in the vaccine of the present invention can be selected by standard criteria. By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier or adjuvant may depend on the method of administration and the particular patient.

Optionally, the mutant CDCs contemplated herein can be combined with an adjuvant such as Freund's incomplete adjuvant, Freund's Complete adjuvant, alum, monophosphoryl lipid A, alum phosphate or hydroxide, QS-21, salts, i.e., AlK$(SO_4)_2$, AlNa$(SO_4)_2$, AlNH$_4$$(SO_4)_2$, silica, kaolin, carbon polynucleotides, i.e., poly IC and poly AU. Preferred adjuvants include QuilA and Alhydrogel and the like. Optionally, the mutant CDCs contemplated herein can be combined with immunomodulators and immunostimulants such as interleukins, interferons and the like. Many vaccine formulations are known to those of skill in the art.

The mutant CDCs contemplated herein are added to a vaccine formulation in an amount effective to stimulate a protective immune response in an animal. Generation of a protective immune response can be measured by the development of antibodies. The amounts of the mutant CDCs contemplated herein that can form a protective immune response typically are in a unit dosage form of about 0.001 µg to 100 mg per kg of body weight, more preferably 0.01 µg to 1 mg/kg of body weight, and more preferably about 0.1 µg to about 10 µg/kg body weight, for example, at an interval of about 1 to 6 weeks intervals between immunizations.

The vaccine compositions are administered to animals which may become infected by the disease organisms described herein, including but not limited to dogs, cats, rabbits, rodents, horses, livestock (e.g., cattle, sheep, goats, and pigs), zoo animals, ungulates, primates, and humans. The preferred animal is a human.

As noted above, when the mutant is a pneumolysin mutant, the invention contemplates a vaccine which can be administered for stimulating an immunogenic response in a human subject. In addition to the one or more pneumolysin mutants, the vaccine may comprise other proteins or protein subunits from S. peumoniae, or may comprise capsular polysaccharide material combined with or conjugated to the pneumolysin mutants or other proteins in the vaccine. For example, the capsular material may be derived from any one or more of the S. pneumoniae serotypes 1, 2, 3, 4, 5, 6A, 6B, 7F, 8, 9N, 9V, 10A, 11A, 12F, 14, 15B, 17F, 18C, 19A, 19F, 20, 22F, 23F, 24F, 27, 33F, or 34, or others known in the art. As noted, the vaccine may comprise an adjuvant and/or other pharmaceutically-acceptable carriers. Polysaccharides can be conjugated to the mutant, for example, via a monomeric linkage (only one end of the polysaccharide is attached to the polypeptide), a looped linkage (a single polypeptide is attached to looped polysaccharides), or cross-linked (multiple polysaccharides attached to multiple polypeptides).

The mutant CDCs contemplated herein are also useful to form other pharmaceutical compositions, such as for causing stimulation of T-cell proliferation.

A pharmaceutical composition is formed by combining the mutant CDCs contemplated herein with a pharmaceutically (physiologically) acceptable carrier such as physiological saline, buffered saline solutions as neutral pH such as phosphate buffered saline. The preferred range of effective amounts is 100 ng to 100 mg per kg of body weight, more preferably 1 µg to 1 mg/kg body weight.

The invention also includes antigenic fragments of the mutant CDCs contemplated herein. For vaccine compositions, fragments are large enough to stimulate a protective immune response. The polypeptide component must be of a length sufficient to induce such an enhanced immune response. For fragments of a naturally occurring CDC protein, the fragments are at least 8, 10, 25, 50, 75, 100, 125, 150, 175, 200, 250, 300, 350, 400, 425, 450, 460, 465, or more amino acids in length. Fragments are peptides that are about 4 to 250 amino acids, more preferably about 10-100 amino acids.

Fragments may comprise peptide portions from different locations of the mutants joined together. Preferably, fragments include one or more of the three loops discussed herein.

The mutant CDCs contemplated herein are also useful to generate neutralizing antibodies which can be used as a passive immune serum to treat or ameliorate the symptoms in patients. A vaccine composition as described above could be administered to an animal such as a horse or a human until a neutralizing antibody response is generated. These neutralizing antibodies can then be harvested, purified, and utilized to treat patients exhibiting symptoms.

The neutralizing antibodies are administered to patients exhibiting disease symptoms in an amount effective to neutralize the effect of the pathogen. The neutralizing antibodies can be administered intravenously, intramuscularly, intradermally, subcutaneously, and the like. The preferred route is intravenously or for localized infection, topically at the site of tissue damage with debridement. It is also preferred that the neutralizing antibody be administered in conjunction with antibiotic therapy. The neutralizing antibody can be administered until a decrease in shock or tissue damage is obtained in a single or multiple dose. The preferred amount of neutralizing antibodies typically administered is about 1 mg of antibody to 1000 mg/kg, more preferably about 50-200 mg/kg of body weight.

The vaccine of the invention is preferably prepared as a pharmaceutical composition containing an immunoprotective, non-toxic amount of the protein of the invention in a non toxic and sterile pharmaceutically acceptable carrier.

The vaccines of the present invention can be administered to the appropriate subject in any manner known in the art, e.g., orally intramuscularly, intravenously, sublingual mucosal, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the conjugates. In some embodiments, the compositions can be administered via absorption via a skin patch. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained.

A pharmaceutical composition (e.g., a vaccine) is administered in an amount sufficient to elicit production of antibodies as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill.

When the vaccine is administered parenterally, via the intramuscular or deep subcutaneous route, the protein is preferably admixed or absorbed with any conventional adjuvant to attract or to enhance the immune response. Such adjuvants include but are not restricted to aluminum hydroxide, aluminum phosphate, muramyl dipeptide, bacterial lipopolysaccharides and derivatives and purified saponins from Quil A. The protein can also be presented to the immune system within microparticles such as liposomes or ISCOMs. A vaccine formulation containing the protein of the invention may be designed for oral or intranasal ingestion.

The therapeutically effective and non-toxic dose of the vaccine can be determined by a person of ordinary skill in the art. However the specific dose for any person will depend upon a variety of factors including age, general health, diet of the patient, time and route of administration, synergistic effects with other drugs being administered and whether the vaccine is administered repeatedly. If necessary the vaccine will be administered repeatedly with one to three month intervals between each dose and with an optional booster dose later in time. Actual methods of preparing the appropriate dosage forms are known, or will be apparent, to those skilled in this art; for example, see Remington's Pharmaceutical Sciences latest edition.

As noted above the present invention provides polynucleotides which encode the hereinabove described polypeptides and active fragments of the invention. The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

Shown in Table 2 are DNA sequences (and corresponding amino acid sequences) which directly encode (or encode via the reverse complement) the native sequences of the CDCs contemplated herein and thus which also may be mutated to form the mutant forms contemplated herein.

TABLE 2

Amino Acid and Nucleic Acid Sequences of Native CDC Forms

| | SEQ ID NO. (Amino Acids) | SEQ ID NO. (Nucleic Acid) |
|---|---|---|
| Pneumolysin | 1 | 20 |
| Cereolysin | 2 | 21 |
| Anthrolysin | 3 | 22 |
| Thuringiolysin | 4 | 23 |
| Perfringolysin | 5 | 24 |
| Alveolysin | 6 | 25 |
| Caniolysin | 7 | 26 |
| Equisimilysin | 8 | 27 |
| Streptolysin O | 9 | 28 |
| Novyiolysin | 10 | 29 |
| Tetanolysin | 11 | 30 |
| Ivanolysin | 12 | 31 |
| Listeriolysin O | 13 | 32 |
| Seeligeriolysin | 14 | 33 |
| Suilysin | 15 | 34 |
| Mitilysin | 16 | 35 |
| Intermedilysin | 17 | 36 |
| PAF | 18 | 37 |
| Pyolysin | 19 | 38 |

Host cells are genetically engineered (transduced or transformed or transfected) with the vectors comprising a polynucleotide encoding a polypeptide of the invention. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pBS, pD10, phagescript, psiX174, pbluescript SK, pBS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), .α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Amersham Pharmacia Biotech, Piscataway, N.J., USA) and pGEM1 (Promega, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art. However, preferred are host cells which secrete the polypeptide of the invention and permit recovery of the polypeptide from the culture media.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Procedures for the isolation of the individually expressed polypeptides may be isolated by recombinant expression/isolation methods that are well-known in the art. Typical examples for such isolation may utilize an antibody to a conserved area of the protein or to a His tag or cleavable leader or tail that is expressed as part of the protein structure.

Typically, a mutant CDC, (or allelic variant) as described herein has a derivative sequence containing at least one amino acid substitution, addition, deletion or insertion, preferably at least one substitution.

It is well-known in the art that certain amino acid substitutions may be made in protein sequences without affecting the function of the protein. Generally, conservative amino acid substitutions or substitutions of similar amino acids are tolerated without affecting protein function.

Fragments and variants of the CDC mutant proteins contemplated herein are considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that are antigenic or immunogenic in an animal, particularly a human. In his aspect, the invention includes (i) fragments of a mutant CDC, preferably at least about 20-100 amino acids in length, more preferably about 100-200 amino acids in length, and (ii) a pharmaceutical composition comprising the mutant fragment.

The term "substitution" as used herein means a replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of an isoleucine with a valine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature.

A "non-conservative substitution" refers to the substitution of an amino acid in one class with an amino acid from another class.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "nucleic acid molecule" includes RNA, DNA and cDNA molecules. It will be understood that, as a result of the degeneracy of the genetic code, a multitude of nucleotide sequences encoding a given mutant CDC protein may be produced. The present invention contemplates every possible variant nucleotide sequence, thereof, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e., promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In one embodiment, the nucleic acids contemplated herein which encode the CDC mutants described herein are hybridizable to the corresponding native sequence under high stringency hybridization conditions. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

Nucleic Acid Constructs/Expression Vectors

The nucleic acids contemplated herein may be incorporated into heterologous nucleic acid constructs or vectors, capable of introduction into, and replication in, a host cell. Any vector may be used as long as it is replicable and viable in the cells into which it is introduced. Large numbers of suitable vectors and promoters are known to those of skill in the art, and are commercially available. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Heterologous nucleic acid constructs of the present invention may include the coding sequence for the mutant CDC contemplated herein or a fragment thereof: (i) in isolation; (ii) in combination with additional coding sequences; such as fusion protein or signal peptide coding sequences, where the mutant CDC coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the mutant CDC coding sequence is a heterologous gene.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available.

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system, the beta actin promoter and the metallothionine promoter that can upregulated by addition of certain metal salts. A promoter sequence is a DNA sequence which is recognized by the host cell for expression purposes. It is operably linked the DNA sequence encoding the mutant polypeptide.

The practice of the present invention will employ, unless otherwise indicated, conventional techniques of molecular biology, microbiology, recombinant DNA, and immunology, which are within the skill of the art.

Specific embodiments of the invention will now be further described in more detail in the following non-limiting examples and it will be appreciated that additional and different embodiments of the teachings of the present invention will doubtless suggest themselves to those of skill in the art and such other embodiments are considered to have been inferred from the disclosure herein.

Figure 2:
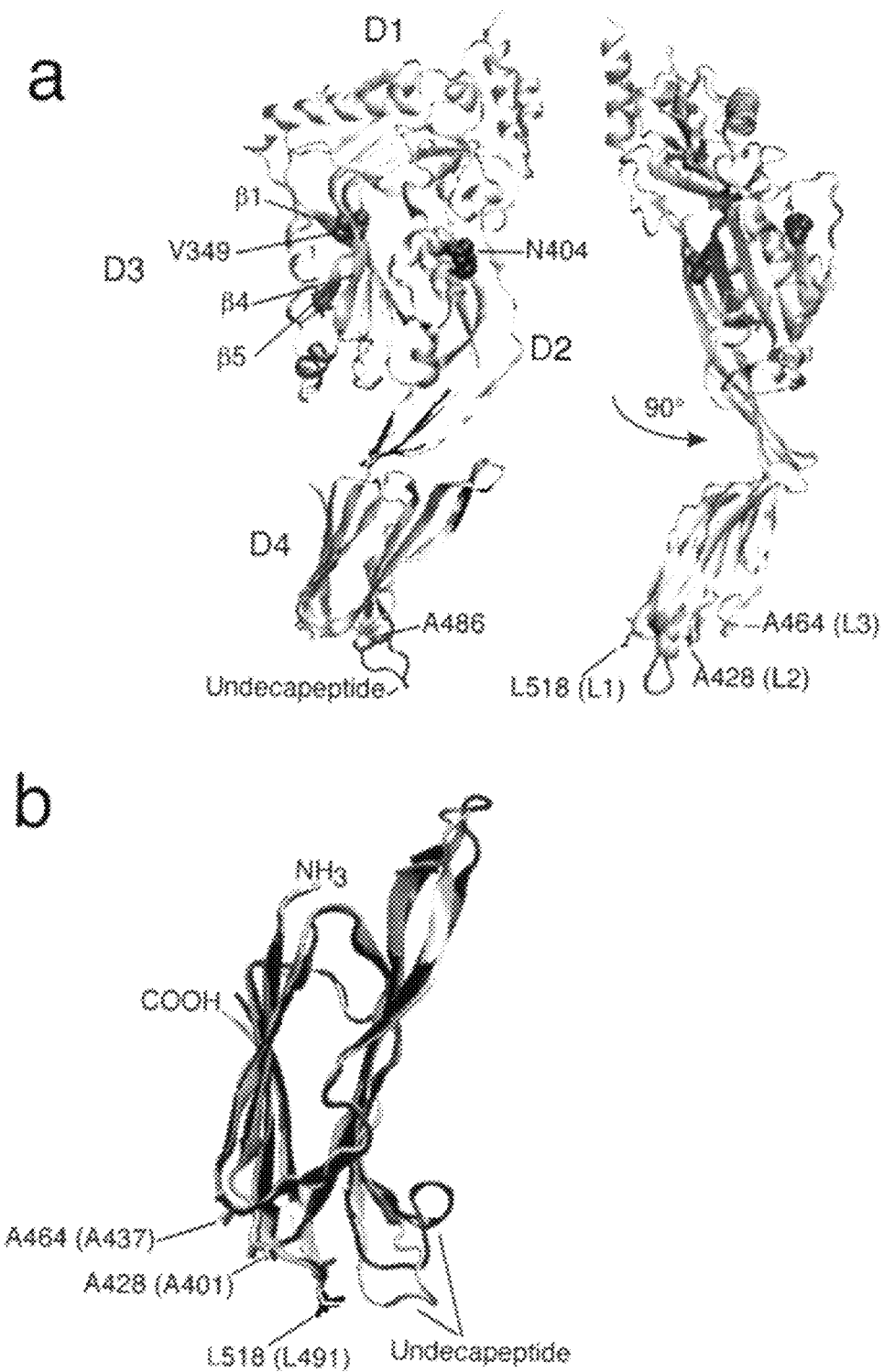

The cholesterol dependent cytolysins (CDCs) are a large family of pore-forming polypeptide toxins produced by more than 20 different species of Gram-positive bacteria (reviewed in[1]). Initially, the bacteria secrete these toxins as stable water-soluble monomers. The monomer binds to membranes and undergoes a specific sequence of structural changes, which promotes oligomerization and pore formation. As the name indicates, the CDC pore forming mechanism is absolutely dependent upon membrane cholesterol for its pore-forming mechanism. The dogma for several decades has been that cholesterol is the receptor for these toxins and that the conserved undecapeptide, located in domain 4 (D4) of the CDCs (FIG. 2), is important to the interaction of the CDCs with cholesterol[2-4]. However, other studies have suggested that the undecapeptide does not mediate the initial binding of these CDCs to cholesterol-rich membranes[5,6]. Hence, the structural components of these CDCs that mediate their binding to cholesterol have been vague prior to the present work.

The sensitivity of the CDC mechanism to oxidation has been known for over 80 years[7] and this trait was responsible for the title of "thiol-activated cytolysins" that was originally given to these toxins (reviewed in[8]). The oxidation of this thiol group results in a significant loss of cytolytic activity, often >99%[2]. It was subsequently shown via sequence analysis of a great number of the CDCs that the cysteine having the sensitive thiol group resided in the conserved undecapeptide (ECTGLAWEWWR-SEQ ID NO:39), since this is the only cysteine present in most sequenced CDCs. The loss of cytolytic activity associated oxidation of this thiol group has been suggested to result from alterations in binding to cholesterol-rich membranes[2], thus establishing a putative link between membrane binding and the undecapeptide. The highly conserved nature of the undecapeptide also suggested a highly conserved function, perhaps mediating a direct interaction with membrane cholesterol.

The dogma that cholesterol is the receptor for the CDCs was complicated by the discovery of intermedilysin (ILY), a CDC that is secreted by *Streptococcus intermedius*. In contrast to other CDCs, ILY is human cell specific[9,10], a feature that is explained by its ability to specifically bind to human CD59, a species-specific inhibitor of the complement membrane attack complex[11,12], rather than cholesterol-rich membranes[13]. Therefore, at least two classes of CDCs now exist, ILY that binds to a specific non-sterol receptor and PFO-like CDCs that bind directly to cholesterol-rich membranes. Yet, the cytolytic mechanisms of both types of CDCs are sensitive to membrane cholesterol and neither is active on membranes that are substantially depleted of cholesterol[14]. These studies, therefore, presented an enigma; does cholesterol contribute to the ILY mechanism in a significantly different way than to the PFO-like CDCs, or is there a unifying molecular basis for the contribution of cholesterol to both classes of CDCs?

Giddings et al.[14] showed that cholesterol-depletion of hRBC membranes blocked prepore to pore conversion for all CDCs, but also affected binding of PFO-like CDCs, to the membrane. Soltani et al.[15] showed that disrupting the membrane insertion of the L1-L3 D4 loops (FIG. 2) of ILY also blocks prepore to pore conversion. Therefore, two distinct phenomena block prepore to pore conversion in ILY, depletion of membrane cholesterol[14] and disruption of the membrane insertion of the L1-L3 loops[15].

Based on these observations, a detailed investigation of the interaction of the D4 loops and undecapeptide of ILY and PFO with membranes was performed. The results of these studies indicate that the L1-L3 loops at the base of domain 4 are the primary structures that recognize cholesterol-rich membranes, rather than the undecapeptide. The interaction of these loops with cholesterol-rich membranes mediates the interaction of PFO with cholesterol-rich membranes whereas their insertion into the membrane is also necessary for the prepore to pore conversion of both PFO and ILY. Hence, these results now provide the structural basis for cholesterol sensitivity of the CDCs and provide a unifying explanation for the effect of cholesterol on both ILY and PFO-like CDCs, which use different membrane receptors.

Materials and Methods

Bacterial Strains, Plasmids, and Chemicals

The genes for ILY and PFO were cloned into pTrcHisA (Invitrogen) as described previously[14,16]. All mutations were made in the native ILY (naturally cysteine-less) or the cysteine-less PFO (PFO$^{C459A}$) background. Native PFO contains a cysteine at residue 459 that has been changed to alanine to generate the cysteine-less PFO derivative PFO$^{C459A}$. Both PFO and PFO$^{C459A}$ exhibit similar cytolytic activities[16]. All chemicals and enzymes were obtained from Sigma, VWR, and Research Organics. All fluorescent probes were obtained from Molecular Probes (Invitrogen).

Generation and Purification of ILY and its Derivatives

Using PCR QuikChange mutagenesis (Stratagene), various amino acid substitutions were made in native ILY or PFO$^{C459A}$. DNA sequences of the mutant versions of the ILY gene were analyzed by the Oklahoma Medical Research Foundation Core DNA Sequencing Facility. The expression and purification of recombinant ILY and its derivatives from *Escherichia coli* were carried out as described[15,16]. The eluted protein was dialyzed into buffer (300 mM NaCl, 10 mM MES, 1 mM EDTA, pH 6.5) overnight at 4° C. The protein was then stored in 5 mM DTT and 10% (vol/vol) sterile glycerol at −80° C.

Chemical Modification of ILY and PFO and their Derivatives with Sulfhydryl Specific Reagents.

The cysteine derivatives of ILY were modified with the environmentally sensitive probe iodoaceta mido-N,N'-dimethyl-N-(7-nitrobenz-2-oxa-1,3-diazolyl)ethylene-diamine (NBD) via the sulfhydryl group. The reaction was carried out as previously described[14]. The modified protein was stored in 10% (vol/vol) sterile glycerol, quick frozen in liquid nitrogen, and stored at −80° C. Proteins were labeled at an efficiency of 75% or greater.

Fluorescence Measurements

All fluorescence intensity measurements were performed using an SLM-8100 photon counting spectrofluorimeter as previously described[16]. For NBD measurements, an excitation wavelength of 460-480 nm and an emission wavelength of 540 nm were used with a bandpass of 4 nm. Emission scans from 500-600 nm for each sample were carried out at a resolution of 1 nm with an integration time of 1 s. Samples containing 10 µg of total toxin were incubated with human red blood cell (hRBC) ghost membranes (equivalent to 303.25 µg of membrane protein) in PBS [10 mM Na$_2$HPO$_4$, 2 mM KH$_2$PO$_4$, 137 mM NaCl, 3 mM KCl (pH 7.5)] at 37° C. for 5-10 minutes before making spectral measurements.

Liposome Preparation

Liposomes containing 1-palmitoyl-2-oleoyl-sn-glycero-3-phosphocholine (POPC; Avanti Polar Lipids) and cholesterol at a ratio of 45:55 mol % were prepared as described[16].

HRBC Ghost Membrane Preparation

HRBC ghost membranes were prepared as previously described. Membrane protein content was quantified using the Bradford method (Bio-Rad Protein Assay, Bio-Rad Laboratories, Inc.) also previously described[14,16].

Cholesterol Depletion and Repletion

Cholesterol extraction was performed with methyl-β-cyclodextrin (MβCD) as previously described[14]. Briefly, human huRBC ghost membranes were incubated with a final concentration of 20 mM-40 mM MβCD (made fresh for each use) at 37° C. for 2 hours. The membranes were washed three times by repeated centrifugation (14,000 rpm for 20 min at 4° C.) and resuspended in PBS to remove excess MβCD. Ghost membranes were finally suspended in PBS. Cholesterol content was measured using Cholesterol/Cholesteryl Ester Quantitation Kit (Calbiochem). Typically the cholesterol content of the membranes was decreased>90% by this method.

Cholesterol repletion was performed using cholesterol loaded MβCD. This method has been described previously[14]. Briefly, freshly made MβCD was added to buffer A (140 mM NaCl, 5 mM KCl, 5 mM KH$_2$PO$_4$, 1 mM MgSO$_4$, 10 mM HEPES, 5 mM glucose, pH 6.5) to a final concentration of 5 mM. 100 mM stock of cholesterol was made in a 1:2 (vol/vol) of chloroform:methanol. Buffer A+MβCD was heated to 80° C. in a glass container. Once heated to 80° C., suspended cholesterol was added to a final concentration of 4 mM. The solution was homogenized by sonication (4×20 s). Then the solution was filtered using 0.22 µm filter. MβCD loaded with cholesterol was added to pelleted cholesterol depleted ghost membranes and incubated for 2 hours at 37° C. The membranes were washed by repeated centrifugation as before and finally, resuspended in PBS.

Immobilization of Liposomes on L1 SPR Sensor Chip

Surface plasmon resonance (SPR) was measured with a BIAcore 3000 system using a L1 sensor chip (BIAcore, Uppsala, Sweden). The L1 sensor chip contains a dextran matrix to which hydrophobic residues are covalently bound and has routinely been used for immobilization of liposomes. In preparation of the L1 chip for liposomes, 10 µl of 20 mM CHAPS was injected at a flow rate of 10 µl/min. Liposomes (0.5 mM final lipid concentration) were then injected at the same flow rate for 10 min. After injection of liposomes, 50 mM NaOH was injected for 3 min to remove the multiple layers of lipids. This was followed by injection of 0.1 mg/ml BSA to coat the nonspecific binding sites. All injections were performed at 25° C. The L1 chip was regenerated and striped of liposomes by repeated injections of 20 mM CHAPS and 50 mM NaOH until original RU reading was reached. The regeneration procedure did not result in loss of sensor chip binding capacity.

SPR Analysis

All analysis of interaction between the liposomes and PFO derivatives were performed in HBS at 25° C. Wild type PFO (50 ng/µl) and the PFO aspartate mutants (50 ng/µl) were injected over the liposome coated chip at a flow rate of 30 µl/min for 4 mins.

Results

Experimental strategy. ILY does not depend on membrane cholesterol to bind to native membranes, but its mechanism still remains sensitive to cholesterol. Unlike the PFO-like CDCs that do not bind to membranes that lack cholesterol, receptor binding and oligomerization of ILY still occurs on cholesterol-depleted membranes[14]. Therefore, we used ILY to first identify structures that were responsible for its cholesterol-dependence. Once we identified the structures of ILY that were sensitive to membrane cholesterol we examined the effect of disrupting these structures in PFO on its ability to bind to cholesterol-rich liposomal membranes. In this way we could determine if the same structures in both ILY and PFO were responsible for their cholesterol dependence.

Figure 3:
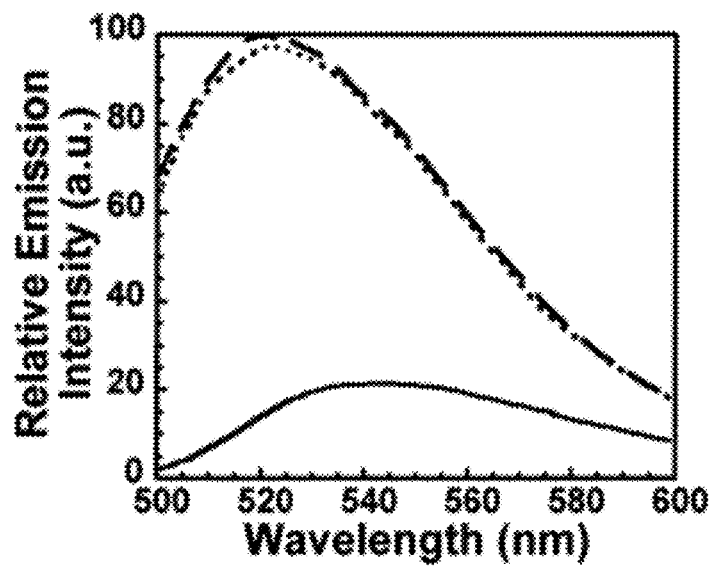

Cholesterol is not required for the membrane insertion of the ILY undecapeptide. Previous studies with ILY have shown the undecapeptide must insert into the membrane in order for the prepore to form[15]. Therefore, was its insertion sensitive to membrane cholesterol? A cysteine residue was substituted for Ala-486, which is located within the undecapeptide, and labeled with NBD via its sulfhydryl group. This residue has been shown to insert into the membrane in native ILY[15]. The fluorescence intensity of the NBD in ILY$^{A486C-NBD}$ was measured in the absence and presence of cholesterol-containing membranes or cholesterol-depleted membranes. As shown in FIG. 3, in the presence of hRBC ghost membranes, the undecapeptide inserts into the membrane as shown by the increase in fluorescence emission intensity compared to that observed for ILY in its soluble state. When the membrane is depleted of cholesterol, the same increase in fluorescence emission is observed. These results demonstrate that the membrane insertion of the undecapeptide region near Ala-486 is independent of membrane cholesterol content.

Cholesterol is required for the insertion of loops L1, L2, and L3. The membrane insertion of the three short hydrophobic loops at the tip of D4 (FIG. 2) occurs in concert and is required to anchor and properly orient the CDC monomers on the membrane[15,17]. Their insertion, in concert with the insertion of the undecapeptide is necessary for the subsequent membrane insertion of the D3 transmembrane β-hairpins (TMHs) that leads to the formation of the transmembrane β-barrel pore[15]. Cholesterol is also required for the insertion of the TMHs and formation of the pore complex[14]. Hence, both membrane cholesterol and the membrane insertion of the L1-L3 loops are prerequisites for prepore to pore conversion[14,15]. Since the membrane insertion of the L1-L3 loops precedes the insertion D3 TMHs it appeared reasonable that the depletion of membrane cholesterol may block the insertion of the L1-L3 loops that, in turn, would prevent the insertion of the D3 TMHs and block prepore to pore transition. Therefore we hypothesized that cholesterol is required for membrane insertion of the L1-L3 loops.

To test this hypothesis we individually measured the membrane insertion of the L1-L3 loops into native and cholesterol-depleted huRBC ghost membranes. We recently showed that the ILY residues Leu-518, Ala-424 and Ala-464, located within loops L1, L2, and L3, respectively, insert into the membrane[17]. To measure insertion of each loop a residue in each loop was mutated to a cysteine (ILY$^{A428C}$, ILY$^{A464C}$, ILY$^{L518C}$)[15] and the sulfhydryl group derivatized with NBD. As the NBD located at these sites enters the membrane its fluorescence emission intensity increases significantly[15,17]. The emission intensity of the NBD was compared between soluble monomeric toxin, toxin bound to huRBC ghost membranes and toxin bound to cholesterol-depleted ghost membranes.

Figure 4:
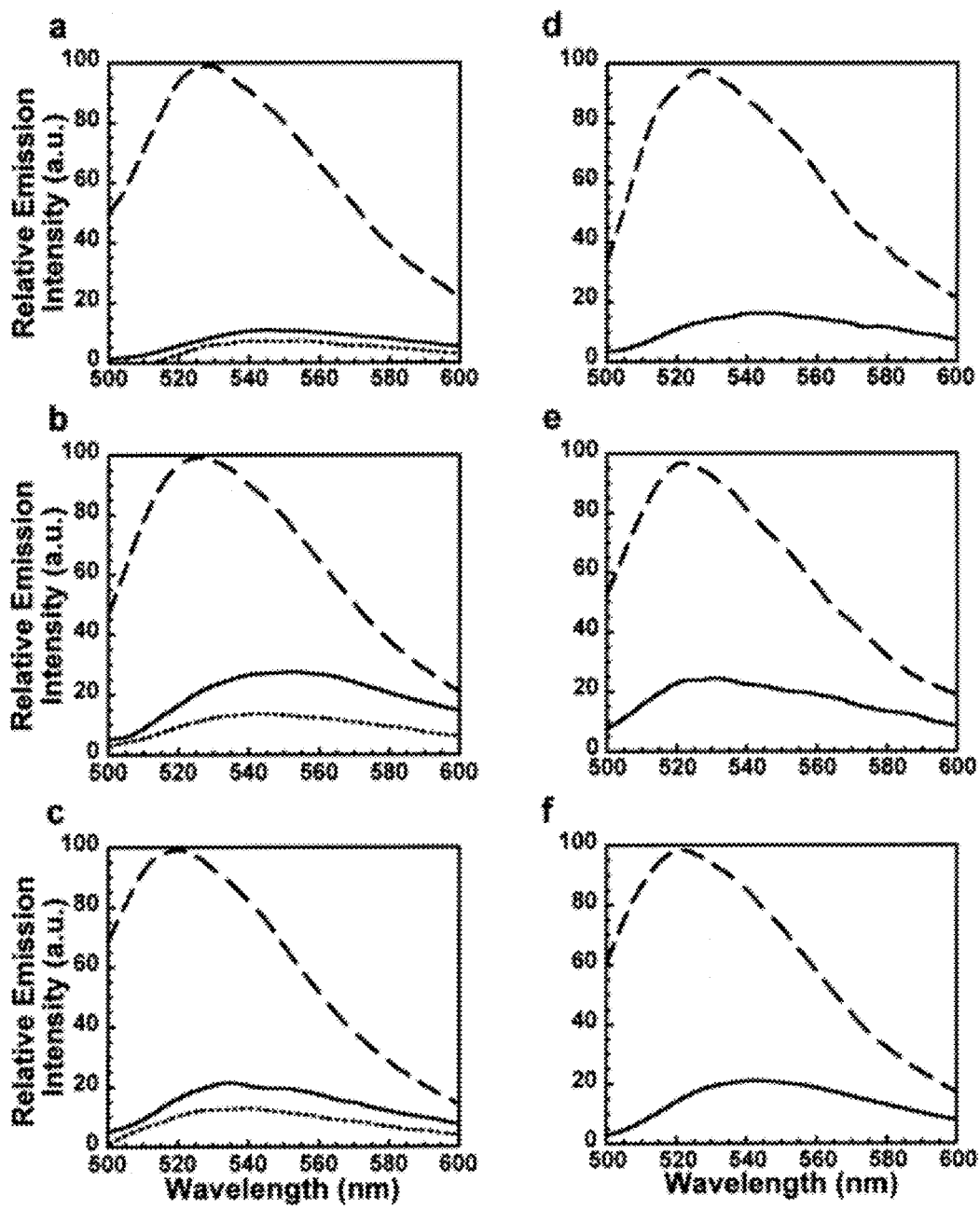

In stark contrast to the increase in fluorescence emission intensity seen when each loop inserts into the membrane of native hRBC ghosts, depletion of approximately 90% of the membrane of cholesterol abrogates the membrane insertion of all three loops (FIG. 4, panels a-c). Restoration of cholesterol to the cholesterol-depleted membranes restores the ability of the loops to insert into the membrane (FIG. 4, panels d-f)). Hence, membrane cholesterol is required for the insertion of the L1-L3 loops, and, as shown previously, this insertion is necessary for prepore to pore conversion[14,15].

Aspartate substitution of residues in loops L1-L3 of PFO prevent its binding to cholesterol-rich membranes. The membrane insertion of the L1-L3 loops of ILY was sensitive to cholesterol depletion in native membranes, suggesting that in PFO these same loops might mediate its binding directly to cholesterol-rich membranes. We could not approach this problem in PFO in a similar manner to that use with ILY since cholesterol depletion decreases the binding of PFO to the membrane. Therefore, we determined the effect of mutating these same loops on binding of PFO to cholesterol-rich liposomes. This was accomplished by the introduction of aspartate into loops L1-L3 of PFO, previously shown in ILY to prevent their insertion into the membrane[15]. The insertion of lops L1-L3 is coupled in ILY and the introduction of an asparate for any single loop residues, Ala-428 (L2), Ala-464 (L3) or Leu518 (L1), blocked their membrane insertion. We, therefore, predicted that if aspartate was substituted for any one of the analogous residues in PFO, Ala-401, Ala-437 or Leu-491, it would disrupt binding of PFO to cholesterol-rich liposomes.

Figure 5:
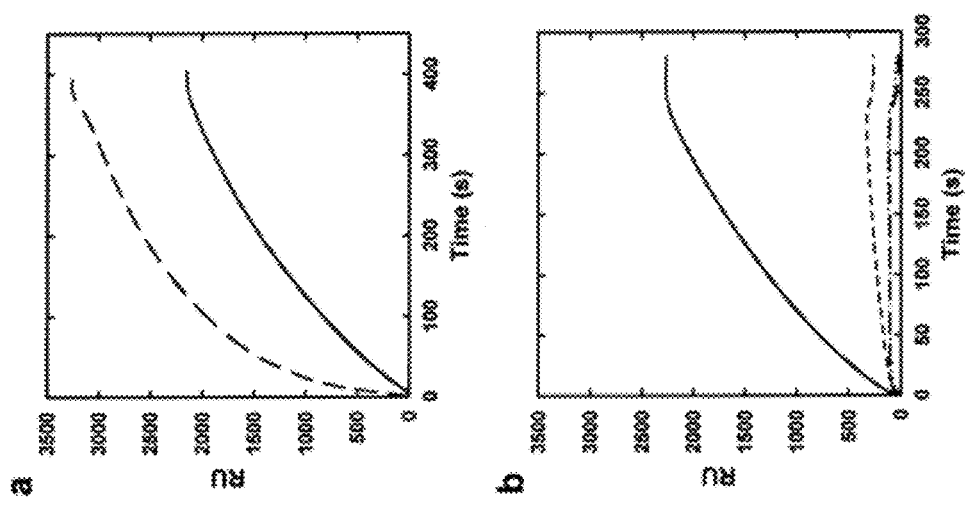

Individual substitution of the analogous residues in PFO, Ala-401 (L2), Ala-437 (L3) and Leu-491 (L1) resulted in a loss of greater than 99.7% of the hemolytic activity for each mutant (data not shown). Binding of the PFO mutants to cholesterol-PC liposomes was measured by surface plasmon resonance (SPR). As shown in FIG. 5a these mutations significantly reduced binding to cholesterol-PC liposomes when examined by SPR. Substitution of aspartate for Ala-401 (L2) or Leu-491 (L1) completely abrogated binding of PFO to the liposomes membranes and binding by the aspartate substituted Ala-437 (L3) was less than 7% that of wild type (FIG.

5b). This result indicates the D4 L1-L3 loops are critical to the interaction of PFO-like CDCs with cholesterol-rich membranes.

Modification of Cys-459 of PFO blocks the membrane insertion of the undecapeptide tryptophan residues, but not membrane binding of PFO. The conserved undecapeptide of the PFO-like CDCs has been long thought to participate in their binding to cholesterol rich membranes, primarily because chemical modification of the sulfhydryl group of the native cysteine (Cys-459) of the undecapeptide was reported to significantly impact PFO binding to low cell numbers of sheep RBCs, but not to high cell numbers[2]. Others, however, have shown that its modification does not appear to affect binding of other CDCs to cells[5,6]. Therefore, we first compared ability native PFO, and PFO modified via the sulfhydryl group of Cys-459 of the undecapeptide, to bind to cholesterol-PC liposomes via SPR.

Figure 6:
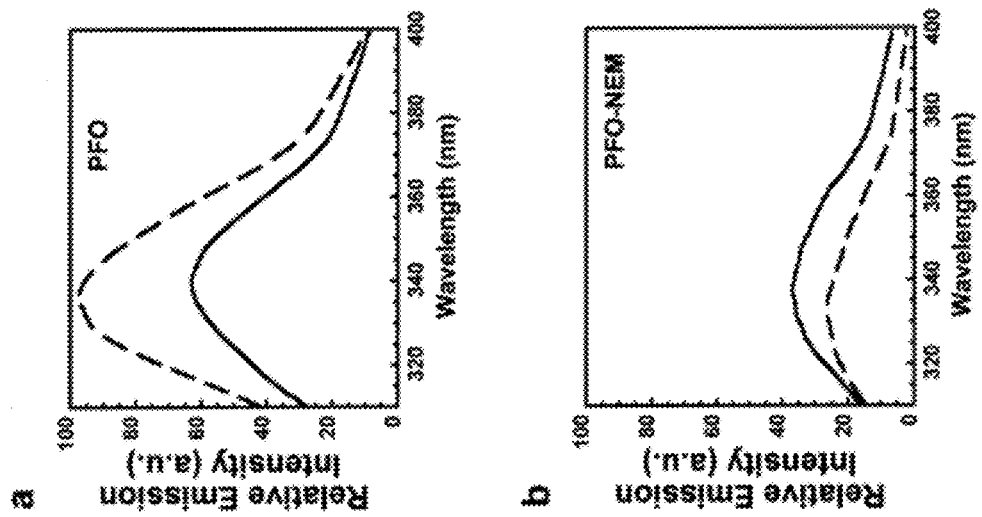

Modification of the PFO undecapeptide Cys-459 thiol with the sulfhydryl specific reagent N-ethylmaleimide (NEM) reduced the hemolytic activity 99% (data not shown), similar to other reports in which the cysteine sulfhydryl of PFO and SLO were chemically modified[2,18]. The rate and extent of binding, however, of the NEM-modified toxin was increased over that of native toxin as determined by SPR analysis (FIG. 6A-B). Therefore, chemical modification of Cys-459 did not disrupt binding of PFO to the membrane.

If modification of Cys-459 did not affect binding, what then did this modification do to PFO that effectively blocked its activity? Since the discovery of the CDCs nearly 90 years ago it has been known that their cytolytic mechanism was sensitive to oxidation. He oxidation sensitive residue was ultimately linked to the highly conserved undecapeptide cysteine residue (reviewed in[1]). We further examined the structural effects of the cysteine modification on PFO to determine if its modification prevented a structural change in PFO that could impact its activity. The membrane insertion of the undecapeptide tryptophans 464, 466 and 467 is conformationally coupled to the insertion of the D3 TMHs. Previous studies have shown that mutations in the D3 TMH1 residues that increase their rate of insertion also increase the rate of membrane insertion of the undecapeptide tryptophan residues[19]. Since Cys-459 is juxtaposed to the tryptophan residues we determined if chemical modification of the cysteine thiol group blocked the membrane insertion of the tryptophan residues.

The membrane insertion of the undecapeptide tryptophan residues can be monitored by the increase in their intrinsic fluorescence intensity as they move into the nonpolar environment of the membrane[20,21]. The insertion of these tryptophans was measured in the NEM-modified and native PFO (FIGS. 6a and 6b). The modification of Cys-459 blocked the insertion of the undecapeptide tryptophans, but did not prevent it from forming an SDS-resistant oligomer, similar to native PFO (data not shown). Hence, these data show that the conformational change in the PFO structure that is reflected by the loss of the insertion of the undecapeptide tryptophan residues affects the subsequent conversion of the prepore oligomer to the pore complex.

Immunization with Pneumolysin Mutant Leu 460Asp

Figure 7:
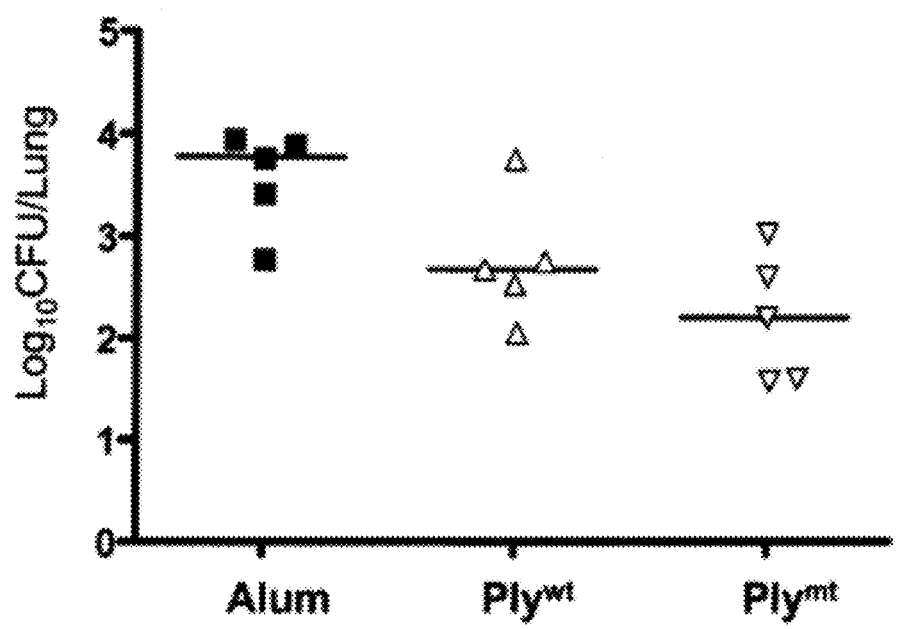

CBA/CAHN-XID mice were immunized subcutaneously with 5 μg of pneumolysin or pneumolysin mutant using alum (aluminum hydroxide) as the adjuvant on days 0 and 14. On day 21 the mice were immunized with the proteins in diluent alone (no adjuvant). All injections were given in 0.2 ml volume. On day 35 mice were challenged with capsular type 19F strain EF3030. Seven days later the mice were euthanized with carbon dioxide gas. The lungs were homogenized and the numbers of colony forming units (CFU) in the lungs of each mouse was determined by plating the homogenized tissue on blood agar plates. The mice were also bled. No pneumococci were observed in the blood demonstrating that this is a model of pneumonia and not pneumonia and sepsis. The results show that both wild-type and the mutant pneumolysin are able to protect against pneumonia in a focal pneumonia model in mice (FIG. 7).

Two long-standing hallmarks of the CDCs are the dependence of their pore-forming mechanism on the presence of membrane cholesterol and the reversible inactivation of most CDCs by oxidation of the undecapeptide cysteine. The studies herein resolve the molecular basis for both phenomena. Without wishing to be bound by theory, the membrane insertion of the L1-L3 loops, located at the base of domain 4, appears to be the primary event that is sensitive to the presence of membrane cholesterol for ILY. Upon cholesterol depletion these loops do not insert into the membrane and as shown previously cholesterol extraction from hRBC membranes[15] prevent the prepore to pore conversion of ILY. Our results indicate that both effects also result from the inability of these loops to insert into cholesterol-depleted membranes. Our data further indicate that the oxidation of the conserved cysteine in PFO, and presumably other PFO-like CDCs, blocks the membrane insertion of the tryptophan residues that traps PFO in a prepore state, but does not affect binding to cholesterol-rich liposomes.

The discovery of ILY, a human cell specific toxin, presented a conundrum; how could ILY discriminate between human and animal cells if cholesterol was its receptor? The human cell specificity of ILY was explained by the discovery that human CD59, a late stage, species-specific complement inhibitor, was its receptor[13]. Even though cholesterol was not the ILY receptor, its pore-forming mechanism remained sensitive to membrane cholesterol[14] showed that cholesterol was required for a much later stage of the pore-forming mechanism in ILY; substantial depletion of membrane cholesterol blocked prepore to pore conversion. Interestingly, this was also observed for SLO and PFO[14], two CDCs that can bind directly to cholesterol-rich membranes. Although depletion of membrane cholesterol from hRBCs blocked prepore to pore conversion of PFO, it also decreased PFO binding. Therefore, cholesterol is necessary for prepore to pore conversion for all three CDCs and in addition it also contributes to membrane binding by the PFO-like CDCs.

Recently Soltani et al.[15] showed that the membrane insertion of the L1-L3 D4 loops of ILY is necessary for prepore to pore conversion. Hence, both cholesterol and membrane insertion of the L1-L3 loops were necessary for prepore to pore conversion of ILY. Without wishing to be bound by theory, the data presented herein indicates that a unifying explanation for these observations is that the membrane insertion of these loops only occurs in cholesterol-rich membranes, and this insertion is necessary for the prepore to pore conversion of both ILY and PFO-like CDCs. In addition, the ability of these loops to insert into cholesterol-rich membranes also mediates the initial binding of PFO, and presumably the PFO-like CDCs, to cholesterol-rich membrane surfaces. Therefore, these data indicate that in both ILY and PFO-like CDCs, the L1-L3 loops must insert into the membrane in order for the successful formation of the pore complex. In the case of ILY, binding is mediated first by huCD59 followed by the insertion of the L1-L3 loops into cholesterol-rich membranes, whereas these two events, binding and insertion, are one and the same in PFO and are mediated primarily by the L1-L3 loops.

It has been traditionally accepted that the undecapeptide of the PFO-like CDCs contributed or directly mediated the recognition of cholesterol-rich membranes[2,3,21]. The studies herein indicate that the L1-L3 loops are the primary structures that mediate the interaction between the CDCs and cholesterol-rich membranes. Although chemical modification of the PFO undecapeptide cysteine with NEM decreases its hemolytic activity by more than 99%, its binding to cholesterol-PC liposomes is largely unimpaired. Hence, in contrast to existing dogma, the interaction of PFO, and other PFO-like CDCs, is primarily mediated by loops L1-L3 and not the undecapeptide. Mutations within the undecapeptide could influence the interaction of L1-L3 with cholesterol rich membranes. We have shown that mutation of undecapeptide Trp-491 of ILY blocks the insertion of L1-L3[15] and the altered structure of the native ILY undecapeptide apparently prevents the direct interaction of L1-L3 with cholesterol-rich membranes, thus allowing it to first bind to huCD59. This latter idea is reinforced by the fact that when the consensus undecapeptide structure was introduced into ILY it enabled it to bind to nonhuman cells[22].

Why don't the L1-L3 loops of ILY mediate binding to cholesterol rich membranes similar to PFO? As suggested above it appears that the major difference in domain 4 between is the primary structure of the highly conserved undecapeptide. It is clear that ILY has lost the ability to bind directly to cholesterol-rich membranes, otherwise it would not exhibit the human cell specificity mediated via huCD59. The crystal structures of D4 of ILY and PFO may provide an explanation for this difference in the L1-L3 loops to mediate direct binding of these two CDCs to cholesterol-rich membranes. The location and orientation of L1-L3 residues (Leu-518, Ala-428, and Ala-464) of ILY are nearly identical to the analogous residues in PFO (Leu-491, Ala-401, and Ala-437) (FIG. 4b). In fact, the majority of the D4 structure of the two CDCs is nearly identical (rms deviation of less than 0.6 Å,[23]) with the exception of the undecapeptide loop and a β-tongue structure at the top of domain 4. The undecapeptide loop of ILY extends down from the base of D4 4-5 Å further than the PFO undecapeptide. Hence, the ILY undecapeptide may sterically hinder the interaction of the L1-L3 loops of ILY with the cholesterol-rich surface. Perhaps only after binding to receptor is the ILY undecapeptide structure altered in such a way to permit the insertion of the L1-L3 loops.

We have provided a structural basis for the severe effect on activity that oxidation of the undecapeptide cysteine exhibits on the cytolytic mechanism of PFO, and presumably other PFO-like CDCs. Originally the CDCs were termed the thiol-activated cytolysins due to this feature, but the molecular basis for this effect was unknown. Early studies suggested that binding to RBCs was affected, but at the same time binding to cholesterol was unaffected and nonlytic oligomers were still observed on the surface the cells[2]. As shown herein this modification prevents the insertion of the undecapeptide tryptophans and results in a prepore-trapped oligomeric structure. Although the precise structural basis for this effect is not known, previous studies have shown that the membrane insertion of the domain 3 TMHs, that form the transmembrane â-barrel pore, is conformationally coupled to the membrane insertion of the domain 4 undecapeptide tryptophan residues[19]. Hence, preventing the membrane insertion of these tryptophans may prevent the insertion of the domain 3 TMHs, thus trapping PFO in the prepore state.

In summary, these studies have provided a structural basis for the two main hallmarks of the CDCs, the sensitivity to the presence of membrane cholesterol and to oxidation of the undecapeptide cysteine thiol.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, compositions of matter, means, methods and steps described in the specification particularly in regard to the specific amino acid or nucleic acid sequences described or contemplated herein. As one of ordinary skill in the art will readily appreciate from the disclosure of the present invention, processes, compositions of matter, means, methods, sequences, or steps, presently existing or later to be developed that perform substantially the same function or achieve substantially the same result as the corresponding embodiments described herein may be utilized according to the present invention. Accordingly, the appended claims are intended to include within their scope such processes, compositions of matter, means, methods, amino acid or nucleic acid sequences, or steps.

All patents, patent applications, articles and publications mentioned herein, are hereby expressly incorporated herein by reference in their entireties.

REFERENCES

1. Alouf, J. E., Billington, S. J. & Jost, B. H. Repertoire and general features of the cholesterol-dependent cytolysins in *Bacterial Toxins: A Comprehensive Sourcebook* (eds. Alouf, J. E. & Popoff, M. R.) 643-658 (Academic Press, London, 2005).
2. Iwamoto, M., Ohno-Iwashita, Y. & Ando, S. Role of the essential thiol group in the thiol-activated cytolysin from *Clostridium perfringens. Eur J Biochem* 167, 425-430 (1987).
3. Sekino-Suzuki, N., Nakamura, M., Mitsui, K. I. & Ohno-Iwashita, Y. Contribution of individual tryptophan residues to the structure and activity of theta-toxin (perfringolysin o), a cholesterol-binding cytolysin. *Eur J Biochem* 241, 941-947 (1996).
4. Jacobs, T. et al. The conserved undecapeptide shared by thiol-activated cytolysins is involved in membrane binding. *FEBS Lett.* 459, 463-466 (1999).
5. Vazquez-Boland, J. A., Dominguez, L., Rodriguez-Ferri, E. F., Fernandez-Garayzabal, J. F. & Suarez, G. Preliminary evidence that different domains are involved in cytolytic activity and receptor (cholesterol) binding in listeriolysin O, the *Listeria monocytogenes* thiol-activated toxin. *FEMS Microbiol Lett* 53, 95-9 (1989).
6. Saunders, F. K., Mitchell, T. J., Walker, J. A., Andrew, P. W. & Boulnois, G. J. Pneumolysin, the thiol-activated toxin of *Streptococcus pneumoniae*, does not require a thiol group for in vitro activity. *Infect. Immun.* 57, 2547-2552 (1989).
7. Neill, J. M. & Fleming, W. L. Studies on the oxidation and reduction of immunological substances: II The hematoxin of the Welch bacillus. *J. Exp. Med.* 44, 215-226 (1926).
8. Alouf, J. E. & Geoffrey, C. Structure activity relationships in the sulfhydryl-activated toxins. In *Bacterial Protein Toxins* (eds. Alouf, J. E., Fehrenbach, F. J., Freer, J. H. & Jeljaszewicz, J.) 165-171 (Academic Press, London, 1984).
9. Nagamune, H. et al. Intermedilysin. A cytolytic toxin specific for human cells of a *Streptococcus intermedius* isolated from human liver abscess. *Adv Exp Med Biol* 418, 773-775 (1997).
10. Nagamune, H. et al. Intermedilysin, a novel cytotoxin specific for human cells secreted by *Streptococcus inter-*

*medius* UNS46 isolated from a human liver abscess. *Infect Immun* 64, 3093-3100 (1996).
11. Rollins, S. A., Zhao, J., Ninomiya, H. & Sims, P. J. Inhibition of homologous complement by CD59 is mediated by a species-selective recognition conferred through binding to C8 within C5b-8 or C9 within C5b-9. *J Immunol* 146, 2345-51 (1991).
12. Rollins, S. A. & Sims, P. J. The complement-inhibitory activity of CD59 resides in its capacity to block incorporation of C9 into membrane C5b-9. *J Immunol* 144, 3478-83 (1990).
13. Giddings, K. S., Zhao, J., Sims, P. J. & Tweten, R. K. Human CD59 is a receptor for the cholesterol-dependent cytolysin intermedilysin. *Nat Struct Mol Biol* 12, 1173-1178 (2004).
14. Giddings, K. S., Johnson, A. E. & Tweten, R. K. Redefining cholesterol's role in the mechanism of the cholesterol-dependent cytolysins. *Proc Natl Acad Sci USA* 100, 11315-11320 (2003).
15. Soltani, C. E., Hotze, E. M., Johnson, A. E. & Tweten, R. K. Specific protein-membrane contacts are required for prepore and pore assembly by a cholesterol-dependent cytolysin. *J. Biol. Chem*. Paper is press 282 (21), 15709-15716, Apr. 5, 2007.
16. Shepard, L. A. et al. Identification of a membrane-spanning domain of the thiol-activated pore-forming toxin *Clostridium perfringens* perfringolysin O: an á-helical to á-sheet transition identified by fluorescence spectroscopy. *Biochemistry* 37, 14563-14574 (1998).
17. Ramachandran, R., Heuck, A. P., Tweten, R. K. & Johnson, A. E. Structural insights into the membrane-anchoring mechanism of a cholesterol-dependent cytolysin. *Nat Struct Biol* 9, 823-7 (2002).
18. Harris, J. R., Adrian, M., Bhakdi, S. & Palmer, M. Cholesterol-Streptolysin O Interaction: An EM Study of Wild-Type and Mutant Streptolysin O. *J Struct Biol* 121, 343-55 (1998).
19. Heuck, A. P., Hotze, E., Tweten, R. K. & Johnson, A. E. Mechanism of membrane insertion of a multimeric b-barrel protein: Perfringolysin O creates a pore using ordered and coupled conformational changes. *Molec. Cell* 6, 1233-1242 (2000).
20. Heuck, A. P., Tweten, R. K. & Johnson, A. E. Assembly and topography of the prepore complex in cholesterol-dependent cytolysins. *J Biol Chem* 278, 31218-31225 (2003).
21. Nakamura, M., Sekino, N., Iwamoto, M. & Ohno-Iwashita, Y. Interaction of theta-toxin (perfringolysin O), a cholesterol-binding cytolysin, with liposomal membranes: change in the aromatic side chains upon binding and insertion. *Biochemistry* 34, 6513-6520 (1995).
22. Nagamune, H. et al. The human-specific action of intermedilysin, a homolog of streptolysin o, is dictated by domain 4 of the protein. *Microbiol Immunol* 48, 677-92 (2004).
23. Polekhina, G., Giddings, K. S., Tweten, R. K. & Parker, M. W. Insights into the action of the superfamily of cholesterol-dependent cytolysins from studies of intermedilysin. *Proc Natl Acad Sci* 102, 600-605 (2005).
24. Rossjohn, J., Feil, S. C., McKinstry, W. J., Tweten, R. K. & Parker, M. W. Structure of a cholesterol-binding thiol-activated cytolysin and a model of its membrane form. *Cell* 89, 685-692 (1997).
25. Humphrey, W., Dalke, A. & Schulten, K. VMD: visual molecular dynamics. *J Mol Graph* 14, 33-8, 27-8 (1996).
26. Anonymous: Prevention of Pneumococcol Disease: Recommendations of the Advisory Committee on Immunization Practices (ACIP). Morbidity and Mortality Weekly Report-Recommendations and Reports: 46:1-24 (Apr. 4, 1997).

What is claimed is:

1. A purified polypeptide comprising an amino acid sequence that is at least 90% identical to SEQ ID NO:9, and comprises an amino acid substitution in at least one of amino acid positions 561 and 562.

2. The purified polypeptide of claim 1, wherein the amino acid substitution is in amino acid position 561.

3. A composition comprising the purified polypeptide of claim 1, and a pharmaceutically-acceptable carrier, adjuvant, diluent, and/or vehicle.

4. The purified polypeptide of claim 1, wherein the amino acid sequence is at least 95% identical to SEQ ID NO:9.

5. The purified polypeptide of claim 1, wherein the amino acid sequence is at least 96% identical to SEQ ID NO:9.

6. The purified polypeptide of claim 1, wherein the amino acid sequence is at least 97% identical to SEQ ID NO:9.

7. The purified polypeptide of claim 1, wherein the amino acid sequence is at least 98% identical to SEQ ID NO:9.

8. The purified polypeptide of claim 1, wherein the amino acid sequence is at least 99% identical to SEQ ID NO:9.

9. The purified polypeptide of claim 1, wherein the amino acid substitution is in amino acid position 562.

10. The purified polypeptide of claim 1, comprising amino acid substitutions in both amino acid positions 561 and 562.

11. A composition comprising:
one or more of the polypeptides of claim 1; and
a pharmaceutically-acceptable carrier, vehicle, adjuvant, and/or diluent.

* * * * *

UNITED STATES PATENT AND TRADEMARK OFFICE
CERTIFICATE OF CORRECTION

PATENT NO.        : 9,228,001 B2               Page 1 of 1
APPLICATION NO.   : 13/401460
DATED             : January 5, 2016
INVENTOR(S)       : Rodney K. Tweten It is certified that error appears in the above-identified patent and that said Letters Patent is hereby corrected as shown below:

In the Specification:
Column 5, line 27: Before "(b)," insert -- (a), $ILY^{A464C-NDB}$ --

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 39

<210> SEQ ID NO 1
<211> LENGTH: 471
<212> TYPE: PRT
<213> ORGANISM: Streptococcus pneumoniae

<400> SEQUENCE: 1

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125
```

-continued

```
Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 2
<211> LENGTH: 509
<212> TYPE: PRT
<213> ORGANISM: Bacillus cereus

<400> SEQUENCE: 2

Met Asn Ile Lys Lys Asn Thr Lys Arg Arg Lys Phe Leu Ala Cys Leu
1               5                   10                  15

Leu Val Ser Leu Cys Thr Ile Asn Tyr Ser Ser Ile Ser Phe Ala Glu
            20                  25                  30
```

Thr Gln Ala Ser Asn Ala Thr Asp Val Thr Lys Asn Ala Ser Gly Ile
            35                  40                  45

Asp Thr Gly Ile Ala Asn Leu Lys Tyr Asn Asn Gln Glu Val Leu Ala
        50                  55                  60

Val Asn Gly Asp Lys Val Glu Ser Phe Val Pro Lys Glu Ser Ile Asn
65                  70                  75                  80

Ser Asn Gly Lys Phe Val Val Glu Arg Glu Lys Lys Ser Leu Thr
                85                  90                  95

Thr Ser Pro Val Asp Ile Ser Ile Asp Ser Val Val Asn Arg Thr
                100                 105                 110

Tyr Pro Gly Ala Val Gln Leu Ala Asn Lys Ala Phe Ala Asp Asn Gln
                115                 120                 125

Pro Ser Leu Leu Val Ala Lys Arg Lys Pro Leu Asn Ile Ser Ile Asp
        130                 135                 140

Leu Pro Gly Met Arg Lys Glu Asn Thr Ile Thr Val Gln Asn Pro Thr
145                 150                 155                 160

Tyr Gly Asn Val Ala Gly Ala Val Asp Asp Leu Val Ser Thr Trp Asn
                165                 170                 175

Glu Lys Tyr Ser Thr Thr His Thr Leu Pro Ala Arg Met Gln Tyr Thr
                180                 185                 190

Glu Ser Met Val Tyr Ser Lys Ser Gln Ile Ala Ser Ala Leu Asn Val
        195                 200                 205

Asn Ala Lys Tyr Leu Asp Asn Ser Leu Asn Ile Asp Phe Asn Ala Val
        210                 215                 220

Ala Asn Gly Glu Lys Lys Val Met Val Ala Ala Tyr Lys Gln Ile Phe
225                 230                 235                 240

Tyr Thr Val Ser Ala Glu Leu Pro Asn Asn Pro Ser Asp Leu Phe Asp
                245                 250                 255

Asn Ser Val Thr Phe Asp Glu Leu Thr Arg Lys Gly Val Ser Asn Ser
            260                 265                 270

Ala Pro Pro Val Met Val Ser Asn Val Ala Tyr Gly Arg Thr Ile Tyr
            275                 280                 285

Val Lys Leu Glu Thr Thr Ser Lys Ser Lys Asp Val Gln Ala Ala Phe
        290                 295                 300

Lys Ala Leu Leu Lys Asn Asn Ser Val Glu Thr Ser Gly Gln Tyr Lys
305                 310                 315                 320

Asp Ile Phe Glu Glu Ser Thr Phe Thr Ala Val Val Leu Gly Gly Asp
                325                 330                 335

Ala Lys Glu His Asn Lys Val Val Thr Lys Asp Phe Asn Glu Ile Arg
            340                 345                 350

Asn Ile Ile Lys Asp Asn Ala Glu Leu Ser Leu Lys Asn Pro Ala Tyr
            355                 360                 365

Pro Ile Ser Tyr Thr Ser Thr Phe Leu Lys Asp Asn Ser Thr Ala Ala
        370                 375                 380

Val His Asn Asn Thr Asp Tyr Ile Glu Thr Thr Thr Thr Glu Tyr Ser
385                 390                 395                 400

Ser Ala Lys Met Thr Leu Asp His Tyr Gly Ala Tyr Val Ala Gln Phe
                405                 410                 415

Asp Val Ser Trp Asp Glu Phe Thr Phe Asp Gln Lys Gly Asn Glu Val
            420                 425                 430

Leu Thr His Lys Thr Trp Asp Gly Ser Gly Lys Asp Lys Thr Ala His
            435                 440                 445

```
Tyr Ser Thr Val Ile Pro Leu Pro Asn Ser Lys Asn Ile Lys Ile
        450                 455                 460

Val Ala Arg Glu Cys Thr Gly Leu Ala Trp Glu Trp Trp Arg Thr Ile
465                 470                 475                 480

Ile Asn Glu Gln Asn Val Pro Leu Thr Asn Glu Ile Lys Val Ser Ile
                485                 490                 495

Gly Gly Thr Thr Leu Tyr Pro Thr Ala Ser Ile Ser His
                500                 505

<210> SEQ ID NO 3
<211> LENGTH: 512
<212> TYPE: PRT
<213> ORGANISM: Bacillus anthracis

<400> SEQUENCE: 3

Met Ile Phe Leu Asn Ile Lys Lys Asn Thr Lys Arg Arg Lys Phe Leu
1               5                   10                  15

Ala Cys Leu Leu Val Ser Leu Cys Thr Ile His Tyr Ser Ser Ile Ser
            20                  25                  30

Phe Ala Glu Thr Gln Ala Gly Asn Ala Thr Gly Ala Ile Lys Asn Ala
        35                  40                  45

Ser Asp Ile Asn Thr Gly Ile Ala Asn Leu Lys Tyr Asp Ser Arg Asp
    50                  55                  60

Ile Leu Ala Val Asn Gly Asp Lys Val Glu Ser Phe Ile Pro Lys Glu
65                  70                  75                  80

Ser Ile Asn Ser Asn Gly Lys Phe Val Val Glu Arg Glu Lys Lys
                85                  90                  95

Ser Leu Thr Thr Ser Pro Val Asp Ile Leu Ile Asp Ser Val Val
            100                 105                 110

Asn Arg Thr Tyr Pro Gly Ala Val Gln Leu Ala Asn Lys Ala Phe Ala
        115                 120                 125

Asp Asn Gln Pro Ser Leu Leu Val Ala Lys Arg Lys Pro Leu Asn Ile
130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
                165                 170                 175

Thr Trp Asn Glu Lys Tyr Ser Thr Thr His Thr Leu Pro Ala Arg Met
            180                 185                 190

Gln Tyr Thr Glu Ser Met Val Tyr Ser Lys Ser Gln Ile Ala Ser Ala
        195                 200                 205

Leu Asn Val Asn Ala Lys Tyr Leu Asp Asn Ser Leu Asn Ile Asp Phe
    210                 215                 220

Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
            260                 265                 270

Ser Asn Ser Ala Pro Pro Val Met Val Ser Asn Val Ala Tyr Gly Arg
        275                 280                 285

Thr Val Tyr Val Lys Leu Glu Thr Thr Ser Lys Ser Lys Asp Val Gln
    290                 295                 300

Ala Ala Phe Lys Ala Leu Leu Lys Asn Asn Ser Val Glu Thr Ser Gly
305                 310                 315                 320
```

```
Gln Tyr Lys Asp Ile Phe Glu Ser Thr Phe Thr Ala Val Val Leu
            325                 330                 335

Gly Gly Asp Ala Lys Glu His Asn Lys Val Val Thr Lys Asp Phe Asn
        340                 345                 350

Glu Ile Arg Asn Ile Ile Lys Asp Asn Ala Glu Leu Ser Phe Lys Asn
            355                 360                 365

Pro Ala Tyr Pro Ile Ser Tyr Thr Ser Thr Phe Leu Lys Asp Asn Ala
        370                 375                 380

Thr Ala Ala Val His Asn Asn Thr Asp Tyr Ile Glu Thr Thr Thr Thr
385                 390                 395                 400

Glu Tyr Ser Ser Ala Lys Met Thr Leu Asp His Tyr Gly Ala Tyr Val
            405                 410                 415

Ala Gln Phe Asp Val Ser Trp Asp Glu Phe Thr Phe Asp Gln Asn Gly
        420                 425                 430

Lys Glu Val Leu Thr His Lys Thr Trp Glu Gly Ser Gly Lys Asp Lys
            435                 440                 445

Thr Ala His Tyr Ser Thr Val Ile Pro Leu Pro Pro Asn Ser Lys Asn
        450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
            485                 490                 495

Val Ser Ile Gly Gly Thr Thr Leu Tyr Pro Thr Ala Thr Ile Ser His
        500                 505                 510

<210> SEQ ID NO 4
<211> LENGTH: 509
<212> TYPE: PRT
<213> ORGANISM: Bacillus thuringiensis

<400> SEQUENCE: 4

Met Asn Ile Lys Lys Asn Thr Lys Arg Arg Lys Phe Leu Ala Cys Leu
1               5                   10                  15

Leu Val Ser Leu Cys Thr Ile Asn Tyr Ser Ser Ile Ser Phe Ala Glu
            20                  25                  30

Thr Gln Ala Ser Asn Ala Thr Asp Val Thr Lys Asn Ala Ser Gly Ile
        35                  40                  45

Asp Thr Gly Ile Ala Asn Leu Lys Tyr Asn Ile Gln Glu Val Leu Ala
    50                  55                  60

Val Asn Gly Asp Lys Val Glu Ser Phe Val Pro Lys Glu Ser Ile Asn
65                  70                  75                  80

Ser Asn Gly Lys Phe Val Val Glu Arg Glu Lys Lys Ser Leu Thr
            85                  90                  95

Thr Ser Pro Val Asp Ile Ser Ile Asp Ser Val Val Asn Arg Thr
        100                 105                 110

Tyr Pro Gly Ala Val Gln Leu Ala Asn Lys Ala Phe Ala Asp Asn Gln
    115                 120                 125

Pro Ser Leu Leu Val Ala Lys Arg Lys Pro Leu Asn Ile Ser Ile Asp
130                 135                 140

Leu Pro Gly Met Arg Lys Glu Asn Thr Ile Thr Val Gln Asn Pro Thr
145                 150                 155                 160

Tyr Gly Asn Val Ala Gly Ala Val Asp Asp Leu Val Ser Thr Trp Asn
            165                 170                 175

Glu Lys Tyr Ser Thr Thr His Thr Leu Pro Ala Arg Met Gln Tyr Thr
```

```
            180                 185                 190
Glu Ser Met Val Tyr Ser Lys Ser Gln Ile Ala Ser Ala Leu Asn Val
            195                 200                 205

Asn Ala Lys Tyr Leu Asp Asn Ser Leu Asn Ile Gly Phe Asn Ala Val
            210                 215                 220

Ala Asn Gly Glu Lys Lys Val Met Val Ala Ala Tyr Lys Gln Ile Phe
225                 230                 235                 240

Tyr Thr Val Ser Ala Glu Leu Pro Asn Asn Pro Ser Asp Leu Phe Asp
            245                 250                 255

Asn Ser Val Thr Phe Asp Glu Leu Thr Arg Lys Gly Val Asn Asn Ser
            260                 265                 270

Ala Pro Pro Val Met Val Ser Asn Val Ala Tyr Gly Arg Thr Ile Tyr
            275                 280                 285

Val Lys Leu Glu Thr Thr Ser Lys Ser Lys Asp Val Gln Ala Ala Phe
            290                 295                 300

Lys Ala Leu Leu Lys Asn Asn Ser Val Glu Thr Ser Gly Gln Tyr Lys
305                 310                 315                 320

Asp Ile Phe Glu Glu Ser Thr Phe Thr Ala Val Val Leu Gly Gly Asp
            325                 330                 335

Ala Lys Glu His Asn Lys Val Val Thr Lys Asp Phe Asn Glu Ile Arg
            340                 345                 350

Asn Ile Ile Lys Asp Asn Ala Glu Leu Ser Leu Lys Asn Pro Ala Tyr
            355                 360                 365

Pro Ile Ser Tyr Thr Ser Thr Phe Leu Lys Asp Asn Ala Thr Ala Ala
            370                 375                 380

Val His Asn Asn Thr Asp Tyr Ile Glu Thr Thr Thr Thr Glu Tyr Ser
385                 390                 395                 400

Ser Ala Lys Met Thr Leu Asp His Tyr Gly Ala Tyr Val Ala Gln Phe
            405                 410                 415

Asp Val Ser Trp Asp Glu Phe Thr Phe Asp Gln Lys Gly Asn Glu Val
            420                 425                 430

Leu Thr His Lys Thr Trp Asp Gly Ser Gly Lys Asp Lys Thr Ala His
            435                 440                 445

Tyr Ser Thr Val Ile Pro Leu Pro Pro Asn Ser Lys Asn Ile Lys Ile
            450                 455                 460

Val Ala Arg Glu Cys Thr Gly Leu Ala Trp Glu Trp Trp Arg Thr Ile
465                 470                 475                 480

Ile Asn Glu Gln Asn Val Pro Leu Thr Asn Glu Ile Lys Val Ser Ile
            485                 490                 495

Gly Gly Thr Thr Leu Tyr Pro Thr Ala Ser Ile Ser His
            500                 505

<210> SEQ ID NO 5
<211> LENGTH: 500
<212> TYPE: PRT
<213> ORGANISM: Clostridium perfringens

<400> SEQUENCE: 5

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
            35                  40                  45
```

```
Arg Asn Glu Val Leu Ala Ser Asn Gly Asp Lys Ile Glu Ser Phe Val
     50                  55                  60
Pro Lys Glu Gly Lys Lys Ala Gly Asn Lys Phe Ile Val Val Glu Arg
 65                  70                  75                  80
Gln Lys Arg Ser Leu Thr Thr Ser Pro Val Asp Ile Ser Ile Ile Asp
                 85                  90                  95
Ser Val Asn Asp Arg Thr Tyr Pro Gly Ala Leu Gln Leu Ala Asp Lys
            100                 105                 110
Ala Phe Val Glu Asn Arg Pro Thr Ile Leu Met Val Lys Arg Lys Pro
        115                 120                 125
Ile Asn Ile Asn Ile Asp Leu Pro Gly Leu Lys Gly Glu Asn Ser Ile
130                 135                 140
Lys Val Asp Asp Pro Thr Tyr Gly Lys Val Ser Gly Ala Ile Asp Glu
145                 150                 155                 160
Leu Val Ser Lys Trp Asn Glu Lys Tyr Ser Ser Thr His Thr Leu Pro
                165                 170                 175
Ala Arg Thr Gln Tyr Ser Glu Ser Met Val Tyr Ser Lys Ser Gln Ile
            180                 185                 190
Ser Ser Ala Leu Asn Val Asn Ala Lys Val Leu Glu Asn Ser Leu Gly
        195                 200                 205
Val Asp Phe Asn Ala Val Ala Asn Asn Glu Lys Lys Val Met Ile Leu
210                 215                 220
Ala Tyr Lys Gln Ile Phe Tyr Thr Val Ser Ala Asp Leu Pro Lys Asn
225                 230                 235                 240
Pro Ser Asp Leu Phe Asp Asp Ser Val Thr Phe Asn Asp Leu Lys Gln
                245                 250                 255
Lys Gly Val Ser Asn Glu Ala Pro Pro Leu Met Val Ser Asn Val Ala
            260                 265                 270
Tyr Gly Arg Thr Ile Tyr Val Lys Leu Glu Thr Thr Ser Ser Ser Lys
        275                 280                 285
Asp Val Gln Ala Ala Phe Lys Ala Leu Ile Lys Asn Thr Asp Ile Lys
290                 295                 300
Asn Ser Gln Gln Tyr Lys Asp Ile Tyr Glu Asn Ser Ser Phe Thr Ala
305                 310                 315                 320
Val Val Leu Gly Gly Asp Ala Gln Glu His Asn Lys Val Val Thr Lys
                325                 330                 335
Asp Phe Asp Glu Ile Arg Lys Val Ile Lys Asp Asn Ala Thr Phe Ser
            340                 345                 350
Thr Lys Asn Pro Ala Tyr Pro Ile Ser Tyr Thr Ser Val Phe Leu Lys
        355                 360                 365
Asp Asn Ser Val Ala Ala Val His Asn Lys Thr Asp Tyr Ile Glu Thr
370                 375                 380
Thr Ser Thr Glu Tyr Ser Lys Gly Lys Ile Asn Leu Asp His Ser Gly
385                 390                 395                 400
Ala Tyr Val Ala Gln Phe Glu Val Ala Trp Asp Glu Val Ser Tyr Asp
                405                 410                 415
Lys Glu Gly Asn Glu Val Leu Thr His Lys Thr Trp Asp Gly Asn Tyr
            420                 425                 430
Gln Asp Lys Thr Ala His Tyr Ser Thr Val Ile Pro Leu Glu Ala Asn
        435                 440                 445
Ala Arg Asn Ile Arg Ile Lys Ala Arg Glu Cys Thr Gly Leu Ala Trp
450                 455                 460
Glu Trp Trp Arg Asp Val Ile Ser Glu Tyr Asp Val Pro Leu Thr Asn
```

```
                465                 470                 475                 480
Asn Ile Asn Val Ser Ile Trp Gly Thr Thr Leu Tyr Pro Gly Ser Ser
                    485                 490                 495

Ile Thr Tyr Asn
            500

<210> SEQ ID NO 6
<211> LENGTH: 501
<212> TYPE: PRT
<213> ORGANISM: Bacillus alvei

<400> SEQUENCE: 6

Met Lys Lys Ser Asn His Leu Lys Gly Arg Lys Val Leu Val Ser
1               5                   10                  15

Leu Leu Val Ser Leu Gln Val Phe Ala Phe Ala Ser Ile Ser Ser Ala
                20                  25                  30

Ala Pro Thr Glu Pro Asn Asp Ile Asp Met Gly Ile Ala Gly Leu Asn
            35                  40                  45

Tyr Asn Arg Asn Glu Val Leu Ala Ile Gln Gly Asp Gln Ile Ser Ser
        50                  55                  60

Phe Val Pro Lys Glu Gly Ile Gln Ser Asn Gly Lys Phe Ile Val Val
65                  70                  75                  80

Glu Arg Asp Lys Lys Ser Leu Thr Thr Ser Pro Val Asp Ile Ser Ile
                85                  90                  95

Val Asp Ser Ile Thr Asn Arg Thr Tyr Pro Gly Ala Ile Gln Leu Ala
            100                 105                 110

Asn Lys Asp Phe Ala Asp Asn Gln Pro Ser Leu Val Met Ala Ala Arg
        115                 120                 125

Lys Pro Leu Asp Ile Ser Ile Asp Leu Pro Gly Leu Lys Asn Glu Asn
130                 135                 140

Thr Ile Ser Val Gln Asn Pro Asn Tyr Gly Thr Val Ser Ser Ala Ile
145                 150                 155                 160

Asp Gln Leu Val Ser Thr Trp Gly Glu Lys Tyr Ser Ser Thr His Thr
                165                 170                 175

Leu Pro Ala Arg Leu Gln Tyr Ala Glu Ser Met Val Tyr Ser Gln Asn
            180                 185                 190

Gln Ile Ser Ser Ala Leu Asn Val Asn Ala Lys Val Leu Asn Gly Thr
        195                 200                 205

Leu Gly Ile Asp Phe Asn Ala Val Ala Asn Gly Glu Lys Lys Val Met
210                 215                 220

Val Ala Ala Tyr Lys Gln Ile Phe Tyr Thr Val Ser Ala Gly Leu Pro
225                 230                 235                 240

Asn Asn Pro Ser Asp Leu Phe Asp Asp Ser Val Thr Phe Ala Glu Leu
                245                 250                 255

Ala Arg Lys Gly Val Ser Asn Glu Ala Pro Pro Leu Met Val Ser Asn
            260                 265                 270

Val Ala Tyr Gly Arg Thr Ile Tyr Val Lys Leu Glu Thr Thr Ser Lys
        275                 280                 285

Ser Asn Asp Val Gln Thr Ala Phe Lys Leu Leu Leu Asn Asn Pro Ser
290                 295                 300

Ile Gln Ala Ser Gly Gln Tyr Lys Asp Ile Tyr Glu Asn Ser Ser Phe
305                 310                 315                 320

Thr Ala Val Val Leu Gly Gly Asp Ala Gln Thr His Asn Gln Val Val
                325                 330                 335
```

```
Thr Lys Asp Phe Asn Val Ile Gln Ser Val Ile Lys Asp Asn Ala Gln
            340                 345                 350

Phe Ser Ser Lys Asn Pro Ala Tyr Pro Ile Ser Tyr Thr Ser Val Phe
        355                 360                 365

Leu Lys Asp Asn Ser Ile Ala Ala Val His Asn Asn Thr Glu Tyr Ile
    370                 375                 380

Glu Thr Lys Thr Thr Glu Tyr Ser Lys Gly Lys Ile Lys Leu Asp His
385                 390                 395                 400

Ser Gly Ala Tyr Val Ala Gln Phe Glu Val Tyr Trp Asp Glu Phe Ser
                405                 410                 415

Tyr Asp Ala Asp Gly Gln Glu Ile Val Thr Arg Lys Ser Trp Asp Gly
            420                 425                 430

Asn Trp Arg Asp Arg Ser Ala His Phe Ser Thr Glu Ile Pro Leu Pro
        435                 440                 445

Pro Asn Ala Lys Asn Ile Arg Ile Phe Ala Arg Glu Cys Thr Gly Leu
    450                 455                 460

Ala Trp Glu Trp Trp Arg Thr Val Val Asp Glu Tyr Asn Val Pro Leu
465                 470                 475                 480

Ala Ser Asp Ile Asn Val Ser Ile Trp Gly Thr Thr Leu Tyr Pro Lys
                485                 490                 495

Ser Ser Ile Thr His
            500

<210> SEQ ID NO 7
<211> LENGTH: 574
<212> TYPE: PRT
<213> ORGANISM: Streptococcus canis

<400> SEQUENCE: 7

Met Lys Asp Met Ser Asn Lys Lys Ile Phe Lys Lys Tyr Ser Arg Val
1               5                   10                  15

Ala Gly Leu Leu Thr Ala Ala Leu Ile Val Gly Asn Leu Val Thr Ala
                20                  25                  30

Asn Ala Asp Ser Asn Lys Gln Asn Thr Ala Asn Thr Glu Thr Thr Thr
            35                  40                  45

Thr Asn Glu Gln Pro Lys Pro Glu Ser Ser Glu Leu Thr Thr Glu Lys
    50                  55                  60

Ala Gly Gln Lys Met Asp Asp Met Leu Asn Ser Asn Asp Met Ile Lys
65                  70                  75                  80

Leu Ala Pro Lys Glu Met Pro Leu Glu Ser Ala Glu Lys Glu Glu Lys
                85                  90                  95

Lys Ser Glu Asp Asn Lys Lys Ser Glu Glu Asp His Thr Glu Glu Ile
            100                 105                 110

Asn Asp Lys Ile Tyr Ser Leu Asn Tyr Asn Glu Leu Glu Val Leu Ala
        115                 120                 125

Lys Asn Gly Glu Thr Ile Glu Asn Phe Val Pro Lys Glu Gly Val Lys
    130                 135                 140

Lys Ala Asp Lys Phe Ile Val Ile Glu Arg Lys Lys Asn Ile Asn
145                 150                 155                 160

Thr Thr Pro Val Asp Ile Ser Ile Ile Asp Ser Val Thr Asp Arg Thr
                165                 170                 175

Tyr Pro Ala Ala Leu Gln Leu Ala Asn Lys Gly Phe Thr Glu Asn Lys
            180                 185                 190

Pro Asp Ala Val Val Thr Lys Arg Asn Pro Gln Lys Ile His Ile Asp
        195                 200                 205
```

Leu Pro Gly Met Gly Asp Lys Ala Thr Val Glu Val Asn Asp Pro Thr
210                 215                 220

Tyr Ala Asn Val Ser Thr Ala Ile Asp Asn Leu Val Asn Gln Trp His
225                 230                 235                 240

Asp Asn Tyr Ser Gly Gly Asn Thr Leu Pro Ala Arg Thr Gln Tyr Thr
            245                 250                 255

Glu Ser Met Val Tyr Ser Lys Ser Gln Ile Glu Ala Ala Leu Asn Val
        260                 265                 270

Asn Ser Lys Ile Leu Asp Gly Thr Leu Gly Ile Asp Phe Lys Ser Ile
    275                 280                 285

Ser Lys Gly Glu Lys Lys Val Met Ile Ala Ala Tyr Lys Gln Ile Phe
290                 295                 300

Tyr Thr Val Ser Ala Asn Leu Pro Asn Pro Ala Asp Val Phe Asp
305                 310                 315                 320

Lys Ser Val Thr Phe Lys Glu Leu Gln Ala Lys Gly Val Ser Asn Glu
            325                 330                 335

Ala Pro Pro Leu Phe Val Ser Asn Val Ala Tyr Gly Arg Thr Val Phe
        340                 345                 350

Val Lys Leu Glu Thr Ser Ser Lys Ser Asn Asp Val Glu Ala Ala Phe
    355                 360                 365

Ser Ala Ala Leu Lys Gly Thr Asp Val Lys Thr Asn Gly Lys Tyr Ser
370                 375                 380

Asp Ile Leu Glu Asn Ser Ser Phe Thr Ala Val Val Leu Gly Ala Asp
385                 390                 395                 400

Ala Ala Glu His Asn Lys Val Val Thr Lys Asp Phe Asp Val Ile Arg
            405                 410                 415

Asn Val Ile Lys Ala Asn Ala Thr Phe Ser Arg Lys Asn Pro Ala Tyr
        420                 425                 430

Pro Ile Ser Tyr Thr Ser Val Phe Leu Lys Asn Asn Lys Ile Ala Gly
    435                 440                 445

Val Asn Asn Arg Ser Glu Tyr Val Glu Thr Thr Ser Thr Glu Tyr Thr
450                 455                 460

Ser Gly Lys Ile Asn Leu Ser His Gln Gly Ala Tyr Val Ala Gln Tyr
465                 470                 475                 480

Glu Ile Leu Trp Asp Glu Ile Asn Tyr Asp Asp Lys Gly Lys Glu Val
            485                 490                 495

Ile Thr Lys Arg Arg Trp Asp Asn Asn Trp Tyr Ser Lys Thr Ser Pro
        500                 505                 510

Phe Ser Thr Val Ile Pro Leu Gly Ala Asn Ser Arg Asn Ile Arg Ile
    515                 520                 525

Met Ala Arg Glu Cys Thr Gly Leu Ala Trp Glu Trp Trp Arg Lys Val
530                 535                 540

Ile Asp Glu Arg Asp Val Lys Leu Ser Lys Glu Ile Asn Val Asn Ile
545                 550                 555                 560

Ser Gly Ser Thr Leu Ser Pro Tyr Gly Ser Ile Thr Tyr Lys
            565                 570

<210> SEQ ID NO 8
<211> LENGTH: 571
<212> TYPE: PRT
<213> ORGANISM: Streptococcus equisimilis

<400> SEQUENCE: 8

Met Ser Asn Lys Lys Ile Phe Lys Lys Tyr Ser Arg Val Ala Gly Leu

```
1               5                   10                  15
Leu Thr Ala Ala Leu Ile Val Gly Asn Leu Val Thr Ala Asn Ala Asp
                20                  25                  30

Ser Asn Lys Gln Asn Thr Ala Asn Thr Glu Thr Thr Thr Asn Glu
        35                  40                  45

Gln Pro Lys Pro Glu Ser Ser Glu Leu Thr Thr Glu Lys Ala Gly Gln
        50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Asn Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
            130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
            165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
        210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
            245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
            290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
            370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
            420                 425                 430
```

```
Tyr Thr Ser Val Phe Leu Lys Asn Asn Lys Ile Ala Gly Val Asn Asn
            435                 440                 445

Arg Ser Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
            515                 520                 525

Glu Cys Thr Gly Leu Ala Trp Glu Trp Trp Arg Lys Val Ile Asp Glu
        530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570
```

```
<210> SEQ ID NO 9
<211> LENGTH: 571
<212> TYPE: PRT
<213> ORGANISM: Streptococcus pyogenes

<400> SEQUENCE: 9

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Ser Glu
        35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
```

```
                225                 230                 235                 240
Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
                260                 265                 270

Ile Leu Asp Gly Thr Leu Gly Ile Asp Phe Lys Ser Ile Ser Lys Gly
                275                 280                 285

Glu Lys Lys Val Met Ile Ala Ala Tyr Lys Gln Ile Phe Tyr Thr Val
                290                 295                 300

Ser Ala Asn Leu Pro Asn Asn Pro Ala Asp Val Phe Asp Lys Ser Val
305                 310                 315                 320

Thr Phe Lys Asp Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
                340                 345                 350

Glu Thr Ser Ser Lys Ser Asn Asp Val Glu Ala Ala Phe Ser Ala Ala
                355                 360                 365

Leu Lys Gly Thr Asp Val Lys Thr Asn Gly Lys Tyr Ser Asp Ile Leu
                370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
                420                 425                 430

Tyr Thr Ser Val Phe Leu Lys Asn Asn Lys Ile Ala Gly Val Asn Asn
                435                 440                 445

Arg Thr Glu Tyr Val Glu Thr Thr Ser Thr Glu Tyr Thr Ser Gly Lys
                450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
                500                 505                 510

Val Ile Pro Leu Gly Ala Asn Ser Arg Asn Ile Arg Ile Met Ala Arg
                515                 520                 525

Glu Cys Thr Gly Leu Ala Trp Glu Trp Trp Arg Lys Val Ile Asp Glu
                530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 10
<211> LENGTH: 514
<212> TYPE: PRT
<213> ORGANISM: Clostridium novyi

<400> SEQUENCE: 10

Met Lys Lys Ser Leu Lys Thr Ile Ile Arg Ser Ile Ser Phe Leu Ser
1               5                   10                  15

Ile Leu Thr Leu Thr Cys Ser Cys Asn Phe Ile Thr Ser Thr Gln Lys
                20                  25                  30
```

-continued

```
Asn Val Ser Leu Leu Ser Gly Pro Asn Lys Val Ile Lys Pro Lys Lys
             35                  40                  45

Thr Lys Ser Leu Asp Asp Arg Ile Tyr Gly Leu Lys Tyr Asp Pro Asn
 50                  55                  60

Lys Ile Leu Ser Phe Asn Gly Glu Lys Val Glu Asn Phe Val Pro Asn
 65                  70                  75                  80

Glu Gly Phe Ser Thr Pro Asp Lys Tyr Ile Val Ile Lys Arg Glu Lys
                 85                  90                  95

Lys Ser Ile Ser Asp Ser Thr Ala Asp Ile Ala Val Ile Asp Ser Met
                100                 105                 110

Asn Asp Lys Thr Tyr Pro Gly Ala Ile Gln Leu Ala Asn Arg Asn Leu
                115                 120                 125

Ile Glu Asn Lys Pro Asn Ile Val Ser Cys Glu Arg Lys Pro Ile Thr
            130                 135                 140

Ile Ser Ile Asp Leu Pro Gly Met Gly Glu Glu Gly Lys Thr Thr Ile
145                 150                 155                 160

Thr Ser Pro Thr Tyr Ser Ser Val Lys Ala Gly Ile Asp Ser Leu Leu
                165                 170                 175

Asn Lys Trp Asn Ser His Tyr Ser Ser Ile Tyr Ser Ile Pro Thr Arg
                180                 185                 190

Phe Ser Tyr Ser Asp Ser Met Val Tyr Ser Lys Ser Gln Leu Ser Ala
            195                 200                 205

Lys Leu Gly Cys Asn Phe Lys Ala Leu Asn Lys Ala Leu Asp Ile Asp
            210                 215                 220

Phe Asp Ser Ile Tyr Lys Gly Gln Lys Lys Val Met Leu Leu Ala Tyr
225                 230                 235                 240

Lys Gln Ile Phe Tyr Thr Val Asn Val Asp Ala Pro Asn His Pro Ser
                245                 250                 255

Asp Phe Phe Gly Asp Lys Val Thr Phe Asn Asp Leu Ala Lys Lys Gly
            260                 265                 270

Val Asn Ser Lys Asn Pro Pro Val Tyr Val Ser Ser Val Ser Tyr Gly
            275                 280                 285

Arg Thr Ile Tyr Val Lys Leu Glu Thr Thr Ser Lys Ser Ala Asn Val
290                 295                 300

Lys Ala Ala Phe Lys Ala Leu Ile Glu Asn Gln Asn Ile Ser Ser Asn
305                 310                 315                 320

Ser Glu Tyr Lys Asn Ile Leu Asn Gln Ser Ser Phe Thr Ala Thr Val
                325                 330                 335

Leu Gly Gly Gly Ala Lys Glu His Asn Lys Val Ile Thr Lys Asn Phe
                340                 345                 350

Asp Glu Ile Arg Asn Ile Ile Thr Asn Asn Ser Glu Tyr Ser Pro Arg
            355                 360                 365

Asn Pro Gly Tyr Pro Ile Ala Tyr Thr Thr Ser Phe Leu Lys Asp Asn
370                 375                 380

Ser Val Ala Thr Val Asn Asn Lys Thr Asp Tyr Ile Glu Thr Thr Ser
385                 390                 395                 400

Thr Glu Tyr Thr Asn Gly Lys Ile Thr Leu Asp His Arg Gly Ala Tyr
                405                 410                 415

Val Ala Lys Phe Asn Ile Thr Trp Asp Glu Val Ser Tyr Asp Lys Asn
            420                 425                 430

Gly Lys Glu Ile Val Glu His Lys Ser Trp Glu Gly Asn Asp Phe Gly
            435                 440                 445

Arg Thr Ala His Phe Asn Thr Glu Leu Tyr Leu Lys Gly Asn Ala Arg
```

```
                    450                 455                 460
Asn Ile Cys Ile Lys Ala Lys Glu Cys Thr Gly Leu Ala Trp Glu Trp
465                 470                 475                 480

Trp Arg Thr Ile Ile Asp Asp Lys Asn Val Pro Leu Val Lys Asn Arg
                    485                 490                 495

Lys Val Tyr Ile Trp Gly Thr Thr Leu Tyr Pro Arg Thr Leu Thr Glu
                500                 505                 510

Ile Glu

<210> SEQ ID NO 11
<211> LENGTH: 527
<212> TYPE: PRT
<213> ORGANISM: Clostridium tetani

<400> SEQUENCE: 11

Met Asn Lys Asn Val Leu Lys Phe Val Ser Arg Ser Leu Leu Ile Phe
1               5                   10                  15

Ser Met Thr Gly Leu Ile Ser Asn Tyr Asn Ser Ser Asn Val Leu Ala
                20                  25                  30

Lys Gly Asn Val Glu Glu His Ser Leu Ile Asn Asn Gly Gln Val Val
            35                  40                  45

Thr Ser Asn Thr Lys Cys Asn Leu Ala Lys Asp Asn Ser Ser Asp Ile
        50                  55                  60

Asp Lys Asn Ile Tyr Gly Leu Ser Tyr Asp Pro Arg Lys Ile Leu Ser
65                  70                  75                  80

Tyr Asn Gly Glu Gln Val Glu Asn Phe Val Pro Ala Glu Gly Phe Glu
                85                  90                  95

Asn Pro Asp Lys Phe Ile Val Val Lys Arg Glu Lys Lys Ser Ile Ser
                100                 105                 110

Asp Ser Thr Ala Asp Ile Ser Ile Ile Asp Ser Ile Asn Asp Arg Thr
            115                 120                 125

Tyr Pro Gly Ala Ile Gln Leu Ala Asn Arg Asn Leu Met Glu Asn Lys
        130                 135                 140

Pro Asp Ile Ile Ser Cys Glu Arg Lys Pro Ile Thr Ile Ser Val Asp
145                 150                 155                 160

Leu Pro Gly Met Ala Glu Asp Gly Lys Lys Val Val Asn Ser Pro Thr
                165                 170                 175

Tyr Ser Ser Val Asn Ser Ala Ile Asn Ser Ile Leu Asp Thr Trp Asn
                180                 185                 190

Ser Lys Tyr Ser Ser Lys Tyr Thr Ile Pro Thr Arg Met Ser Tyr Ser
            195                 200                 205

Asp Thr Met Val Tyr Ser Gln Ser Gln Leu Ser Ala Ala Val Gly Cys
        210                 215                 220

Asn Phe Lys Ala Leu Asn Lys Ala Leu Asn Ile Asp Phe Asp Ser Ile
225                 230                 235                 240

Phe Lys Gly Glu Lys Lys Val Met Leu Leu Ala Tyr Lys Gln Ile Phe
                245                 250                 255

Tyr Thr Val Ser Val Asp Pro Pro Asn Arg Pro Ser Asp Leu Phe Gly
                260                 265                 270

Asp Ser Val Thr Phe Asp Glu Leu Ala Leu Lys Gly Ile Asn Asn Asn
            275                 280                 285

Asn Pro Pro Ala Tyr Val Ser Asn Val Ala Tyr Gly Arg Thr Ile Tyr
        290                 295                 300

Val Lys Leu Glu Thr Thr Ser Lys Ser Ser His Val Lys Ala Ala Phe
```

305 310 315 320

Lys Ala Leu Ile Asn Asn Gln Asp Ile Ser Ser Asn Ala Glu Tyr Lys
325 330 335

Asp Ile Leu Asn Gln Ser Ser Phe Thr Ala Thr Val Leu Gly Gly Gly
340 345 350

Ala Gln Glu His Asn Lys Ile Ile Thr Lys Asp Phe Asp Glu Ile Arg
355 360 365

Asn Ile Ile Lys Asn Asn Ser Val Tyr Ser Pro Gln Asn Pro Gly Tyr
370 375 380

Pro Ile Ser Tyr Thr Thr Thr Phe Leu Lys Asp Asn Ser Ile Ala Ser
385 390 395 400

Val Asn Asn Lys Thr Glu Tyr Ile Glu Thr Thr Ala Thr Glu Tyr Thr
405 410 415

Asn Gly Lys Ile Val Leu Asp His Ser Gly Ala Tyr Val Ala Gln Phe
420 425 430

Gln Val Thr Trp Asp Glu Val Ser Tyr Asp Glu Lys Gly Asn Glu Ile
435 440 445

Val Glu His Lys Ala Trp Glu Gly Asn Asn Arg Asp Arg Thr Ala His
450 455 460

Phe Asn Thr Glu Ile Tyr Leu Lys Gly Asn Ala Arg Asn Ile Ser Val
465 470 475 480

Lys Ile Arg Glu Cys Thr Gly Leu Ala Trp Glu Trp Trp Arg Thr Ile
485 490 495

Val Asp Val Lys Asn Ile Pro Leu Ala Lys Glu Arg Thr Phe Tyr Ile
500 505 510

Trp Gly Thr Thr Leu Tyr Pro Lys Thr Ser Ile Glu Thr Lys Met
515 520 525

<210> SEQ ID NO 12
<211> LENGTH: 528
<212> TYPE: PRT
<213> ORGANISM: Listeria ivanovii

<400> SEQUENCE: 12

Met Lys Lys Ile Met Leu Leu Leu Met Thr Leu Leu Leu Val Ser Leu
1 5 10 15

Pro Leu Ala Gln Glu Ala Gln Ala Asp Ala Ser Val Tyr Ser Tyr Gln
20 25 30

Gly Ile Ile Ser His Met Ala Pro Pro Ala Ser Pro Pro Ala Lys Pro
35 40 45

Lys Thr Pro Val Glu Lys Lys Asn Ala Ala Gln Ile Asp Gln Tyr Ile
50 55 60

Gln Gly Leu Asp Tyr Asp Lys Asn Asn Ile Leu Val Tyr Asp Gly Glu
65 70 75 80

Ala Val Lys Asn Val Pro Pro Lys Ala Gly Tyr Lys Glu Gly Asn Gln
85 90 95

Tyr Ile Val Val Glu Lys Lys Lys Lys Ser Ile Asn Gln Asn Asn Ala
100 105 110

Asp Ile Gln Val Ile Asn Ser Leu Ala Ser Leu Thr Tyr Pro Gly Ala
115 120 125

Leu Val Lys Ala Asn Ser Glu Leu Val Glu Asn Gln Pro Asp Val Leu
130 135 140

Pro Val Lys Arg Asp Ser Val Thr Leu Ser Ile Asp Leu Pro Gly Met
145 150 155 160

```
Val Asn His Asp Asn Glu Ile Val Val Gln Asn Ala Thr Lys Ser Asn
            165                 170                 175

Ile Asn Asp Gly Val Asn Thr Leu Val Asp Arg Trp Asn Asn Lys Tyr
        180                 185                 190

Ser Glu Glu Tyr Pro Asn Ile Ser Ala Lys Ile Asp Tyr Asp Gln Glu
        195                 200                 205

Met Ala Tyr Ser Glu Ser Gln Leu Val Ala Lys Phe Gly Ala Ala Phe
        210                 215                 220

Lys Ala Val Asn Asn Ser Leu Asn Val Asn Phe Gly Ala Ile Ser Glu
225                 230                 235                 240

Gly Lys Val Gln Glu Glu Val Ile Asn Phe Lys Gln Ile Tyr Tyr Thr
            245                 250                 255

Val Asn Val Asn Glu Pro Thr Ser Pro Ser Arg Phe Phe Gly Lys Ser
            260                 265                 270

Val Thr Lys Glu Asn Leu Gln Ala Leu Gly Val Asn Ala Glu Asn Pro
        275                 280                 285

Pro Ala Tyr Ile Ser Ser Val Ala Tyr Gly Arg Asp Ile Phe Val Lys
        290                 295                 300

Leu Ser Thr Ser Ser His Ser Thr Arg Val Lys Ala Ala Phe Asp Thr
305                 310                 315                 320

Ala Phe Lys Gly Lys Ser Val Lys Gly Asp Thr Glu Leu Glu Asn Ile
            325                 330                 335

Ile Gln Asn Ala Ser Phe Lys Ala Val Ile Tyr Gly Gly Ser Ala Lys
            340                 345                 350

Asp Glu Val Glu Ile Ile Asp Gly Asp Leu Ser Lys Leu Arg Asp Ile
        355                 360                 365

Leu Lys Gln Gly Ala Asn Phe Asp Lys Lys Asn Pro Gly Val Pro Ile
    370                 375                 380

Ala Tyr Thr Thr Asn Phe Leu Lys Asp Asn Gln Leu Ala Val Val Lys
385                 390                 395                 400

Asn Asn Ser Glu Tyr Ile Glu Thr Thr Ser Lys Ala Tyr Ser Asp Gly
            405                 410                 415

Lys Ile Asn Leu Asp His Ser Gly Ala Tyr Val Ala Arg Phe Asn Val
            420                 425                 430

Thr Trp Asp Glu Val Ser Tyr Asp Ala Asn Gly Asn Glu Val Val Glu
        435                 440                 445

His Lys Lys Trp Ser Glu Asn Asp Lys Asp Lys Leu Ala His Phe Thr
    450                 455                 460

Thr Ser Ile Tyr Leu Pro Gly Asn Ala Arg Asn Ile Asn Ile His Ala
465                 470                 475                 480

Lys Glu Cys Thr Gly Leu Ala Trp Glu Trp Trp Arg Thr Val Val Asp
            485                 490                 495

Asp Arg Asn Leu Pro Leu Val Lys Asn Arg Asn Val Cys Ile Trp Gly
            500                 505                 510

Thr Thr Leu Tyr Pro Ala Tyr Ser Asp Thr Val Asp Asn Pro Ile Lys
        515                 520                 525

<210> SEQ ID NO 13
<211> LENGTH: 529
<212> TYPE: PRT
<213> ORGANISM: Listeria monocytogenes

<400> SEQUENCE: 13

Met Lys Lys Ile Met Leu Val Phe Ile Thr Leu Ile Leu Val Ser Leu
1               5                   10                  15
```

```
Pro Ile Ala Gln Gln Thr Glu Ala Lys Asp Ala Ser Ala Phe Asn Lys
            20                  25                  30

Glu Asn Leu Ile Ser Ser Met Ala Pro Ala Ser Pro Ala Ser
        35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
            370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430
```

Ile Ser Trp Asp Glu Ile Asn Tyr Asp Pro Gly Asn Glu Ile Val
                435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Arg Thr Val Ile
                485                 490                 495

Asp Asp Arg Asn Leu Pro Leu Val Lys Asn Arg Asn Ile Ser Ile Trp
                500                 505                 510

Gly Thr Thr Leu Tyr Pro Lys Tyr Ser Asn Ser Val Asp Asn Pro Ile
            515                 520                 525

Glu

<210> SEQ ID NO 14
<211> LENGTH: 530
<212> TYPE: PRT
<213> ORGANISM: Listeria seeligeri

<400> SEQUENCE: 14

Met Lys Ile Phe Gly Leu Val Ile Met Ser Leu Leu Phe Val Ser Leu
1               5                   10                  15

Pro Ile Thr Gln Gln Pro Glu Ala Arg Asp Val Pro Ala Tyr Asp Arg
                20                  25                  30

Ser Glu Val Thr Ile Ser Pro Ala Glu Thr Pro Glu Ser Pro Pro Ala
            35                  40                  45

Thr Pro Lys Thr Pro Val Glu Lys Lys His Ala Glu Ile Asn Lys
50                  55                  60

Tyr Ile Trp Gly Leu Asn Tyr Asp Lys Asn Ser Ile Leu Val Tyr Gln
65                  70                  75                  80

Gly Glu Ala Val Thr Asn Val Pro Pro Lys Lys Gly Tyr Lys Asp Gly
                85                  90                  95

Ser Glu Tyr Ile Val Val Glu Lys Lys Lys Gly Ile Asn Gln Asn
            100                 105                 110

Asn Ala Asp Ile Ser Val Ile Asn Ala Ile Ser Ser Leu Thr Tyr Pro
        115                 120                 125

Gly Ala Leu Val Lys Ala Asn Arg Glu Leu Val Glu Asn Gln Pro Asn
130                 135                 140

Val Leu Pro Val Lys Arg Asp Ser Leu Thr Leu Ser Val Asp Leu Pro
145                 150                 155                 160

Gly Met Thr Lys Lys Asp Asn Lys Ile Phe Val Lys Asn Pro Thr Lys
                165                 170                 175

Ser Asn Val Asn Asn Ala Val Asn Thr Leu Val Glu Arg Trp Asn Asp
            180                 185                 190

Lys Tyr Ser Lys Ala Tyr Pro Asn Ile Asn Ala Lys Ile Asp Tyr Ser
        195                 200                 205

Asp Glu Met Ala Tyr Ser Ser Gln Leu Ile Ala Lys Phe Gly Thr
210                 215                 220

Ala Phe Lys Ala Val Asn Asn Ser Leu Asn Val Asn Phe Glu Ala Ile
225                 230                 235                 240

Ser Asp Gly Lys Val Gln Glu Val Ile Ser Phe Lys Gln Ile Tyr
            245                 250                 255

Tyr Asn Ile Asn Val Asn Glu Pro Thr Ser Pro Ser Lys Phe Phe Gly
        260                 265                 270

```
Gly Ser Val Thr Lys Glu Gln Leu Asp Ala Leu Gly Val Asn Ala Glu
        275                 280                 285

Asn Pro Pro Ala Tyr Ile Ser Val Ala Tyr Gly Arg Gln Val Tyr
290                 295                 300

Val Lys Leu Ser Ser Ser His Ser Asn Lys Val Lys Thr Ala Phe
305                 310                 315                 320

Glu Ala Ala Met Ser Gly Lys Ser Val Lys Gly Asp Val Glu Leu Thr
                325                 330                 335

Asn Ile Ile Lys Asn Ser Ser Phe Lys Ala Val Ile Tyr Gly Gly Ser
            340                 345                 350

Ala Lys Glu Glu Val Glu Ile Ile Asp Gly Asn Leu Gly Glu Leu Arg
        355                 360                 365

Asp Ile Leu Lys Lys Gly Ser Thr Tyr Asp Arg Glu Asn Pro Gly Val
    370                 375                 380

Pro Ile Ser Tyr Thr Thr Asn Phe Leu Lys Asp Asn Asp Leu Ala Val
385                 390                 395                 400

Val Lys Asn Asn Ser Glu Tyr Ile Glu Thr Thr Ser Lys Ser Tyr Thr
                405                 410                 415

Asp Gly Lys Ile Asn Ile Asp His Ser Gly Gly Tyr Val Ala Gln Phe
            420                 425                 430

Asn Ile Ser Trp Asp Glu Val Ser Tyr Asp Glu Asn Gly Asn Glu Ile
        435                 440                 445

Lys Val His Lys Lys Trp Gly Glu Asn Tyr Lys Ser Lys Leu Ala His
    450                 455                 460

Phe Thr Ser Ser Ile Tyr Leu Pro Gly Asn Ala Arg Asn Ile Asn Ile
465                 470                 475                 480

Tyr Ala Arg Glu Cys Thr Gly Leu Phe Trp Glu Trp Trp Arg Thr Val
                485                 490                 495

Ile Asp Asp Arg Asn Leu Pro Leu Val Lys Asn Arg Asn Val Ser Ile
            500                 505                 510

Trp Gly Thr Thr Leu Tyr Pro Arg His Ser Asn Asn Val Asp Asn Pro
        515                 520                 525

Ile Gln
    530

<210> SEQ ID NO 15
<211> LENGTH: 497
<212> TYPE: PRT
<213> ORGANISM: Streptococcus suis

<400> SEQUENCE: 15

Met Arg Lys Ser Ser His Leu Ile Leu Ser Ser Ile Val Ser Leu Ala
1               5                   10                  15

Leu Val Gly Val Thr Pro Leu Ser Val Leu Ala Asp Ser Lys Gln Asp
                20                  25                  30

Ile Asn Gln Tyr Phe Gln Ser Leu Thr Tyr Glu Pro Gln Glu Ile Leu
            35                  40                  45

Thr Asn Glu Gly Glu Tyr Ile Asp Asn Pro Ala Thr Thr Gly Met
        50                  55                  60

Leu Glu Asn Gly Arg Phe Val Val Leu Arg Arg Glu Lys Lys Asn Ile
65                  70                  75                  80

Thr Asn Asn Ser Ala Asp Ile Ala Val Ile Asp Ala Lys Ala Ala Asn
                85                  90                  95

Ile Tyr Pro Gly Ala Leu Leu Arg Ala Asp Gln Asn Leu Leu Asp Asn
            100                 105                 110
```

```
Asn Pro Thr Leu Ile Ser Ile Ala Arg Gly Asp Leu Thr Leu Ser Leu
        115                 120                 125

Asn Leu Pro Gly Leu Ala Asn Gly Asp Ser His Thr Val Val Asn Ser
130                 135                 140

Pro Thr Arg Ser Thr Val Arg Thr Gly Val Asn Asn Leu Leu Ser Lys
145                 150                 155                 160

Trp Asn Asn Thr Tyr Ala Gly Glu Tyr Gly Asn Thr Gln Ala Glu Leu
                165                 170                 175

Gln Tyr Asp Glu Thr Met Ala Tyr Ser Met Ser Gln Leu Lys Thr Lys
            180                 185                 190

Phe Gly Thr Ser Phe Glu Lys Ile Ala Val Pro Leu Asp Ile Asn Phe
        195                 200                 205

Asp Ala Val Asn Ser Gly Glu Lys Gln Val Gln Ile Val Asn Phe Lys
    210                 215                 220

Gln Ile Tyr Tyr Thr Val Ser Val Asp Glu Pro Glu Ser Pro Ser Lys
225                 230                 235                 240

Leu Phe Ala Glu Gly Thr Thr Val Glu Asp Leu Lys Arg Asn Gly Ile
                245                 250                 255

Thr Asp Glu Val Pro Pro Val Tyr Val Ser Ser Val Ser Tyr Gly Arg
            260                 265                 270

Ser Met Phe Ile Lys Leu Glu Thr Ser Ser Arg Ser Thr Gln Val Gln
        275                 280                 285

Ala Ala Phe Lys Ala Ala Ile Lys Gly Val Asp Ile Ser Gly Asn Ala
    290                 295                 300

Glu Tyr Gln Asp Ile Leu Lys Asn Thr Ser Phe Ser Ala Tyr Ile Phe
305                 310                 315                 320

Gly Gly Asp Ala Gly Ser Ala Ala Thr Val Val Ser Gly Asn Ile Glu
                325                 330                 335

Thr Leu Lys Lys Ile Ile Glu Glu Gly Ala Arg Tyr Gly Lys Leu Asn
            340                 345                 350

Pro Gly Val Pro Ile Ser Tyr Ser Thr Asn Phe Val Lys Asp Asn Arg
        355                 360                 365

Pro Ala Gln Ile Leu Ser Asn Ser Glu Tyr Ile Glu Thr Thr Ser Thr
    370                 375                 380

Val His Asn Ser Ser Ala Leu Thr Leu Asp His Ser Gly Ala Tyr Val
385                 390                 395                 400

Ala Lys Tyr Asn Ile Thr Trp Glu Glu Val Ser Tyr Asn Glu Ala Gly
                405                 410                 415

Glu Glu Val Trp Glu Pro Lys Ala Trp Asp Lys Asn Gly Val Asn Leu
            420                 425                 430

Thr Ser His Trp Ser Glu Thr Ile Gln Ile Pro Gly Asn Ala Arg Asn
        435                 440                 445

Leu His Val Asn Ile Gln Glu Cys Thr Gly Leu Ala Trp Glu Trp Trp
    450                 455                 460

Arg Thr Val Tyr Asp Lys Asp Leu Pro Leu Val Gly Gln Arg Lys Ile
465                 470                 475                 480

Thr Ile Trp Gly Thr Thr Leu Tyr Pro Gln Tyr Ala Asp Glu Val Ile
                485                 490                 495

Glu

<210> SEQ ID NO 16
<211> LENGTH: 466
<212> TYPE: PRT
```

<213> ORGANISM: Streptococcus mitis

<400> SEQUENCE: 16

Met Ala Asn Lys Ala Val Asn Asp Phe Ile Leu Ala Met Asp Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Asp Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp Tyr Gln Gly Lys Glu Val Leu Thr Pro Lys Ala Trp Asn Arg Asn
385                 390                 395                 400

Gly Gln Asp Leu Thr Ala His Phe Thr Thr Ser Ile Pro Leu Lys Gly
              405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Asn Asp Leu Pro Leu Val
            435                 440                 445

Arg Lys Arg Thr Ile Ser Ile Trp Gly Thr Thr Leu Tyr Pro Gln Val
        450                 455                 460

Glu Asp
465

<210> SEQ ID NO 17
<211> LENGTH: 532
<212> TYPE: PRT
<213> ORGANISM: Streptococcus intermedius

<400> SEQUENCE: 17

Met Lys Thr Lys Gln Asn Ile Ala Arg Lys Leu Ser Arg Val Val Leu
1               5                   10                  15

Leu Ser Thr Leu Val Leu Ser Ser Ala Ala Pro Ile Ser Ala Ala Phe
            20                  25                  30

Ala Glu Thr Pro Thr Lys Pro Lys Ala Ala Gln Thr Glu Lys Lys Pro
        35                  40                  45

Glu Lys Lys Pro Glu Asn Ser Asn Ser Glu Ala Ala Lys Lys Ala Leu
    50                  55                  60

Asn Asp Tyr Ile Trp Gly Leu Gln Tyr Asp Lys Leu Asn Ile Leu Thr
65                  70                  75                  80

His Gln Gly Glu Lys Leu Lys Asn His Ser Ser Arg Glu Ala Phe His
                85                  90                  95

Arg Pro Gly Glu Tyr Val Val Ile Glu Lys Lys Gln Ser Ile Ser
            100                 105                 110

Asn Ala Thr Ser Lys Leu Ser Val Ser Ser Ala Asn Asp Asp Arg Ile
        115                 120                 125

Phe Pro Gly Ala Leu Leu Lys Ala Asp Gln Ser Leu Leu Glu Asn Leu
    130                 135                 140

Pro Thr Leu Ile Pro Val Asn Arg Gly Lys Thr Thr Ile Ser Val Asn
145                 150                 155                 160

Leu Pro Gly Leu Lys Asn Gly Glu Ser Asn Leu Thr Val Glu Asn Pro
                165                 170                 175

Ser Asn Ser Thr Val Arg Thr Ala Val Asn Asn Leu Val Glu Lys Trp
            180                 185                 190

Ile Gln Lys Tyr Ser Lys Thr His Ala Val Pro Ala Arg Met Gln Tyr
        195                 200                 205

Glu Ser Ile Ser Ala Gln Ser Met Ser Gln Leu Gln Ala Lys Phe Gly
    210                 215                 220

Ala Asp Phe Ser Lys Val Gly Ala Pro Leu Asn Val Asp Phe Ser Ser
225                 230                 235                 240

Val His Lys Gly Glu Lys Gln Val Phe Ile Ala Asn Phe Arg Gln Val
                245                 250                 255

Tyr Tyr Thr Ala Ser Val Asp Ser Pro Asn Ser Pro Ser Ala Leu Phe
            260                 265                 270

Gly Ser Gly Ile Thr Pro Thr Asp Leu Ile Asn Arg Gly Val Asn Ser
        275                 280                 285

Lys Thr Pro Pro Val Tyr Val Ser Asn Val Ser Tyr Gly Arg Ala Met
    290                 295                 300

Tyr Val Lys Phe Glu Thr Thr Ser Lys Ser Thr Lys Val Gln Ala Ala
305                 310                 315                 320

Ile Asp Ala Val Val Lys Gly Ala Lys Leu Lys Ala Gly Thr Glu Tyr
            325                 330                 335

Glu Asn Ile Leu Lys Asn Thr Lys Ile Thr Ala Val Val Leu Gly Gly
        340                 345                 350

Asn Pro Gly Glu Ala Ser Lys Val Ile Thr Gly Asn Ile Asp Thr Leu
    355                 360                 365

Lys Asp Leu Ile Gln Lys Gly Ser Asn Phe Ser Ala Gln Ser Pro Ala
370                 375                 380

Val Pro Ile Ser Tyr Thr Thr Ser Phe Val Lys Asp Asn Ser Ile Ala
385                 390                 395                 400

Thr Ile Gln Asn Asn Thr Asp Tyr Ile Glu Thr Lys Val Thr Ser Tyr
            405                 410                 415

Lys Asp Gly Ala Leu Thr Leu Asn His Asp Gly Ala Phe Val Ala Arg
        420                 425                 430

Phe Tyr Val Tyr Trp Glu Glu Leu Gly His Asp Ala Asp Gly Tyr Glu
    435                 440                 445

Thr Ile Arg Ser Arg Ser Trp Ser Gly Asn Gly Tyr Asn Arg Gly Ala
450                 455                 460

His Tyr Ser Thr Thr Leu Arg Phe Lys Gly Asn Val Arg Asn Ile Arg
465                 470                 475                 480

Val Lys Val Leu Gly Ala Thr Gly Leu Ala Trp Glu Pro Trp Arg Leu
            485                 490                 495

Ile Tyr Ser Lys Asn Asp Leu Pro Leu Val Pro Gln Arg Asn Ile Ser
        500                 505                 510

Thr Trp Gly Thr Thr Leu His Pro Gln Phe Glu Asp Lys Val Val Lys
    515                 520                 525

Asp Asn Thr Asp
    530

<210> SEQ ID NO 18
<211> LENGTH: 665
<212> TYPE: PRT
<213> ORGANISM: Streptococcus mitis

<400> SEQUENCE: 18

Met Asn Gln Glu Lys Arg Leu His Arg Phe Val Lys Lys Cys Gly Leu
1               5                   10                  15

Gly Val Cys Ser Ala Val Val Ala Ala Phe Leu Leu Asn Ala Gln Gly
            20                  25                  30

Val Ala Leu Ala Thr Glu Gln Gly Asn Arg Pro Val Glu Thr Glu Asn
        35                  40                  45

Ile Ala Arg Gly Lys Gln Ala Ser Gln Ser Ser Thr Ala Tyr Gly Gly
    50                  55                  60

Ala Ala Thr Arg Ala Val Asp Gly Asn Val Asp Ser Asp Tyr Gly His
65                  70                  75                  80

His Ser Val Thr His Thr Asn Phe Glu Asp Asn Ala Trp Trp Gln Val
                85                  90                  95

Asp Leu Gly Lys Thr Glu Asn Val Gly Lys Val Lys Leu Tyr Asn Arg
            100                 105                 110

Gly Asp Gly Asn Val Ala Asn Arg Leu Ser Asn Phe Asp Val Val Leu
        115                 120                 125

Leu Asn Glu Ala Lys Gln Glu Val Ala Arg Gln His Phe Asp Ser Leu

```
            130                 135                 140
Asn Gly Lys Ala Glu Leu Glu Val Phe Phe Thr Ala Lys Asp Ala Arg
145                 150                 155                 160

Tyr Val Lys Val Glu Leu Lys Thr Lys Asn Thr Pro Leu Ser Leu Ala
                165                 170                 175

Glu Val Glu Val Phe Arg Ser Ala Thr Thr Gln Val Gly Gln Asp Arg
            180                 185                 190

Thr Ala Pro Val Asp Gln Thr Ser Ala Leu Lys Asp Tyr Leu Phe
                195                 200                 205

Gly Leu Thr Tyr Asn Pro Leu Asp Ile Leu Thr Arg Lys Gly Glu Thr
            210                 215                 220

Leu Glu Asn Arg Tyr Asn Thr Ser Ala Lys Glu Gln Asn Gly Glu Phe
225                 230                 235                 240

Val Val Val Glu Lys Ile Lys Lys Thr Leu Ser Thr Gly Thr Ala Asp
                245                 250                 255

Val Ser Ile Asn Gly Asn Gln Asn Val Phe Leu Gly Gly Leu Tyr Lys
            260                 265                 270

Ala Asn Gln Asn Leu Leu Glu Asn Gln Pro Glu Leu Ile Ser Leu Ala
275                 280                 285

Arg Ala Lys Gly Thr Val Ser Val Asp Leu Pro Gly Met Ile His Ser
290                 295                 300

Glu Asn Lys Ile Glu Ala Asn Pro Thr Thr Ser Gly Met Gln Glu Ala
305                 310                 315                 320

Met Asn Thr Leu Val Glu Lys Trp Thr Lys Asn Tyr Ser Ser Ser His
                325                 330                 335

Ser Val Pro Ala Arg Val Gln Tyr Glu Ser Thr Thr Ala Tyr Ser Met
            340                 345                 350

Asn Gln Leu Lys Ala Lys Phe Gly Ala Asp Phe Glu Lys Ala Gly Ala
                355                 360                 365

Pro Leu Lys Ile Asp Phe Glu Ala Val Gln Lys Gly Glu Lys Gln Ile
            370                 375                 380

Glu Val Val Asn Phe Lys Gln Ile Tyr Tyr Thr Ala Thr Phe Asp Ala
385                 390                 395                 400

Pro Thr Asn Pro Ala Ala Val Phe Asp Lys Ser Val Thr Pro Glu Asp
                405                 410                 415

Leu Lys Gln Arg Gly Val Asp Ser Gln Thr Pro Pro Tyr Val Ser
            420                 425                 430

Asn Val Ser Tyr Gly Arg Gln Ile Tyr Val Lys Phe Glu Ser Thr Ser
                435                 440                 445

Lys Ser Thr Glu Leu Lys Ala Ala Ile Asn Ala Val Ile Lys Gly Ala
            450                 455                 460

Thr Ile Ala Pro Asn Ser Glu Trp Ser Arg Leu Leu Lys Asn Thr Ser
465                 470                 475                 480

Val Thr Ala Val Ile Val Gly Asn Ala Ser Gly Ala Ala Lys Val
                485                 490                 495

Val Thr Gly Thr Val Glu Asn Leu Lys Glu Leu Ile Arg Glu Gly Ala
            500                 505                 510

Asn Phe Ser Ala Gln Ser Pro Ala Val Pro Ile Ser Tyr Lys Thr Ala
                515                 520                 525

Phe Leu Lys Asp Asn Ala Gln Ala Thr Leu Gln Asn Ser Thr Asp Tyr
            530                 535                 540

Ile Glu Thr Lys Val Thr Ser Tyr Lys Asn Gly Phe Leu Lys Leu His
545                 550                 555                 560
```

His Lys Gly Ala Tyr Ile Ala Arg Tyr Tyr Ile Tyr Trp Asp Glu Ile
            565                 570                 575

Thr Tyr Asp Glu Gln Gly Asn Pro Glu Ile Arg Ser Arg Gln Trp Glu
            580                 585                 590

Asp Asn Gly Lys Asn Arg Thr Ser Gly Phe Gln Thr Glu Ile Gln Phe
            595                 600                 605

Arg Gly Asn Val Arg Asn Leu Arg Ile Lys Val Gln Glu Lys Thr Gly
            610                 615                 620

Leu Val Trp Glu Pro Trp Arg Thr Val Tyr Asn Arg Thr Asp Leu Pro
625                 630                 635                 640

Leu Val Gln Gln Arg Thr Ile Thr His Trp Gly Thr Thr Leu Asn Pro
            645                 650                 655

Lys Val Asp Glu Lys Ile Val Asn Glu
            660                 665

<210> SEQ ID NO 19
<211> LENGTH: 534
<212> TYPE: PRT
<213> ORGANISM: Arcanobacterium pyogenes

<400> SEQUENCE: 19

Met Lys Arg Lys Ala Phe Ala Ser Leu Val Ala Ser Val Val Ala Ala
1               5                   10                  15

Ala Thr Val Thr Met Pro Thr Ala Ser Phe Ala Ala Gly Leu Gly Asn
            20                  25                  30

Ser Ser Gly Leu Thr Asp Gly Leu Ser Ala Pro Arg Ala Ser Ile Ser
            35                  40                  45

Pro Thr Asp Lys Val Asp Leu Lys Ser Ala Gln Glu Thr Asp Glu Thr
        50                  55                  60

Gly Val Asp Lys Tyr Ile Arg Gly Leu Lys Tyr Asp Pro Ser Gly Val
65              70                  75                  80

Leu Ala Val Lys Gly Glu Ser Ile Glu Asn Val Pro Val Thr Lys Asp
                85                  90                  95

Gln Leu Lys Asp Gly Thr Tyr Thr Val Phe Lys His Glu Arg Lys Ser
            100                 105                 110

Phe Asn Asn Leu Arg Ser Asp Ile Ser Ala Phe Asp Ala Asn Asn Ala
            115                 120                 125

His Val Tyr Pro Gly Ala Leu Val Leu Ala Asn Lys Asp Leu Ala Lys
        130                 135                 140

Gly Ser Pro Thr Ser Ile Gly Ile Ala Arg Ala Pro Gln Thr Val Ser
145                 150                 155                 160

Val Asp Leu Pro Gly Leu Val Asp Gly Lys Asn Lys Val Val Ile Asn
                165                 170                 175

Asn Pro Thr Lys Ser Ser Val Thr Gln Gly Leu Asn Gly Leu Leu Asp
            180                 185                 190

Gly Trp Ile Gln Arg Asn Ser Lys Tyr Pro Asp His Ala Ala Lys Ile
            195                 200                 205

Ser Tyr Asp Glu Thr Met Val Thr Ser Lys Arg Gln Leu Glu Ala Lys
        210                 215                 220

Leu Gly Leu Gly Phe Glu Lys Val Ser Ala Lys Leu Asn Val Asp Phe
225                 230                 235                 240

Asp Ala Ile His Lys Arg Glu Arg Gln Val Ala Ile Ala Ser Phe Lys
                245                 250                 255

Gln Ile Tyr Tyr Thr Ala Ser Val Asp Thr Pro Thr Ser Pro His Ser

```
            260                 265                 270
Val Phe Gly Pro Asn Val Thr Ala Gln Asp Leu Lys Asp Arg Gly Val
            275                 280                 285

Asn Asn Lys Asn Pro Leu Gly Tyr Ile Ser Ser Val Ser Tyr Gly Arg
        290                 295                 300

Gln Ile Phe Val Lys Leu Glu Thr Thr Ser Thr Ser Asn Asp Val Gln
305                 310                 315                 320

Ala Ala Phe Ser Gly Leu Phe Lys Ala Lys Phe Gly Asn Leu Ser Thr
                325                 330                 335

Glu Phe Lys Ala Lys Tyr Ala Asp Ile Leu Asn Lys Thr Arg Ala Thr
            340                 345                 350

Val Tyr Ala Val Gly Gly Ser Ala Arg Gly Val Glu Val Ala Thr
            355                 360                 365

Gly Asn Ile Asp Ala Leu Lys Lys Ile Lys Glu Glu Ser Thr Tyr
        370                 375                 380

Ser Thr Lys Val Pro Ala Val Pro Val Ser Tyr Ala Val Asn Phe Leu
385                 390                 395                 400

Lys Asp Asn Gln Leu Ala Ala Val Arg Ser Ser Gly Asp Tyr Ile Glu
                405                 410                 415

Thr Thr Ala Thr Thr Tyr Lys Ser Gly Glu Ile Thr Phe Arg His Gly
            420                 425                 430

Gly Gly Tyr Val Ala Lys Phe Arg Leu Lys Trp Asp Glu Ile Ser Tyr
        435                 440                 445

Asp Pro Gln Gly Lys Glu Ile Arg Thr Pro Lys Thr Trp Ser Gly Asn
    450                 455                 460

Trp Ala Ala Arg Thr Leu Gly Phe Arg Glu Thr Ile Gln Leu Pro Ala
465                 470                 475                 480

Asn Ala Arg Asn Ile His Val Glu Ala Gly Ala Thr Gly Leu Ala
                485                 490                 495

Trp Asp Pro Trp Trp Thr Val Ile Asn Lys Lys Asn Leu Pro Leu Val
        500                 505                 510

Pro His Arg Glu Ile Val Leu Lys Gly Thr Thr Leu Asn Pro Trp Val
    515                 520                 525

Glu Asp Asn Val Lys Ser
    530

<210> SEQ ID NO 20
<211> LENGTH: 1416
<212> TYPE: DNA
<213> ORGANISM: Streptococcus pneumoniae

<400> SEQUENCE: 20
ctagtcattt tctaccttat cctctacctg aggatagaga gttgttcccc aaatagaaat      60
cgtccgctta cgcactagtg gcaaatcggt tttttcataa accgtacgcc accattccca     120
ggcaagcccg gtacactctc taattttgac agagagatta cgaacattcc cttttaaagg     180
aatactagtg gtaaagtgag ccgtcaaatc ctgcccattt ctgtcccaag ccttaggagt     240
caagacttcc ttaccttgat gatcatagga taattcatcc caagtaatat aatattgggc     300
aacataggca ccactatgat ccagcagtaa atctccgttt ctgtaagctg taaccttagt     360
ctcaacatag tctgtactgt tttgaaaggt cgcaactaca ttgtcacgta aaaagaagt      420 tgtataggaa atcggcaagc ctggatgatc tgctgtaaag cgactgcctt cttgaatcaa     480
gtcctctacc atatccacct tgcctgttac aactcgggca ccgaacttg ggtcgccccc      540
```

-continued

```
taaaataacc gccttcactt ctgtattgtc caaaatctgc ttccactctg tctgaggagc    600
taccttgact ccttttatca aagcttcaaa agcagcctct acttcatcac tcttactcgt    660
ggtttccaac ttgagataga cttggcgccc ataagcaaca ctcgaaatat agaccaaagg    720
acgctctgca gaaattcctc tctgttttaa atcctctacc gttacagtat cttgaaacac    780
atctcctgga tttttaacag cgtctacgct gactgtataa taaatctgct taaaattaac    840
aatctgaatc tgcttttcac ctgaatggac agagttaaaa tcaatatcaa gagaattccc    900
tgtcttttca aagtcagaac caaacttgac cttgagttgt tccatgctgt gagccgttat    960
tttttcatac tgcattctag ctgggacatt attgacctga ccataatctt gatgccactt   1020
agccaacaaa tcgtttaccg ctccgcgaac acttgaattg ctggggtctt ccacttggag   1080
aaagctatcg ctacttgcca aaccaggcaa atcaatacta taagtcatcg gagcacgatc   1140
aaccgcaaga agagtgggat tattctctaa caaggtctca tccactacga gaagtgctcc   1200
aggatagagg cgactgtcgt tggtagctgt tacagaaata tcacttgtat ttgtcgacaa   1260
gctccgcttc tttctttcga taacaacaaa ctcatcgggt agctgattac cctctttgat   1320
gaaacgattt tcaatacttt ctccctgatg ggtcaagagt ttctttttat cgtaattcat   1380
agctagtata aagtcattta ctgctttatt tgccat                             1416

<210> SEQ ID NO 21
<211> LENGTH: 1530
<212> TYPE: DNA
<213> ORGANISM: Bacillus cereus

<400> SEQUENCE: 21
ctgaatatta agaaaaacac taaaagaaga aagttccttg catgtttatt agttagttta     60
tgcactatta attattcatc tatttccttc gcagaaacac aagcaagtaa tgcaactgat    120
gtaaccaaaa atgctagtgg cattgatact ggtatagcaa atcttaaata taataatcaa    180
gaggttttag ctgtaaatgg tgataaagta gaaagttttg ttccgaaaga aagtatcaat    240
tcaaatggta aatttgtagt agtggaacgc gagaaaaaat cacttacaac gtcaccagtc    300
gatatttcaa ttattgattc tgtagtgaat cgcacgtatc caggagctgt acaacttgca    360
aataaagctt ttgcagacaa tcaaccaagt ttattagtgg ctaagagaaa gcctttgaat    420
attagtatag acttaccggg catgagaaaa gaaaatacaa tcactgtcca aaatccgaca    480
tatggtaatg tagctggagc agtagacgat ttagtatcta cttggaatga aaagtattct    540
acaacacata cgttacctgc aagaatgcag tatacggaat ctatggttta tagtaaatca    600
caaatagcaa gtgctcttaa tgttaacgct aaatatcttg ataacagtct aaacattgat    660
tttaatgcgg ttgcaaatgg agagaaaaaa gtgatggtag cggcgtataa gcaaatattt    720
tatacggtaa gtgctgaact acctaacaat ccatccgacc tttttgataa tagcgttact    780
tttgacgagt taactcgaaa aggcgtaagt aattcggctc cacctgttat ggtttcaaat    840
gtagcttatg gtagaacgat ttatgtaaaa ttagaaacaa catctaagag caaagatgta    900
caagctgctt ttaaagcctt acttaagaat aacagcgttg aaacaagtgg acagtataaa    960
gatatttttg aagaaagtac ctttactgct gtagtattag gcggagatgc gaaagagcat   1020
aacaaggttg ttactaaaga tttcaatgaa atccgaaata tcattaaaga taatgctgaa   1080
ttaagtctta aaaatccagc atacccaatt tcatatacaa gcactttctt aaaagataat   1140
tcaactgctg ctgttcataa caatacagat tatattgaga cgacaactac agaatattca   1200
agtgctaaaa tgacacttga tcattacggt gcttacgttg ctcaatttga tgtatcttgg   1260
```

```
gatgaattca catttgacca aaagggtaac gaagtactaa cacataaaac gtgggatggt    1320
agcggaaaag acaaaacggc tcattactct acagttatcc cactcccacc aaattcaaaa    1380
aatataaaaa ttgtagcaag agaatgtaca ggtcttgcat gggaatggtg gagaacaatt    1440
attaatgaac aaaatgttcc attaacaaat gaaataaaag tttcaattgg aggaacaaca    1500
ttatacccaa cagctagtat tagtcattaa                                     1530
```

<210> SEQ ID NO 22
<211> LENGTH: 1539
<212> TYPE: DNA
<213> ORGANISM: Bacillus anthracis

<400> SEQUENCE: 22

```
ctaatgacta atagtagcag ttggatataa tgttgttcct ccaattgaaa cctttatttc      60
atttgttaat ggaacatttt gttcattaat gatagttctc caccattccc atgcaagacc     120
tgtacattct cttgcaacga ttttatatt ttttgaattt ggtggaagag ggataactgt      180
agagtaatgg gctgttttgt ctttgccact accttcccat gttttatgtg ttagtacttc     240
tttcccattt tgatcaaatg taaattcatc ccaagataca tcaaattgag caacgtaagc     300
accgtaatga tcgagtgtca ttttagcact tgaatattct gtagttgtcg tctcgatata     360
atctgtattg ttatgaacag cagcagttgc attatctttt aagaacgtgc ttgtatatga     420
aattgggtat gctggatttt taaagcttaa ttcagcatta tctttaataa tatttcggat     480
ttcattgaaa tcttttgtaa caaccttgtt atgctctttc gcatctccgc ctaatactac     540
agcagtaaag gtactttctt caaaaatatc tttgtactgt ccactcgttt cgacgctgtt     600
attcttaagt agagctttaa atgcagcttg tacatcttta ctcttagatg ttgtttctaa     660
ttttacataa accgttctac cataagctac atttgaaacc ataacaggtg gagccgaatt     720
acttactcct ttacgagtta actcatcaaa agtaacacta ttatcaaaga gatcagatgg     780
attattaggt agttcagcac ttacagtata aaatatttgt ttatatgccg ccaccatcac     840 tttctttct ccatttgcaa ctgcattaaa gtcaatattt agactgttat caagatattt      900
agcattaaca ttaagagcac ttgcgatttg tgatttacta taaaccatag attctgtata     960
ctgcattctt gcaggtaacg tatgtgttgt ggaatacttt tcattccaag tagatactaa    1020
atcatctact gctccagcca cattaccata tgtcggattt tggacagtga ttgtatttc     1080 ttttctcatg ccaggtaagt ctatactaat attcaaaggc tttctcttag ctactaataa    1140
actcggttga ttgtctgcaa atgctttatt ggcaagttgt acagctcctg gatacgtacg    1200
attcactaca gaatcaataa tcaaaatatc gactggtgac gttgtaagtg attttttctc    1260
gcgttccact actacaaatt taccgtttga attgatactc tctttcggaa taaaactctc    1320
tactttatca ccatttactg ctaaaatatc tctactatca tactttagat tgctataccc    1380
agtattaata tcactagcat tttttattgc accagttgca ttaccggctt gtgtttctgc    1440
aaaagaaata gacgaataat gaatggtaca tagactaact aataaacatg caaggaactt    1500
tcttctttta gtgttttctct taatattcag aaaaatcac                          1539
```

<210> SEQ ID NO 23
<211> LENGTH: 1530
<212> TYPE: DNA
<213> ORGANISM: Bacillus thuringiensis

<400> SEQUENCE: 23

```
ctgaatatta agaaaaacac taaaagaaga aagttccttg catgtttatt agttagtcta      60
tgcaccatta attattcatc tatttccttc gcagaaacac aagcaagtaa tgcgactgat     120
gtaaccaaaa atgctagtgg cattgatact ggtatagcaa atcttaaata taatattcaa     180
gaggttttag ctgtaaatgg tgataaagta gaaagttttg ttccgaaaga aagtatcaat     240
tcaaatggta aatttgtagt agtggaacgc gagaaaaaat cacttacaac gtcaccagtc     300
gatatttcaa ttattgattc tgtggtgaat cgcacgtatc caggagctgt acaacttgct     360
aataaagctt ttgcagacaa tcaaccgagt ttattagtgg ctaagagaaa gcctttgaat     420
attagtatag acttaccggg catgagaaaa gaaaatacaa tcactgtcca aaatccgaca     480
tatggtaatg tagctggagc agtagacgat ttagtatcta cttggaatga aaagtattct     540
acaacacata cgttacctgc aagaatgcag tatacggaat ctatggttta tagtaaatca     600
caaattgcaa gtgctcttaa tgttaacgct aaatatcttg ataacagtct aaatattggt     660
tttaatgcgg ttgcaaatgg agagaaaaaa gtgatggtag cggcgtataa gcaaatattt     720
tatacggtaa gtgctgaact acctaacaat ccatccgacc tttttgataa tagcgttact     780
tttgacgagt taactcgaaa aggcgtaaat aattcggctc cacctgttat ggtttcaaat     840
gtagcttatg gtagaacgat ttatgtaaaa ttagaaacaa catctaagag caaagatgta     900
caagctgctt ttaaagcctt acttaagaat aacagcgttg aaacaagtgg acagtataaa     960 gatattttg aagaaagtac ctttactgct gtagtattag gcggagatgc gaaagaacat    1020
aacaaggttg ttactaaaga tttcaatgaa atccgaaata ttattaaaga taatgctgaa    1080
ttaagtctta aaaatccagc ataccccaatt tcatatacaa gtactttctt aaaagataat    1140
gcaactgctg ctgttcataa caatacagat tatattgaga cgacaactac agaatattca    1200
agtgctaaaa tgcacttga tcattacggt gcttacgttg ctcaatttga tgtatcttgg    1260
gatgaattca catttgatca aaagggtaac gaagtactaa cacataaaac gtgggatggt    1320
agtggaaaag acaaaacggc tcattactct acagttatcc ctcttccacc gaattcaaaa    1380
aatataaaaa ttgtagcaag agaatgtaca ggtcttgcat gggaatggtg agaacaatt    1440 attaatgaac aaaacgttcc attaacaaat gaaataaaag tttcaattgg aggaacaaca    1500
ttatacccaa cagctagtat tagtcattaa                                    1530

<210> SEQ ID NO 24
<211> LENGTH: 1503
<212> TYPE: DNA
<213> ORGANISM: Clostridium perfringens

<400> SEQUENCE: 24
atgataagat ttaagaaaac aaaattaata gcaagtattg caatggcttt atgtctgttt      60
tctcaaccag taatcagttt ctcaaaggat ataacagata aaaatcaaag tattgattct     120
ggaatatcaa gtttaagtta caatagaaat gaagttttag ctagtaatgg agataaaatt     180
gaaagctttg ttccaaagga aggtaaaaaa gctggtaata aatttatagt tgtagaacgt     240
caaaaaagat cccttacaac atcaccagta gatatatcaa taattgattc tgtaaatgac     300
cgtacatatc caggagcatt acaacttgca gataaagcat ttgtggaaaa tagacctaca     360
atcttaatgg taaaagaaa gcctattaac attaatatag atttaccagg attaaagggc     420
gaaaatagta taaaggttga tgatccaacc tatggaaaag tttctggagc aattgatgaa     480
ttagtatcta gtggaatgaa aagtattca tctacacata ctttaccagc aagaactcaa     540
tattcagaat ctatggttta tagtaaatca caaatatcaa gtgcccttaa tgttaatgct     600
```

```
aaagtccttg aaaactcact tggagtagac tttaatgcag tagcaaacaa tgagaaaaaa      660
gttatgattt tagcatataa acaaatattc tatacagtaa gtgcagattt acctaagaat      720
ccatcagatc tttttgatga cagtgttaca tttaatgatt taaaacaaaa gggagtaagt      780
aatgaagcac ctccacttat ggtttcaaat gtagcttatg gaagaacaat atatgttaag      840
ttagaaacta cttctagtag taaagatgta caagctgctt tcaaagctct tataaagaac      900
actgatataa aaaatagtca acaatataaa gatatttatg aaaatagttc cttcacagca      960
gtagttttag gaggagatgc acaagaacat aacaaagttg taactaaaga ctttgatgaa     1020
ataagaaaag taattaaaga caatgcaact tttagtacaa aaaacccagc atatccaata     1080
tcttatacta gtgttttctt aaaagataac tcagttgctg ctgttcacaa taaaacagat     1140
tatatagaaa caacttctac agagtattct aagggaaaaa taaacttaga tcatagtgga     1200
gcctatgttg cacagtttga agtagcctgg gatgaagttt catatgacaa agaaggaaat     1260
gaagttttaa ctcataaaac atgggatgga aattatcaag ataaaacagc tcactattca     1320
acagtaatac ctcttgaagc taatgcaaga aatataagaa taaaagcaag agagtgtaca     1380
ggccttgctt gggaatggtg gagagatgtt ataagtgaat atgatgttcc attaacaaat     1440
aatataaatg tttcaatatg gggaacaact ttataccctg gatctagtat tacttacaat     1500
taa                                                                  1503

<210> SEQ ID NO 25
<211> LENGTH: 1506
<212> TYPE: DNA
<213> ORGANISM: Bacillus alvei

<400> SEQUENCE: 25
atgaagaaaa aatcaaacca cttgaaagga aggaaagtac tcgtaagttt gttagtaagc       60
ttacaagtgt tcgcttttgc gagtatttcc tccgcagcac caaccgaacc caatgatatt      120
gatatgggga tcgcaggact gaactataat cgcaatgagg ttttggctat tcaagggat      180 caaatcagta gttttgttcc caaagaaggc attcagtcca atggcaaatt tatcgtggtt      240
gaacgggaca aaaaatcact cacaacgtca cccgtagata ttttccatcgt tgattcaatc      300 acgaatcgca cgtatccagg cgcaatacac cttgcaaata aggattttgc cgataatcag      360
cctagtctgg ttatggctgc gagaaaacca ttagatatta gcatcgatct gcctggtttg      420
aagaacgaga atacaatttc cgttcaaaat ccaaattacg gcactgtatc tagtgccatt      480
gatcagctcg tgtcgacttg gggcgagaag tattccagca cgcatacact gcctgcaaga      540
ttacaatacg ctgaatccat ggtttacagc caaaatcaaa tttccagcgc cctgaatgtg      600
aacgctaaag tactgaacgg tacactcgga atcgacttta acgcggttgc aaatggcgag      660
aaaaaagtga tggttgctgc ttacaagcaa atctttttata ccgtaagtgc aggactgccc      720
aacaatccat cagacttgtt cgatgacagt gtgacatttg ctgagttagc tcgcaaggga      780
gtaagcaatg aggcaccgcc gctgatggta tctaacgtgg cttacggcag aactatttac      840
gtaaaattgg aaacaacttc taagagcaat gacgtacaaa cggcatttaa attgttgctc      900
aataatccta gcatacaagc tagcggacag tacaaagata tttatgagaa cagctcgttt      960
actgccgttg tactaggcgg cgacgcgcaa acccataacc aagtcgttac gaaagacttc     1020
aatgttatcc aaagtgtaat caaggacaat gcacaattta gcagcaagaa ccctgcttac     1080
ccgatttcat atacaagtgt cttcttgaaa gacaattcca ttgctgctgt tcacaacaat     1140
```

| | |
|---|---|
| accgagtata tcgagacgaa aacgacggaa tattcgaagg gtaaaattaa gcttgatcat | 1200 |
| agtggtgcat atgtagctca gtttgaagta tattgggatg aattttcata tgatgcagat | 1260 |
| ggacaagaaa tcgtgactcg taaaagttgg gatggaaatt ggcgcgatag atctgctcat | 1320 |
| ttctcaacag aaatcccact tcctcctaat gccaagaaca taagaatttt tgcgagagaa | 1380 |
| tgcacaggtc ttgcttggga atggtggaga acagttgttg atgaatataa cgttccgtta | 1440 |
| gcaagcgata ttaatgtttc gatttgggga acaacgttat atccgaaatc atccattact | 1500 |
| cactaa | 1506 |

<210> SEQ ID NO 26
<211> LENGTH: 1725
<212> TYPE: DNA
<213> ORGANISM: Streptococcus canis

<400> SEQUENCE: 26

| | |
|---|---|
| atgaaggaca tgtctaataa aaaaatattt aaaaaataca gtcgcgtcgc tgggctatta | 60 |
| acggcagctc ttatcgttgg taatcttgtt actgctaatg ctgactcgaa caaacaaaac | 120 |
| actgccaata cagaaaccac aacgacaaat gaacaaccaa aaccagaaag tagtgagcta | 180 |
| actacagaaa aagcaggtca gaaaatggat gatatgctta actctaacga tatgattaag | 240 |
| cttgctccca agaaaatgcc actagaatct gcagaaaaag aagaaaaaaa gtcagaagac | 300 |
| aataaaaaaa gcgaagaaga tcatactgaa gaaatcaatg acaagattta ttcactaaat | 360 |
| tataatgagc ttgaagtact tgctaaaaat ggtgaaacca ttgaaaactt tgttcctaaa | 420 |
| gaaggcgtta agaaagctga caaatttatt gtcattgaaa gaagaaaaaa aaatatcaac | 480 |
| actacaccgg tcgatatttc catcattgac tctgtcactg ataggaccta tccagcagcc | 540 |
| cttcagctgg ctaataaagg tttaccgaa acaaaccag acgcagtagt caccaagcga | 600 |
| aacccacaaa aaatccatat tgatttacca ggtatgggag acaaagcaac ggttgaggtc | 660 |
| aatgacccta cctatgccaa tgtttcaaca gctattgata atccttgtta accaatggcat | 720 |
| gataattatt ctggtggtaa tacgcttcct gccagaacac aatatactga atcaatggta | 780 |
| tattctaaat cacagattga agcagctcta aatgttaata gtaaaatctt agatggtact | 840 |
| ttaggcattg atttcaagtc gatttcaaaa ggtgaaaaga aggtgatgat tgcagcatac | 900 |
| aagcaaattt tttacaccgt atcagcaaac cttcctaata atcctgcgga tgtgtttgat | 960 |
| aaatcagtga cctttaaaga gttgcaagca aaaggtgtca gcaatgaagc cccgccactc | 1020 |
| tttgtgagta acgtagctta tggtcgaact gtttttgtca aactagaaac aagttctaaa | 1080 |
| agtaatgatg ttgaagcggc ctttagtgca gctctaaaag gaacagatgt taaaactaat | 1140 |
| ggaaaatact ctgatatttt agaaaatagt tcatttacag ctgtcgtttt aggagcagat | 1200 |
| gctgcagagc acaataaggt agtcacaaaa gactttgatg ttattagaaa cgttatcaaa | 1260 |
| gctaatgcta ccttcagtag aaaaaaccca gcttatccta tttcatacac cagtgttttc | 1320 |
| cttaaaaata taaaaattgc gggtgtcaat aacagaagtg aatacgttga aacaacatct | 1380 |
| accgagtaca cgagtggaaa aattaacctg tctcatcaag gtgcctatgt tgctcaatat | 1440 |
| gaaatccttt gggatgaaat caattatgat gacaaaggaa agaagtgat tactaaacga | 1500 |
| cgttgggaca caactggta gtaagaca tcaccatta gcacagttat cccactagga | 1560 |
| gctaattcac gaaatatccg tatcatggct agagagtgca ccggcttagc ttgggaatgg | 1620 |
| tggcgaaaag tgatcgacga aagagatgtg aaactgtcta agaaatcaa tgtcaacatc | 1680 |
| tcaggatcaa ccctgagccc atatggttcg attacttata agtag | 1725 |

<210> SEQ ID NO 27
<211> LENGTH: 1715
<212> TYPE: DNA
<213> ORGANISM: Streptococcus equisimilis

<400> SEQUENCE: 27

| | | | | | | |
|---|---|---|---|---|---|---|
| atgtctaata | aaaaaatatt | taaaaaatac | agtcgcgtcg | ctgggctatt | aacggcagct | 60 |
| cttatcgttg | gtaatcttgt | tactgctaat | ctgactcgaa | caaacaaaac | actgccaata | 120 |
| cagaaaccac | aacgacaaat | gaacaaccaa | aaccagaaag | tagtgagcta | actacagaaa | 180 |
| aagcaggtca | gaaatggat | gatatgctta | actctaacga | tatgattaag | cttgctccca | 240 |
| aagaaatgcc | actagaatct | gcagaaaaag | aagaaaaaa | gtcagaagac | aataaaaaaa | 300 |
| gcgaagaaga | tcatactgaa | gaaatcaatg | acaagattta | ttcactaaat | tataatgagc | 360 |
| ttgaagtact | tgctaaaaat | ggtgaaacca | ttgaaaactt | tgttcctaaa | gaaggcgtta | 420 |
| agaaagctga | caaatttatt | gtcattgaaa | gaagaaaaa | aaatatcaac | actacaccgg | 480 |
| tcgatatttc | catcattgac | tctgtcactg | ataggaccta | tccagcagcc | cttcagctgg | 540 |
| ctaataaagg | ttttaccgaa | acaaaccag | acgcagtagt | caccaagcga | aacccacaaa | 600 |
| aaatccatat | tgatttacca | ggtatgggag | ataaagcaac | ggttgaggtc | aatgacccta | 660 |
| cctatgccaa | tgtttcaaca | gctattgata | atcttgttaa | ccaatggcat | gataattatt | 720 |
| ctggtggtaa | tacgcttcct | gccagaacac | aatatactga | atcaatggta | tattctaaat | 780 |
| cacagattga | agcagctcta | aatgttaata | gtaaaatctt | agatggtact | ttaggcattg | 840 |
| atttcaagtc | gatttcaaaa | ggtgaaaaga | aggtgatgat | tgcagcatac | aagcaaattt | 900 |
| tttacaccgt | atcagcaaac | cttcctaata | atcctgcgga | tgtgtttgat | aaatcagtga | 960 |
| cctttaaaga | gttgcaacga | aaaggtgtca | gcaatgaagc | cccgccactc | tttgtgagta | 1020 |
| acgtagctta | tggtcgaact | gttttttgtca | aactagaaac | aagttctaaa | agtaatgatg | 1080 |
| ttgaagcggc | ctttagtgca | gctctaaaag | gaacagatgt | taaaactaat | ggaaaatact | 1140 |
| ctgatatttt | agaaaatagt | tcatttacag | ctgtcgtttt | aggaggagat | gctgcagagc | 1200 |
| acaataaggt | agtcacaaaa | gactttgatg | ttattagaaa | cgttatcaaa | gataatgcta | 1260 |
| cattcagtag | aaaaaaccca | gcttatccta | tttcatacac | cagtgttttc | cttaaaaata | 1320 |
| ataaaattgc | gggtgtcaat | aacagaagtg | aatacgttga | aacaacatct | accgagtaca | 1380 |
| cgagtggaaa | aattaacctg | tctcatcaag | gtgcctatgt | tgctcaatat | gaaatccttt | 1440 |
| gggatgaaat | caattatgat | gacaaaggaa | agaagtgat | tacaaaacga | cgttgggaca | 1500 |
| acaactggta | tagtaagaca | tcaccattta | gcacagttat | cccactagga | gctaattcac | 1560 |
| gaaatatccg | tatcatggct | agagagtgca | ccggattagc | ttgggaatgg | tggcgaaaag | 1620 |
| tgatcgacga | aagagatgtg | aaactgtcta | aagaaatcaa | tgtcaacatc | tcaggatcaa | 1680 |
| ccttgagccc | atatggttcg | attacttata | agtag | | | 1715 |

<210> SEQ ID NO 28
<211> LENGTH: 1716
<212> TYPE: DNA
<213> ORGANISM: Streptococcus pyogenes

<400> SEQUENCE: 28

| | | | | | | |
|---|---|---|---|---|---|---|
| atgtctaata | aaaaaacatt | taaaaaatac | agtcgcgtcg | ctgggctact | aacggcagct | 60 |
| cttatcattg | gtaatcttgt | tactgctaat | gctgaatcga | acaaacaaaa | cactgctagt | 120 |

```
acagaaacca caacgacaag tgagcaacca aaaccagaaa gtagtgagct aactatcgaa      180
aaagcaggtc agaaaatgga tgatatgctt aactctaacg atatgattaa gcttgctccc      240
aaagaaatgc cactagaatc tgcagaaaaa gaagaaaaaa agtcagaaga caaaaaaaag      300
agcgaagaag atcacactga agaaatcaat gacaagattt attcactaaa ttataatgag      360
cttgaagtac ttgctaaaaa tggtgaaacc attgaaaatt ttgttcctaa agaaggcgtt      420
aagaaagctg ataaatttat tgtcattgaa agaagaaaaa aaatatcaa cactacacca      480 gtcgatattt ccattattga ctctgtcact gataggacct atccagcagc ccttcagctg      540
gctaataaag gttttaccga aaacaaacca gacgcggtag tcaccaagcg aaacccacaa      600
aaaatccata ttgatttacc aggtatggga gacaaagcaa cggttgaggt caatgaccct      660
acctatgcca atgtttcaac agctattgat aatcttgtta accaatggca tgataattat      720
tctggtggta atacgcttcc tgccagaaca caatatactg aatcaatggt atattctaag      780
tcacagattg aagcagctct aaatgttaat agcaaaatct tagatggtac tttaggcatt      840
gatttcaagt cgatttcaaa aggtgaaaag aaggtgatga ttgcagcata caagcaaatt      900
ttttacaccg tatcagcaaa ccttcctaat aatcctgcgg atgtgtttga taaatcagtg      960 accttaaag atttgcaacg aaaaggtgtc agcaatgaag ctccgccact ctttgtgagt     1020
aacgtagcct atggtcgaac tgttttgtc aaactagaaa caagttctaa agtaatgat     1080 gttgaagcgg cctttagtgc agctctaaaa ggaacagatg ttaaaacgaa tggaaaatac     1140
tctgatatct tagaaaatag ctcatttaca gctgtcgttt taggaggaga tgctgcagag     1200
cacaataagg tggtcacaaa agactttgat gttattagaa acgttatcaa agacaatgct     1260
accttcagta gaaaaaaccc agcttatcct atttcataca ccagtgtttt ccttaaaaat     1320
aataaaattg cgggtgtcaa taacagaact gaatacgttg aaacaacatc taccgagtac     1380
actagtggaa aaattaacct gtctcatcaa ggcgcgtatg ttgctcaata tgaaatcctt     1440
tgggatgaaa tcaattatga tgacaaagga aaagaagtga ttacaaaacg acgttgggac     1500
aacaactggt atagtaagac atcaccattt agcacagtta tcccactagg agctaattca     1560
cgaaatatcc gtatcatggc tagagagtgc accggcttag cttgggaatg gtggcgaaaa     1620
gtgatcgacg aaagagatgt gaaactatct aaagaaatca atgtcaacat ctcaggatca     1680
accttgagcc catatggttc gattacttat aagtag                                1716
```

<210> SEQ ID NO 29
<211> LENGTH: 1545
<212> TYPE: DNA
<213> ORGANISM: Clostridium novyi

<400> SEQUENCE: 29

```
atgaagaaat cttaaaaaac tataattcgt agcatatctt ttctctcaat attaacatta       60
acttgtagtt gcaactttat aacaagcacc cagaaaaatg taagcttatt atcgggacct      120
aataaagtta ttaaacctaa gaaaactaaa tccttagatg ataggattta tggattaaaa      180
tatgatccta ataaaatact atcatttaat ggagaaaaag ttgaaaattt tgtacctaac      240
gaaggttttt caacacccga taagtacatc gttataaaac gtgaaaagaa aagtatatca      300
gattctacag cagatatagc tgttatagac tcgatgaatg acaaaactta tcctggtgca      360
atacaacttg caaatagaaa tcttatagaa aacaagccta atatagtatc ttgtgaaaga      420
aagccaataa cataagtat agatttacct gggatgggtg aagaagggaa gacaactata      480
acttctccta cttattcttc tgttaaagca ggaattgatt cattgctaaa taagtggaat      540
```

```
tcacattatt cgtcaatata tagcattcca actagattta gctattcaga ttctatggtt     600
tatagtaagt ctcaattatc agctaaatta ggttgtaatt tcaaagcttt aaataaagca     660
ttggatattg attttgattc tatttataaa ggacaaaaga aagtaatgct tcttgcatat     720
aagcaaattt tttatacagt aaatgtagat gccccaaatc atccatcaga cttctttggg     780
gataaagtaa catttaatga cttagcaaaa aaaggagtta atagtaagaa tcctcctgta     840
tacgtttcaa gtgtatctta tggtagaact atttatgtaa aacttgaaac tacttctaaa     900
agtgccaatg taaaagctgc atttaaagca ctaatagaaa atcaaaatat aagcagtaat     960
tctgagtaca aaatattttt aaatcaaagc tcatttacag ctacagtatt aggtggtgga    1020
gctaaagaac ataacaaagt aataactaaa aactttgatg aaataagaaa tataataact    1080
aacaactcag aatatagtcc tagaaatcca ggttatccta tagcatatac tacttctttt    1140
ctaaaagata atagtgttgc aacagtgaac aataaaacag attatataga gacaacctct    1200
acagaatata ctaatggaaa aattactctt gatcatagag gtgcatatgt agctaaattc    1260
aatattactt gggatgaagt aagctatgat aagaatggaa aagaaatagt agaacacaaa    1320
tcatgggaag aaatgacttc ggtagaacta gctcatttca atacagaatt atacctaaaa    1380
ggtaacgctc gaaatatttg cataaaagct aaagaatgca ctggtcttgc ttgggaatgg    1440
tggagaacta atagatga taaaaatgtt cctttagtta aaaacagaaa agtctatatt    1500
tggggaacaa cattatatcc tagaacatta acagaaatag aataa                  1545
```

<210> SEQ ID NO 30
<211> LENGTH: 1584
<212> TYPE: DNA
<213> ORGANISM: Clostridium tetani

<400> SEQUENCE: 30

```
ttacatttta gtttcaattg atgtctttgg atataatgtt gtaccccata tatagaaagt      60
tctttctttt gctagtggta tatttttaac atctacaatg gttctccacc attcccatgc     120
aagacctgta cattctctta tttttacaga tatatttcgt gcatttcctt ttaaatatat     180
ttctgtatta aaatgagccg ttctatctct attatttcct tcccaagctt tatgttcaac     240
tatttcattt cccttttcgt catagctaac ctcatcccat gttacttgga attgagcaac     300
atacgctcca ctatgatcaa gtactatttt accattagta tattctgttg cagttgtttc     360
tatatattct gttttattat ttacggatgc tatactattg tcttttaaaa atgtagtagt     420
atatgaaatt ggatatcctg gattttgtgg actatacact gaattatttt taataatatt     480
tcttatttca tcaaaatcct tagtgattat cttattatgt tcttgtgctc ctcccccctaa    540 aacagtagct gtaaatgaac tttgatttaa tatatcctta tattctgcat tactacttat     600
atcctggtta ttgattagtg ctttaaaagc tgctttaaca tgtgaactct tagaggtagt     660
ttcaagtttt acataaattg ttctaccata tgcaacattt gaaacatatg caggaggatt     720
attattattt atccccttta aagccaattc atcaaaagtt acactatcac caaataaatc     780
tgatggacga tttggtgggt ctacacttac tgtataaaaa atttgtttgt atgcaagaag     840
cataaccttt ttttcacctt taaatatgga atcaaaatct atatttaatg ctttgtttaa     900
agctttaaaa ttgcatccaa ctgctgcaga taactgtgat tggctataca ccatagtatc     960
agaataactc attcttgtag gtatagtata tttagatgaa tactttgaat tccatgtatc    1020
taatatagaa tttattgcag aattaactga ggagtaggta ggtgaattaa caactttctt    1080
```

```
accatcttca gccataccog gtaagtcaac acttatagta ataggttttc tctcacatga    1140
aattatatca ggtttgtttt ccataagatt tctgttagca agttgtatag ctccaggata    1200
agttctatca tttattgagt ctataattga aatgtctgct gtggaatctg aaatactctt    1260
cttctcacgt tttaccacaa tgaacttatc tggattttca aatccttcag caggtacaaa    1320
attttctacc tgttcaccat tatatgataa atcttacgt ggatcatagg ataatccata    1380 aatattttg tctatgtcac tactgttgtc ttttgccaaa ttacattttg tatttgacgt    1440
tactacttgt ccattattga ttaatgaatg ttcctctaca tttcctttag ctaatacatt    1500
actggaatta taattagata ttaagccagt cattgaaaat attagcaatg aacgtgatac    1560
aaattttaat acattttgt tcat                                            1584
```

<210> SEQ ID NO 31
<211> LENGTH: 1587
<212> TYPE: DNA
<213> ORGANISM: Listeria ivanovii

<400> SEQUENCE: 31

```
atgaaaaaaa taatgctact tttaatgaca ttgttactag taagtttacc gttagcacaa      60
gaagctcaag cagatgcctc agtatatagt taccaaggca taatttcaca catggcacca     120
ccagcgtctc cgcctgcaaa gcctaagacg ccggttgaaa agaaaaatgc agctcaaatc     180
gatcaatata taacaagggct ggattatgat aaaaacaata tattagtgta cgatggagaa     240
gctgttaaaa atgttccacc aaaagcagga tacaagaag gaaatcaata tattgtagtg     300
gagaaaaaga aaaaatctat caatcaaaat aacgcagata ttcaagttat taactcgctt     360
gcaagcctta cttatccagg agctttagtg aaggcgaatt cagagttagt cgaaaatcaa     420
cccgatgtcc tccctgtgaa acgagattca gttacactta gtattgattt gcctggaatg     480
gttaaccatg acaatgaaat agtcgttcaa aatgcaacta atccaatat aaatgacgga     540 gtgaatactt tagtagatcg ttggaataat aaatactccg aagaataccc aaatattagt     600
gcgaaaattg actatgatca agaaatggcc tatagcgaat cgcaattagt tgcaaaattt     660
ggtgcagcat ttaaagctgt taataatagt ttgaatgtaa actttggagc gattagtgaa     720
ggtaaggtgc aagaagaagt tattaattc aaacaatt attatactgt taatgttaat     780
gaacctacaa gcccttccag attctttggt aaaagtgtta ctaaagaaaa cttgcaagcg     840
ctgggcgtaa atgcggaaaa tccacccgca tacatctcta gtgttgcata tggtcgtgac     900
attttcgtga aatttatcgac tagttcacac agcaccagag tgaaggctgc attcgatact     960
gcatttaagg gtaaatcagt taaggtgat acagaattag aaaatattat tcaaaatgct    1020
tcatttaaag cggtgattta tggtggtttca gccaaagatg aagtagaaat aattgatgga    1080
gatttaagca aattacgaga tattttaaaa caagggcgta atttttgataa gaaaaatccg    1140 ggcgtaccga ttgcgtatac aactaatttc ttgaaagata tcagttagc agttgttaaa    1200 aataattcgg aatatatcga aacaacttct aaggcttact cggatggaaa aattaaccta    1260
gatcattccg gtgcctatgt tgcgagattc aatgttactt gggatgaagt tagctatgat    1320
gctaatggaa atgaagttgt tgaacataaa aatggtccgg aaaatgataa agataagtta    1380
gctcatttta cgacatcaat ctatttgcca gggaatgcaa ggaatattaa tattcatgcg    1440
aaagaatgta ctggcttggc ttgggaatgg tgggagaacgg ttgtggatga tagaaacttg    1500
ccattagtaa aaaatagaaa tgtttgtatc tggggaacaa cgctttatcc agcgtatagt    1560
gatactgtag ataatccaat taagtaa                                        1587
```

<210> SEQ ID NO 32
<211> LENGTH: 1590
<212> TYPE: DNA
<213> ORGANISM: Listeria monocytogenes

<400> SEQUENCE: 32

| | | | | | |
|---|---|---|---|---|---|
| atgaaaaaaa | taatgctagt | ttttattaca | cttatattag | ttagtctacc | aattgcgcaa | 60 |
| caaactgaag | caaaggatgc | atctgcattc | aataaagaaa | atttaatttc | atccatggca | 120 |
| ccaccagcat | ctccgcctgc | aagtcctaag | acgccaatcg | aaaagaaaca | cgcggatgaa | 180 |
| atcgataagt | atatacaagg | attggattac | aataaaaaca | atgtattagt | ataccacgga | 240 |
| gatgcagtga | caaatgtgcc | gccaagaaaa | ggttataaag | atggaaatga | atatatcgtt | 300 |
| gtggagaaaa | agaagaaatc | catcaatcaa | aataatgcag | atatccaagt | tgtgaatgca | 360 |
| atttcgagcc | taacatatcc | aggtgctctc | gtgaaagcga | attcggaatt | agtagaaaat | 420 |
| caacccgatg | ttcttcctgt | caaacgtgat | tcattaacac | ttagcattga | tttgccagga | 480 |
| atgactaatc | aagacaataa | aattgttgta | aaaaatgcta | ctaaatcgaa | cgttaacaac | 540 |
| gcagtaaata | cattagtgga | agatggaat | gaaaaatatg | ctcaagctta | tccaaatgta | 600 |
| agtgcaaaaa | ttgattatga | tgacgaaatg | gcttacagtg | aatcacaatt | aattgcaaaa | 660 |
| tttggtacgg | catttaaagc | tgtaaataat | agcttgaatg | taaacttcgg | cgcaatcagt | 720 |
| gaagggaaaa | tgcaagaaga | agtcattagt | tttaaacaaa | tttactataa | cgtgaatgtt | 780 |
| aatgaaccta | aagaccttc | cagattttc | ggcaaagctg | ttactaaaga | gcagttgcaa | 840 |
| gcgcttggag | tgaatgcaga | aaatcctcct | gcatatatct | caagtgtggc | atatggccgt | 900 |
| caagtttatt | tgaaattatc | aactaattcc | catagtacta | agtaaaagc | tgcttttgac | 960 |
| gctgccgtaa | gtgggaaatc | tgtctcaggt | gatgtagaac | tgacaaatat | catcaaaaat | 1020 |
| tcttccttca | aagccgtaat | ttacggtggc | tccgcaaaag | atgaagttca | atcatcgac | 1080 |
| ggtaacctcg | gagacttacg | agatatttg | aaaaaggtg | ctacttttaa | ccgggaaaca | 1140 |
| ccaggagttc | ccattgccta | tacaacaaac | ttcttaaaag | acaatgaatt | agctgttatt | 1200 |
| aaaaacaact | cagaatatat | tgaaacaact | tcaaaagctt | atacagatgg | aaaaatcaac | 1260 |
| atcgatcact | ctggaggata | cgttgctcaa | ttcaacatct | cttgggatga | ataaaattat | 1320 |
| gatcctgaag | gtaacgaaat | tgttcaacat | aaaaactgga | gcgaaaacaa | taaaagtaag | 1380 |
| ctagctcatt | tcacatcgtc | catctatttg | ccaggtaacg | caagaaatat | taatgtttac | 1440 |
| gctaaagaat | gcactggttt | agcttgggaa | tggtggagaa | cggtaattga | tgaccggaac | 1500 |
| ctaccgcttg | tgaaaaatag | aaatatctcc | atctggggca | ctacacttta | tccgaaatat | 1560 |
| agtaatagtg | tagataatcc | aatcgaataa | | | | 1590 |

<210> SEQ ID NO 33
<211> LENGTH: 1593
<212> TYPE: DNA
<213> ORGANISM: Listeria seeligeri

<400> SEQUENCE: 33
atgaaaatat ttggtttagt tatcatgtcg ttgctatttg ttagtttgcc aataacacaa 60
caacctgaag cgagggatgt ccccgcgtac gatagaagcg aggtgactat atctcctgct 120
gaaacaccag agtccccacc ggcaacacca aaaacacctg tagagaaaaa gcatgcggaa 180
gaaattaata aatatatttg gggattaaac tatgataaaa atagtattct ggtctatcaa 240

-continued

```
ggtgaagcag ttacaaacgt tccaccgaaa aagggctaca agatggcag tgaatatatt      300 gtcgttgaaa aaagaaaaa aggtatcaat caaaacaatg cagacatttc tgtcataaat      360
gcaatttcga gccttactta tcctggagcg ttggtaaaag caaatagaga attagtagaa      420
aatcaaccta atgtactacc agtaaaacga gattcactta cattaagtgt agatttacca      480
ggaatgacta aaaagataa taaaatattc gttaaaaacc ctacaaagtc aaacgtaaat      540
aatgccgtga atacattagt agagcgttgg aatgataagt attcaaaagc gtatcctaat      600
attaatgcaa aaattgatta ttccgatgaa atggcttata gtgaatcaca attaattgcc      660
aaatttggga ctgcctttaa agctgttaat aatagtttga atgtaaattt tgaggcaatt      720
agtgatggga agtacaaga agaagtcatt agttttaagc aaatttatta taatattaac      780
gttaatgaac ctacaagtcc ttccaaattc tttgggggta gtgttaccaa agaacaacta      840
gatgctttag gtgtaaatgc cgaaaatcct cctgcttaca tttctagtgt tgcttacggt      900
cgccaagttt atgtgaaact atcctctagc tcgcatagta acaaagttaa aactgctttc      960
gaggcggcga tgagtggcaa atcagtgaaa ggggatgtag aattaacaaa tattataaaa     1020
aattcttctt ttaaagcagt catttatggt ggctcagcga agaagaggt tgaaattatt      1080 gatggcaatt taggcgaact tcgagatatt ttgaaaaaag ggtccactta tgatagagaa      1140
aaccctggcg ttccgatctc gtacacaact aactttttga agataatga cttagcggtt      1200 gttaaaaaca actcagaata tatcgaaaca acttcgaaat cttatacaga tggaaaaatt      1260
aatattgatc attctggtgg ttatgtagcc caattcaata tatcttggga tgaagtaagt      1320
tatgacgaga acgaaatga aataaaagtt cataagaaat gggggcgaaaa ttataagagt      1380 aagttagctc atttcacttc ttctatctat ttgccaggaa atgcgagaaa tattaacatc      1440
tatgcaagag aatgtaccgg cttgttttgg gaatggtgga gaactgttat agatgacaga      1500
aacttaccat tagtaaaaaa tagaaatgta tctatttggg gtacaacgct ttacccaaga      1560
cattctaata atgtagataa tccgattcag tag                                 1593
```

<210> SEQ ID NO 34
<211> LENGTH: 1494
<212> TYPE: DNA
<213> ORGANISM: Streptococcus suis

<400> SEQUENCE: 34

```
atgagaaaaa gttcgcactt gattttaagc tcaatagtca gtttggcact cgtaggggtc      60
acaccattga tgttcttgc agattccaaa caagatatta atcagtattt tcaaagcttg      120
acttacgagc cacaagagat tcttacaaat gagggagaat acattgataa tccgccagca      180
acaactggta tgttagaaaa cggacgtttt gtagtacttc gcagagaaaa gaagaatatt      240
acgaacaata gtgcagatat tgctgttatt gatgctaagg ctgcaaatat ttatccaggt      300
gctttattgc gtgctgacca aaatcttctg gataataatc aacgctttat cagtattgcg      360
cggggagatc tgacgcttag tttgaattta cctggttttgg ccaatgggga tagccacact      420
gttgtaaatt ctccaacaag aagtactgtt cgaacagggg tgaataaccct tctgtctaaa      480 tggaataata cgtatgctgg agagtatggc aatacccaag cagagcttca atatgatgaa      540
acaatggcat acagtatgtc acaattgaaa acgaagttcg gaacctcttt tgaaaaaatt      600
gctgtaccat tagatatcaa ttttgatgcc gtgaattcgg gtgaaaaaca ggttcagatt      660
gttaacttta aacaaattta ttatacagtt agtgttgatg aaccagaatc tccaagcaag      720 cttttttgcag aagggacaac tgtagaagat ttgaaacgaa atgggataac agatgaggta      780
```

| | | | |
|---|---|---|---|
| cctcctgttt | atgtttccag cgtttcttat | ggacgctcta tgttcatcaa | gttagaaact 840 |
| agcagtagga | gtacccaagt tcaagccgca | tttaaagcag ccatcaaagg | cgttgatatt 900 |
| agtggcaatg | ctgagtatca agacattctg | aaaaatactt cattctctgc | ttatatttt 960 |
| ggtgggatg | caggtagcgc ggctactgtt | gtgagcggaa atattgaaac | actgaagaag 1020 |
| attattgaag | aaggtgcaag atacggaaaa | ctcaatccag gtgttccgat | tcgtattca 1080 |
| accaactttg | tcaaagacaa tagacctgct | cagattttga gcaattcaga | gtacatagaa 1140 |
| acaacttcaa | cagtccataa tagcagtgca | ttgacattgg atcattcagg | tgcttatgtt 1200 |
| gcgaaataca | acattacttg gaagaagta | tcttacaatg aagctggaga | gaagtttgg 1260 |
| gaaccaaaag | cttgggataa aatggtgta | aatctgacct cacactggag | tgaaaccatt 1320 |
| caaattccag | gaaatgctcg caatcttcat | gtcaatattc aagaatgtac | aggattagca 1380 |
| tgggagtggt | ggagaacagt ttatgacaaa | gatttaccac ttgttggtca | acgtaaaata 1440 |
| accatctggg | gaacaacgtt atacccacag | tatgcggatg aggtgataga | gtaa 1494 |

```
<210> SEQ ID NO 35
<211> LENGTH: 1398
<212> TYPE: DNA
<213> ORGANISM: Streptococcus mitis

<400> SEQUENCE: 35
```

| | | | |
|---|---|---|---|
| atggcaaata | aagcagtaaa tgactttata | ctagctatgg attacgataa | aaagaaactc 60 |
| ttgacccatc | agggagaaag tattgaaaat | cgtttcatca aagaggggaa | tcagctaccc 120 |
| gatgagtttg | ttgttatcga agaaagaag | cggagcctgt cgacaaatac | aagtgatatt 180 |
| tctgtgacag | ctaccaacga cagtcgcctc | tatcctggag cacttctcgt | agtggatgag 240 |
| accttgttag | agaataatcc cactcttctt | gcggtcgatc gtgctccgat | gacttatagt 300 |
| attgatttgc | ctggtttggc aagtagtgat | agctttctcc aagtagaaga | tcccagcaat 360 |
| tcaagtgttc | gcggagcggt aaacgatttg | ttggctaagt ggcatcaaga | ttatggtcag 420 |
| gtcaataatg | tcccagctag aatgcagtat | gaaaaaatca cggctcacag | catgaacaa 480 |
| ctcaaggtca | agtttggttc tgactttgaa | agacaggga attctcttga | tattgatttt 540 |
| aactctgtcc | attcgggcga aaagcagatt | cagattgtta atttaagca | gatttattat 600 |
| acagtcagcg | tagatgctgt taaaaatcca | ggagatgtat tcaagatac | tgtaacggta 660 |
| gaggatttga | ggcagagagg aatttctgcc | gatcgtcctt tggtctatat | ttcgagtgtt 720 |
| gcttatgggc | gccaggttta tctcaagttg | agaccacga gtaagagtga | tgaagtcgag 780 |
| gctgcttttg | aagctttgat aaaaggagtc | aaggtagctc ctcagacaga | gtggaagcag 840 |
| attttggaca | atacagaagt gaaggcggtt | attttagggg cgacccgag | ttcgggtgcc 900 |
| cgagttgtaa | caggcaaggt ggatatggta | gaggacttga ttcaagaagg | cagtcgcttt 960 |
| acagccgatc | atccaggttt gccgatttct | tatacaactt cttttttacg | ggacaatgta 1020 |
| gttgcgacct | ttcaaaacag tacagactat | gttgagacta aggtgacagc | ctacagaaac 1080 |
| ggagatttac | tgctggatca tagtggtgcc | tatgttgctc aatattacat | tacttgggat 1140 |
| gaattatcct | atgattatca aggtaaggaa | gttttgactc ctaaggcttg | gaacagaaat 1200 |
| ggcaggatt | tgacggctca tttttaccact | agtattcctt taaaagggaa | tgttcgcaat 1260 |
| ctctctgtca | aaattagaga gtgtaccgga | cttgcctggg aatggtggcg | tacggtttat 1320 |
| gaaaaaaacg | atttgcccct agtgcgtaag | cggacgattt ctatttgggg | aacgactctt 1380 |

| | |
|---|---|
| tatcctcagg tagaggat | 1398 |

<210> SEQ ID NO 36
<211> LENGTH: 1599
<212> TYPE: DNA
<213> ORGANISM: Streptococcus intermedius

<400> SEQUENCE: 36

| | |
|---|---|
| atgaaaacta agcagaatat tgctcgcaaa ttgtcaagag ttgttttatt aagcactctc | 60 |
| gttctctctt cggcagcacc gatttcagct gcattcgctg aaacacctac caaaccaaaa | 120 |
| gcagctcaaa cagagaaaaa acccgaaaag aaaccggaaa acagcaactc tgaagctgca | 180 |
| aaaaaagctc tgaatgatta tatttgggga ttgcagtatg ataaactaaa cattttaaca | 240 |
| caccaaggtg aaaaattgaa aaaccactct agccgcgagg catttcatcg cccaggtgag | 300 |
| tatgttgtta tcgaaagaa aaaacaaagc atttcaaacg caacatctaa gttatctgta | 360 |
| agttcagcaa atgatgaccg catcttccca ggtgcattgc taaaagcgga ccaaagtttg | 420 |
| ttagaaaatc ttccaaccct aatcccagtt aatcgcggca aacaactat tagtgtaaac | 480 |
| ttaccgggat tgaaaaatgg cgaaagtaat cttacagttg aaaatccatc caacagtaca | 540 |
| gttcgaacag ctgttaacaa tttagttgaa aatggattc aaaaatactc taaaactcat | 600 |
| gctgtgccag ctagaatgca atatgaatct attagcgccc aaagcatgag ccaattacaa | 660 |
| gcaaatttg gtgctgattt ctcaaaagtc ggtgcaccac ttaatgttga cttctcatct | 720 |
| gttcacaaag gtgaaaaaca gtatttatt gcgaacttta gacaagttta ctacacagct | 780 |
| agcgtagact ctccaaatag tccttctgca ctctttggct ctggtatcac accaactgat | 840 |
| ttaatcaatc gtggagttaa ttctaaaacc ccaccagttt atgtttcaaa tgtatcatat | 900 |
| ggccgtgcaa tgtatgtgaa atttgaaact acaagcaaga gtacaaaagt acaagccgct | 960 |
| attgatgctg ttgttaaagg agcaaaactt aaagctggaa cagaatatga aaatattcta | 1020 |
| aaaaatacta aaatcactgc tgttgttctc ggtggtaacc caggtgaagc ttctaaagtc | 1080 |
| atcacaggta atattgatac tttgaaagat ttgatccaaa aaggtagcaa tttcagtgct | 1140 |
| caaagtccag ctgtaccaat ctcttacact acttctttg taaaagacaa ttctattgca | 1200 |
| actatccaaa acaacacaga ctacatcgaa acaaaagtaa catcctataa agatggtgct | 1260 |
| ctcacccctca atcatgatgg tgctttcgtt gcacgcttct atgtttattg gaagaactc | 1320 |
| ggacatgatg ctgatggcta cgaaactatt cgctcaagat cttggagtgg aaatggctac | 1380 |
| aatcgcggtg cacactattc tacaactctc cgtttcaagg gaaatgttag aaacattcgc | 1440 |
| gtaaaagtac taggagccac tggactagct tgggagcctt ggagactgat ctatagcaag | 1500 |
| aacgatcttc ctttggttcc acaaagaaac attagcactt ggggaacaac ccttcatcca | 1560 |
| cagtttgaag ataaagttgt gaaagataac actgattaa | 1599 |

<210> SEQ ID NO 37
<211> LENGTH: 1998
<212> TYPE: DNA
<213> ORGANISM: Streptococcus mitis

<400> SEQUENCE: 37

| | |
|---|---|
| atgaatcaag aaaaacgttt gcatcgcttt gtcaaaaagt gtggactcgg tgtgtgtagt | 60 |
| gctgttgttg cggcctttt attgaacgct cagggagtag ctttggctac agagcaaggg | 120 |
| aatcgtccag ttgagaccga aaacatcgct cgtgaaaaac aagctagtca agttctact | 180 |
| gcttatggag gagctgctgc acgagcagtg gacggtaatg ttgacagtga ctatgggcac | 240 |

```
cattctgtaa cgcacacaaa ctttgaagac aatgcttggt ggcaagttga tcttggaaaa      300
acagagaatg ttggaaaagt taaactctac aatcgtggag atgggaatgt agctaatcgt      360
ctttccaatt tgatgttgt tttgttaaat gaagcaaaac aagaagttgc tcgtcaacac       420
tttgatagtt tgaatgggaa ggcagaactt gaagttttct tcaccgccaa agccgctcgt      480
tatgtaaaag tggagttgaa aactaaaaat accccattga gcttggcaga agtggaagta     540
ttccgttcag caacaactca agttggacag gatagaactg caccagtagt agatcaaaca     600
tcagcattga aagactacct ttttggctta gcttataatc ctttggatat tttaactcgc      660
aagggagaaa ccttagaaaa tcgctacaac acaagtgcta aggaacaaaa tggagagttt     720
gtcgttgtag aaaaaatcaa gaaaaccctc tctacaggca cagcagatgt ttccatcaat      780
ggaaatcaaa atgtcttcct aggtggcttg tataaggcaa accaaaatct gctagaaaat      840
cagccagaat tgattagtct tgcccgtgca aaggggacag tcagcgtcga tttacctggt      900
atgattcagt ctgacagccg aattgaagca gatcctacaa ctagtggtat gcagtctgcg     960
atgaatacct tggttgaaag atggacaaag aattactcat ctagccattc cgttcctgcc      1020
cgtgttcagt atgaatcaac tacagcctat agcatgaatc aattgaaagc aaaatttggt     1080
gcagactttg aaaaagcagg tgcaccgctc aagattgact ttgaggctgt gcaaagggt      1140 gaaaagcaaa ttgaagttgt aaactttaaa caaatctact atacagcgac atttgatgca     1200
ccgaccaatc cagcggctgt atttgacaag agtgtgacac ctgaagattt aaaacaaaga     1260
ggcgttgatt cacaaactcc acctgtatat gtatcaaatg tttcttacgg acgtcaaatc     1320
tatgttaagt ttgagtcagc aagtaagtct actgaattaa aagcagctat taatgcggtt     1380
atcaaaggcg caacaattgc tccaaattct gaatggagcc gtctattgaa gaatacttct     1440
gtaacagcgg taattgtagg aggtaatgct agcggtgccg ccaaagttgt cacaggaaca     1500
gtcgaaaact tgaaggaact catcagagaa ggagctaact ttagcgctca aagtccagct     1560
gtgccaatct catataagac tgccttccta aaagataatg cccaagcaac tttacaaaat    1620
agtacagact atatcgaaac gaaggttact tcttacaaaa atggtttctt gaaacttcat     1680
cataagggtg cttatgttgc gcgttactac atctattggg atgaaattac atatgatgaa    1740
caaggaaatc cagaaatccg ttcacgtcaa tgggaagata acggaaaaaa cagaacttca    1800
ggcttccaaa cagagattca atttagagga atgtccgta atcttcgcat caaggttcaa      1860
gaaaagacgg gtcttgtatg ggaaccatgg cgtacagttt acaaccgcac agacttacca    1920
ctagtacaac agcgtacaat tacacattgg ggaacaactc taaaccctaa agttgatgaa    1980
aaaattgtga atgagtaa                                                   1998
```

<210> SEQ ID NO 38
<211> LENGTH: 1605
<212> TYPE: DNA
<213> ORGANISM: Arcanobacterium pyogenes

<400> SEQUENCE: 38

```
atgaaacgaa aggcttttgc atcgctagtg gcgagtgtag tcgcagcagc aactgtcacg       60
atgcccacag catcttttgc tgccggattg ggaaacagct cgggattgac ggacggcttg     120
tcagcgccgc gagcctccat ctccccgacg gataaagttg accttaagtc ggcgcaagag    180
accgacgaga cgggcgtcga taagtacatt cgtggtctga atacgatcc ctctggtgta     240 cttgcagtca agggtgagtc tattgaaaat gtgccggtta ccaaggatca gctcaaggac    300
```

```
ggcacctaca cggtatttaa gcatgaacgc aagagtttta acaatttgcg ttcggacatc    360
tctgcgttcg atgcgaacaa cgcccacgtc tatcctggcg cgctcgtgtt agcaaataaa    420
gatcttgcaa aaggtagtcc gacttcgatc ggaattgcac gtgctccgca aactgtcagc    480
gtcgacttgc caggattagt tgacggtaag aataaggtcg tcatcaacaa tcccacgaag    540
agttccgtga ctcaaggact gaacggcctt ctcgacggtt ggattcagcg caatagcaag    600
tatcctgacc atgctgcaaa gatctcctac gatgagacta tggtgacgtc aaagcgtcaa    660
ctggaggcaa agcttggcct cggatttgaa aaggtctcag ccaagctcaa cgtggacttc    720
gatgcaattc ataagcgtga acggcaggtg gctatcgctt ccttcaaaca gatttactac    780
acggctagcg tagatacacc gacatctcca catagcgttt tcggcccgaa tgtcaccgca    840
caggatttga aagatcgggg agtcaataac aagaatcctc taggatacat ttcgtcggtc    900
agctatggac gccagatttt tgtcaagctg gaaacgacct cgacttccaa tgatgtacaa    960
gcggctttta gcggcctgtt caaagctaag ttcggcaatc tttccacaga gttcaaggct    1020
aagtatgccg atatcctgaa caagacccga gctactgtgt acgctgttgg tggcagcgct    1080
agaggcggag ttgaagttgc aactggcaat atcgatgcac tcaagaagat catcaaggag    1140
gaaagcacct actctacgaa ggttcctgcc gtgcccgttt cctatgccgt caatttcttg    1200
aaggataatc agttggcagc tgttaggagc agcggtgatt acattgaaac cactgcaacg    1260
acttacaagt ctggtgagat caccttccgc catggcggtg gctacgtcgc aaagttcagg    1320
ctgaagtggg acgagatcag ctacgacccg cagggcaagg aaatccgtac acccaagacg    1380
tggagcggga attgggcagc ccgcacccct ggcttccgtg agactattca acttccagca    1440
aacgcgcgca acatccatgt ggaagcaggc gaggcaactg gcctagcgtg ggatccgtgg    1500
tggaccgtta tcaataagaa gaatctcccc ttggtgccac atcgagagat cgtccttaag    1560
ggcacgacgc tcaatccctg ggtcgaggac aatgtcaaat cctag                   1605
```

<210> SEQ ID NO 39
<211> LENGTH: 11
<212> TYPE: PRT
<213> ORGANISM: Streptococcus pneumoniae

<400> SEQUENCE: 39

Glu Cys Thr Gly Leu Ala Trp Glu Trp Trp Arg
1               5                   10